United States Patent [19]

Haseba et al.

[11] Patent Number: 5,702,641

[45] Date of Patent: Dec. 30, 1997

[54] LIQUID CRYSTALLINE COMPOUND CONTAINING FLUORINE ATOM SUBSTITUTED ALKYL GROUP(S) AND A LIQUID CRYSTAL COMPOSITION

[75] Inventors: Yasuhiro Haseba; Kazutoshi Miyazawa; Shuichi Matsui; Tomoyuki Kondo; Yasuyuki Goto; Etsuo Nakagawa; Shinichi Sawada, all of Chiba-ken, Japan

[73] Assignee: Chisso Corporation, Osaka, Japan

[21] Appl. No.: 576,461

[22] Filed: Dec. 21, 1995

[30] Foreign Application Priority Data

Dec. 22, 1994 [JP] Japan .................................. 6-320218

[51] Int. Cl.$^6$ .......................... C09K 19/30; C09K 19/52; G02F 1/13
[52] U.S. Cl. .................. 252/299.63; 252/299.01; 252/299.66; 570/129; 349/187
[58] Field of Search .................. 252/299.01, 299.63, 252/299.66; 570/127, 129; 428/1; 349/187

[56] References Cited

U.S. PATENT DOCUMENTS 5,368,772  11/1994  Rieger et al. .................. 252/299.63
5,389,289  2/1995  Rieger et al. .................. 252/299.01

FOREIGN PATENT DOCUMENTS 4123539  1/1993  Germany .

WO91/16393  10/1991  WIPO .
WO91/16394  10/1991  WIPO .
WO91/16395  10/1991  WIPO .
WO91/16401  10/1991  WIPO .
WO91/17135  11/1991  WIPO .

*Primary Examiner*—Shean C. Wu
*Attorney, Agent, or Firm*—Wenderoth, Lind & Ponack

[57] ABSTRACT

A liquid crystalline compound exhibiting a large $\Delta\epsilon$ value, an electrical and chemical stability and a superior compatibility with existing liquid crystalline compounds, a liquid crystal composition containing the same, and a liquid crystal display element constructed by using the composition are provided, which liquid crystalline compound is expressed by the formula (I).

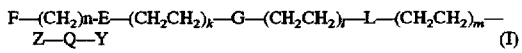

wherein n is an integer of 1 to 10; k, l and m each independently are an integer of 0 to 2; ring E is 1,4-cyclohexylene group or 1,4-phenylene group, wherein one or more H atoms on each six-membered ring may be replaced by F atom(s); G and L each independently is a covalent bond or 1,4-cyclohexylene group or 1,4-phenylene group, wherein one or more H atoms on each six-membered ring may be replaced by F atom(s); Q is covalent bond or —O—; Y is a fluoroalkyl group of 1 to 3C or F atom; but in the case where ring E is 1,4-cyclohexylene group and at least one of G and L is covalent bond, k+l+m≠0, and in the case where Q is —O—, Y is not F atom.

20 Claims, No Drawings

LIQUID CRYSTALLINE COMPOUND CONTAINING FLUORINE ATOM SUBSTITUTED ALKYL GROUP(S) AND A LIQUID CRYSTAL COMPOSITION

BACKGROUND OF THE INVENTION

1. Field of the Invention

This invention relates to a liquid crystalline compound effective as a component of liquid crystal composition, particularly a liquid crystalline compound preferred to be used as a component for TFT liquid crystal composition, a liquid crystal composition containing the same and a liquid crystal display element constituted by using the composition.

2. Description of the Related Art

Liquid crystal display elements are materials utilizing the optical anisotropy and the dielectric anisotropy of liquid crystal substances. They are classified into various kinds of modes such as TN mode (twisted nematic mode), DS mode (dynamic scattering mode), guest-host mode, DAP mode (deformation of aligned phase mode), STN mode, etc., depending upon the display mode of the element, and the properties of liquid crystal substances suitable to the respective uses therein are varied. Recently higher display grade of liquid crystal display elements has been particularly required, and in order to comply with the requirement, demand upon display element of active matrix mode represented by thin film transistor (TFT) has been increased. Liquid crystal substances used for any display elements not only require stability to moisture, air, heat, light, etc., but also they should exhibit liquid crystal phase within a temperature range as broad as possible, around room temperature, and also have a low viscosity, a superior compatibility, a large dielectric anisotropy value ($\Delta\epsilon$) and an optimum optical anisotropy value ($\Delta n$). However, at present, there is no single compound which satisfies all of such conditions. Thus, it is the present status that liquid crystal compositions obtained by blending several kinds of liquid crystal compounds or non-liquid crystal compounds have been used.

A characteristic particularly required for TFT mode liquid crystal display element is to retain a high contrast during a frame period; hence liquid crystal substances used for this object are required to exhibit a large specific resistance value in addition to the above described conditions. Further, recently, a low voltage drive has been sought for TFT mode liquid crystal display element; hence in order to comply with this requirement, a liquid crystalline compound or liquid crystal composition having a larger $\Delta\epsilon$ than those of liquid crystal materials so far used for TFT mode liquid crystal display elements has been required.

General liquid crystalline compounds very often contain cyano group, and when liquid crystalline compounds containing cyano group are used in TFT mode liquid crystal display element, decomposition thereof occurs under high voltage; hence it is impossible to retain high specific resistance value during display operation. Thus, in spite of the fact that liquid crystalline compounds containing cyano group have a high $\Delta\epsilon$, it is impossible to use the compounds for TFT mode liquid crystal display element. Thus, in order to overcome this defect, development of a liquid crystal material which exhibits a high specific resistance value and nevertheless has a high $\Delta\epsilon$ has been vigorously carried out. As liquid crystalline compounds having a high specific resistance value, fluorine-containing compounds are suitable. As these compounds, generally, liquid crystalline compounds containing fluorine atom as substituent group, the following compounds have been known:

For example, Japanese patent publication No. Hei 02-40048 discloses the following compound expressed by the formula (1):

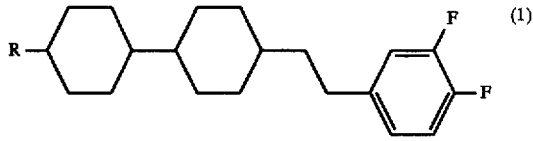

The compound (1) has a high specific resistance as compared with compounds having cyano group; hence it has been industrially used, but its $\Delta\epsilon$ is as small as about 4; hence a sufficient low voltage drive cannot be realized.

Japanese patent application laid-open No. Hei 02-233626 discloses, as a compound having a $\Delta\epsilon$ larger than that of the above compound (1), the following trifluorophenyl compound expressed by the following formula (2):

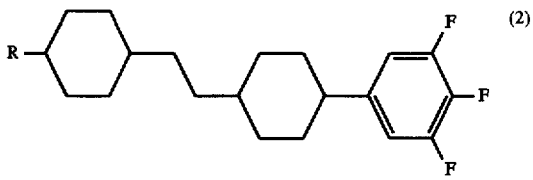

However, this compound exhibits an insufficient $\Delta\epsilon$ value to an extent of about 8 and further has a structure wherein a greater number of fluorine atoms than those of the above compound (1) are introduced thereinto. Thus, the compound has a very narrow liquid crystal phase temperature range, so that it is unsuitable as a component constituting a liquid crystal composition. Further, even from the standpoint of N-I point, it has been confirmed that an example of the compound of the formula (2), 1-(4-propylcyclohexyl)-4-(3,4,5-trifluorophenyl)cyclohexane, has an N-I point lower by about 60° C. than that of, an example of monofluoro compounds, 1-(4-propylcyclohexyl)-4-(4-fluorophenyl)cyclohexane, and also the compound has an N-I point lower by about 25° C. than that of an example of difluoro compounds, 1-(4-propylcyclohexyl)-4-(3,4,-difluorophenyl)cyclohexane.

Further, Japanese patent application laid-open No. Hei 04-506361 discloses compounds expressed by the following formulas (3), (4) and (5):

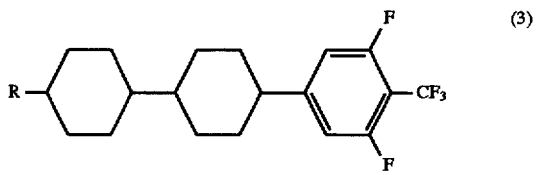

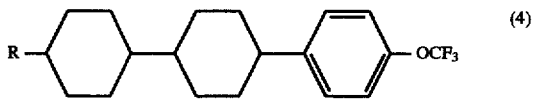

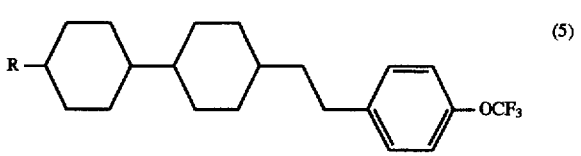

These compounds each have relatively large $\Delta\epsilon$ (for example, compounds (4) and (5) have $\Delta\epsilon$ of about 7), but they have a far inferior compatibility with existing liquid crystalline compounds at low temperature, hence they have been unsuitable as a constituent component of liquid crystal compositions. In order to improve the compatibility, a compound having fluorine atom introduced into R as an alkyl group has been disclosed in Japanese patent application Hyo No. Hei 04-506817. This compound is a structure of two or three rings having cyclohexyl group and phenyl group at the terminal end thereof such as a compound expressed by the following formula (6):

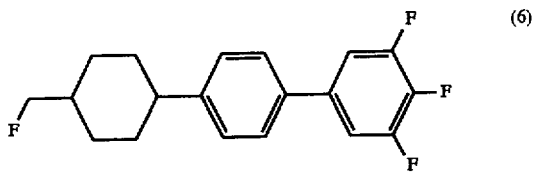

However, this compound contains only a single bond at the central part of the molecule, but does not contain another bonding group such as 1,2-ethylene group. Further, the substituents on the phenyl group as the above terminal group are limited to fluorine atom, and other substituents such as fluoroalkyl group or fluoroalkoxy group are neither taught nor suggested.

However, these compounds do not improve the compatibility at all, and in particular, the compound of the formula (6) does not exhibit even any liquid crystal phase. As described above, a compound having a large $\Delta\epsilon$ and a superior compatibility has not yet been known. Thus, when a liquid crystalline compound having a large $\Delta\epsilon$ is used as a component of a composition, it is impossible to increase the mixing ratio of the compound; hence it is the present status that the $\Delta\epsilon$ value of the composition is restricted. Accordingly, appearance of a liquid crystalline compound having a high specific resistance value and a large $\Delta\epsilon$ and at the same time, having a superior compatibility with existing liquid crystalline compounds, has been awaited.

SUMMARY OF THE INVENTION

The object of the present invention is to provide a liquid crystalline compound having overcome the drawbacks of the prior art and having a large $\Delta\epsilon$ value, an electric and chemical stability, and a superior compatibility with existing liquid crystalline compounds, and a liquid crystal composition containing the same and further a liquid crystal display element constituted by using the same.

The present invention has the following constitutions (1) to (17):

(1) A liquid crystalline compound expressed by the formula (I):

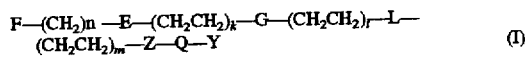

wherein n represents an integer of 1 to 10; k, l and m each independently represent an integer of 0 to 2; ring E represents 1,4-cyclohexylene group or 1,4-phenylene group wherein one or more hydrogen atoms on the six-membered ring may be replaced by fluorine atom(s); G and L each independently represent a covalent bond or 1,4-cyclohexylene group or 1,4-phenylene group wherein one or more hydrogen atoms may be replaced by fluorine atom(s), provided that when only one of G or L is a covalent bond, G is the covalent bond; ring Z represents 1,4-phenylene group wherein one or more hydrogen atoms on the 1,4-phenylene group may be replaced by fluorine atom(s); Q represents a covalent bond or —O—; Y represents a fluoroalkyl group of 1 to 3 carbon atoms or fluorine atom; and when ring E represents 1,4-cyclohexylene group and at least one of G and L represents a covalent bond, k+l+m≠0 and when Q represents —O—, Y does not represent fluorine atom.

(2) A liquid crystalline compound according to item (1), wherein k, l and m each independently represent 0 or 1, and ring E represents 1,4-phenylene group or fluorine-substituted 1,4-phenylene group.

(3) A liquid crystalline compound according to item (1), wherein k, l and m each independently represent 0 or 1 and ring E represents 1,4-cyclohexylene group.

(4) A liquid crystalline compound according to item (3), wherein k, l and m each are zero; G represents a covalent bond; and L represents 1,4-cyclohexylene group, 1,4-phenylene group or fluorine-substituted 1,4-phenylene group.

(5) A liquid crystalline compound according to item (4), wherein L represents 1,4-cyclohexylene group.

(6) A liquid crystalline compound according to item (4), wherein L represents 1,4-phenylene group or fluorine-substituted 1,4-phenylene group.

(7) A liquid crystalline compound according to item (3), wherein k and l each represent 0; m represents 1; G represents a covalent bond; and L represents 1,4-cyclohexylene group, 1,4-phenylene group or fluorine-substituted 1,4-phenylene group.

(8) A liquid crystalline compound according to item (7) wherein L represents 1,4-cyclohexylene group.

(9) A liquid crystalline compound according to item (7), wherein L represents 1,4-phenylene group or fluorine-substituted 1,4-phenylene group.

(10) A liquid crystalline compound according to item (3), wherein k and m each represent 1; l represents 0; G represents a covalent bond; and L represents 1,4-cyclohexylene group, 1,4-phenylene group or fluorine-substituted 1,4-phenylene group.

(11) A liquid crystalline compound according to item (3), wherein k represents 1; Z and m each represent 0; and G and L each represent a covalent bond.

(12) A liquid crystalline compound according to item (1), wherein G and L each independently represent 1,4-cyclohexylene group, 1,4-phenylene group or fluorine-substituted phenylene group.

(13) A liquid crystal composition containing at least one of liquid crystalline compounds according to items (1) to (12).

(14) A liquid crystal composition characterized by containing at least one member of the liquid crystalline compounds set forth in either one of items (1) to (12), as a first component, and at least one member of compounds selected from the group consisting of compounds expressed by the following formulas (II), (III) and (IV), as a second component:

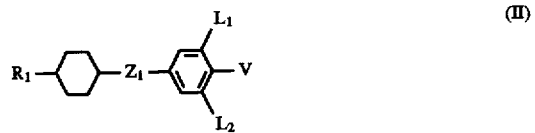

-continued

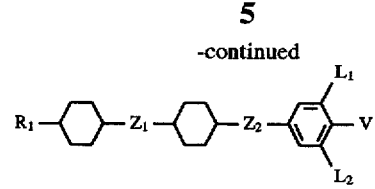  (III)

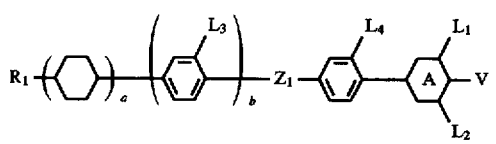  (IV)

wherein $R_1$ represents an alkyl group of 1 to 10 carbon atoms; V represents F, Cl, $CF_3$, $OCF_3$, $OCF_2H$ or an alkyl group of 1 to 10 carbon atoms; $L_1$, $L_2$, $L_3$ and $L_4$ each independently represent H or F; $Z_1$ and $Z_2$ each independently represent —$(CH_2)_2$—, —CH=CH— or a covalent bond; ring A represents trans-1,4-cyclohexylene group or 1,4-phenylene group; a represents 1 or 2; and b represents 0 or 1.

(15) A liquid crystal composition characterized by containing at least one member of the liquid crystalline compounds set forth in either one of items (1) to (12), as a first component, and at least one member of compounds selected from the group consisting of compounds expressed by the following formulas (V), (VI), (VII), (VIII) and (IX), as a second component:

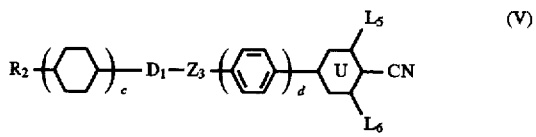  (V)

wherein $R_2$ represents F, an alkyl group of 1 to 10 carbon atoms or an alkenyl group of 2 to 10 carbon atoms, and in either of the groups, an optional methylene group (—$CH_2$—) in the groups may be replaced by oxygen atom (—O—), but two or more methylene groups therein are not successively replaced by oxygen atom; $Z_3$ represents —$(CH_2)_2$—, —COO or a covalent bond; $L_5$ and $L_6$ each independently represent H or F; $D_1$ represents trans-1,4-cyclohexylene group, 1,4-phenylene group or 1,3-dioxane-2,5-diyl group; ring U represents trans-1,4-cyclohexylene group or 1,4-phenylene group; and c and d each independently represent 0 or 1,

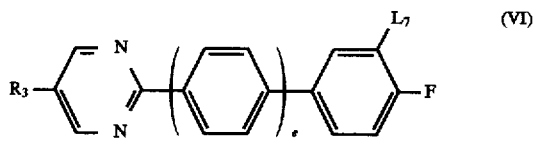  (VI)

wherein $R_3$ represents an alkyl group of 1 to 10 carbon atoms; $L_7$ represents H or F; and e represents 0 or 1,

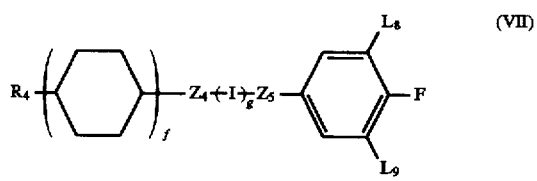  (VII)

wherein $R_4$ represents an alkyl group of 1 to 10 carbon atoms; I represents trans-1,4-cyclohexylene group or 1,4-phenylene group; $L_8$ and $L_9$ each independently represent H or F; $Z_4$ represents —COO— or a covalent bond; $Z_5$ represents —COO— or —C≡C—; and f and g each independently represents 0 or 1, $R_5$—W—$Z_6$—K—$R_6$  (VIII)

wherein $R_5$ and $R_6$ each independently represent an alkyl group, an alkoxy group or an alkoxymethyl group, each of 1 to 10 carbon atoms; W represents trans-1,4-cyclohexylene group, 1,4-phenylene group or 1,3-pyrimidine-2,5-diyl group; K represents trans-1,4-cyclohexylene group or 1,4-phenylene group; and $Z_6$ represents —C≡C—, —COO—, —$(CH_2)_2$13 or a covalent bond,

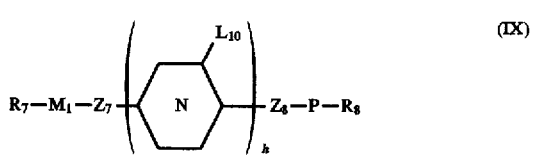  (IX)

wherein $R_7$ represents an alkyl group or an alkoxy group each of 1 to 10 carbon atoms; $R_8$ represents an alkyl group of 1 to 10 carbon atoms, and an optional methylene group (—$CH_2$—) in $R_8$ may be replaced by oxygen atom (—O—), but two or more methylene groups are not successively replaced by oxygen atom (—O—); M, represents trans-1,4-cyclohexylene group or 1,3-pyrimidine-2,5-diyl group; rings N and P each independently represent trans-1,4-cyclohexylene group or 1,4-phenylene group; $Z_7$ represents —COO—, —$(CH_2)_2$—, —CH=CH— or a covalent bond; $Z_6$ represents —C≡C—, —COO— or a covalent bond; h represents 0 or 1; and $L_{10}$ represents H or F.

(16) A liquid crystal composition characterized by containing at least one member of the liquid crystalline compounds set forth in either one of items (1) to (12), as a first component, and at least one member of compounds selected from the group consisting of compounds expressed by the formulas (II), (III) and (IV), as a part of the second component, and at least one member of compounds selected from the group consisting of compounds expressed by the formulas (V), (VI), (VII), (VIII) and (IX), as another part of the second component. (17) A liquid crystal display element constituted by using either one of the liquid crystal compositions set forth in either one of the items (13) to (16).

DETAILED DESCRIPTION OF THE INVENTION

The liquid crystalline compound expressed by the formula (I) of the present invention is characterized in that the compound has a structure of 2 to 4 rings, having a group selected from the group consisting of fluorine atom, a fluoroalkyl group and a fluoroalkoxy group, each of 1 to 3 carbon atoms, on a phenyl group which is a terminal ring on one side of the molecule, and having fluorine atom-containing group on another terminal ring of the molecule, and in the case of 2 to 3 ring structures, at least one of 1,2-ethylene or 1,4-butylene bonding group is introduced into the central bonding part of the molecule. By having such a structure, the compound (I) of the present invention either exhibits a large Δε and a superior compatibility and further exhibits a low viscosity and a high stability, i.e. a high specific resistance value, and most of the compound exhibits a broad mesomorphic range. Thus, when such compounds of the present invention are used as a component of liquid crystal composition, a novel liquid crystal composition having preferable characteristics can be provided.

As described above, any of the liquid crystalline compounds expressed by the formula (I) by the present invention exhibit superior characteristics, and among the compounds, those expressed by the following formulas (1-1) to (1-25) are preferable in that they have a large Δε and a superior compatibility. In addition, in the respective formulas, Q and Y each are as defined above; $T_1$ to $T_8$ each independently represent H or F; $S_1$ represents $(CH_2CH_2)_k$; $S_2$ represents $(CH_2CH_2)_l$; $S_3$ represents $(CH_2CH_2)_m$; and k, l and m are as defined above.
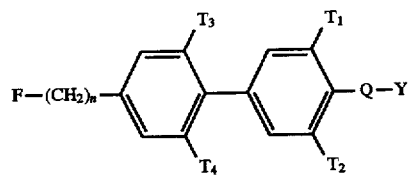
(1-1)
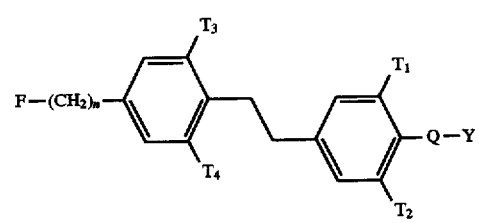
(1-2)
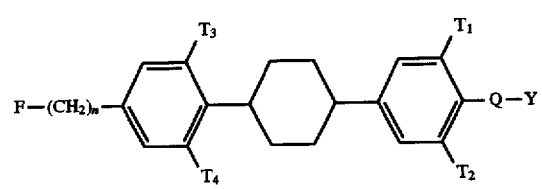
(1-3)
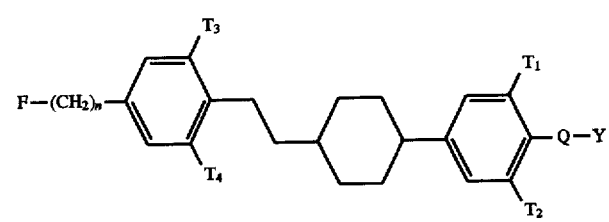
(1-4)
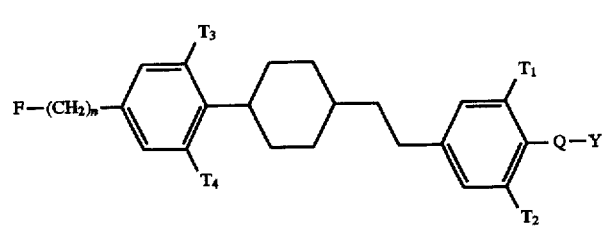
(1-5)
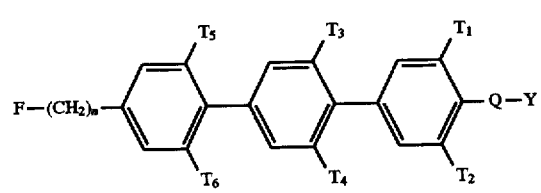
(1-6)
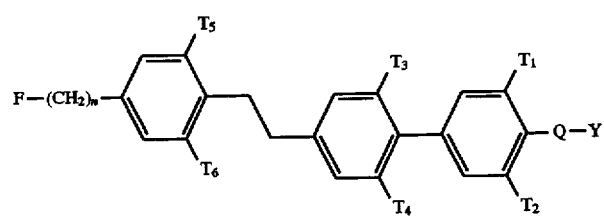
(1-7)

-continued
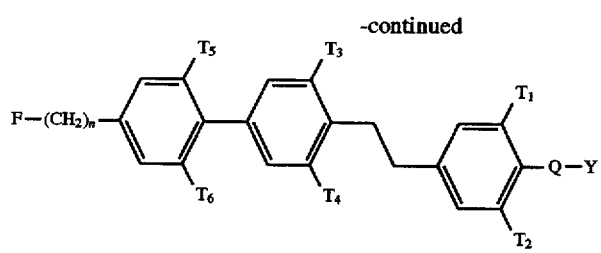 (1-8)
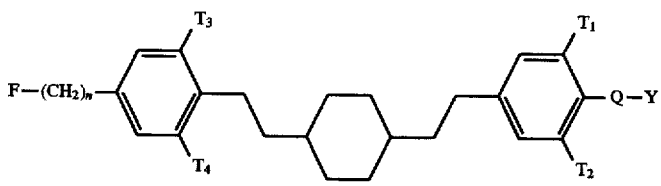 (1-9)
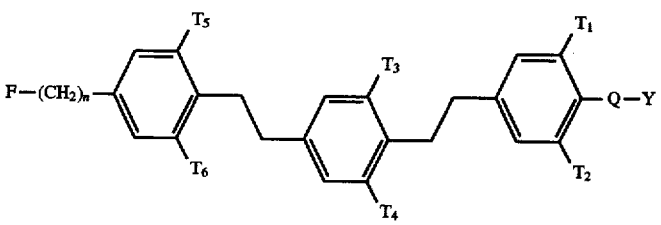 (1-10)
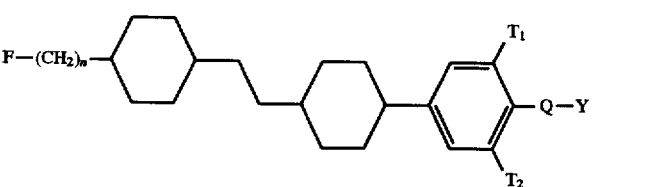 (1-11)
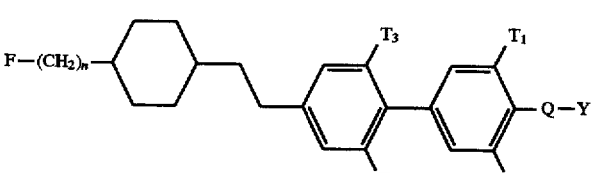 (1-12)
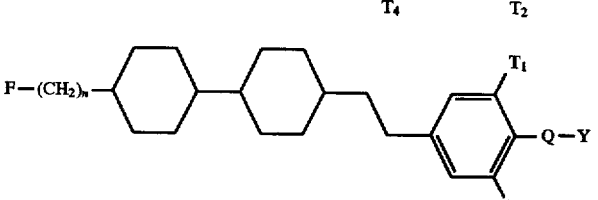 (1-13)
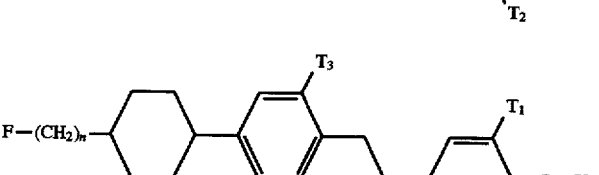 (1-14)
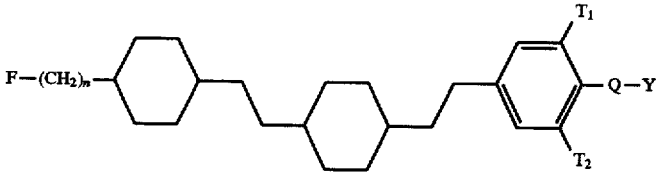 (1-15)

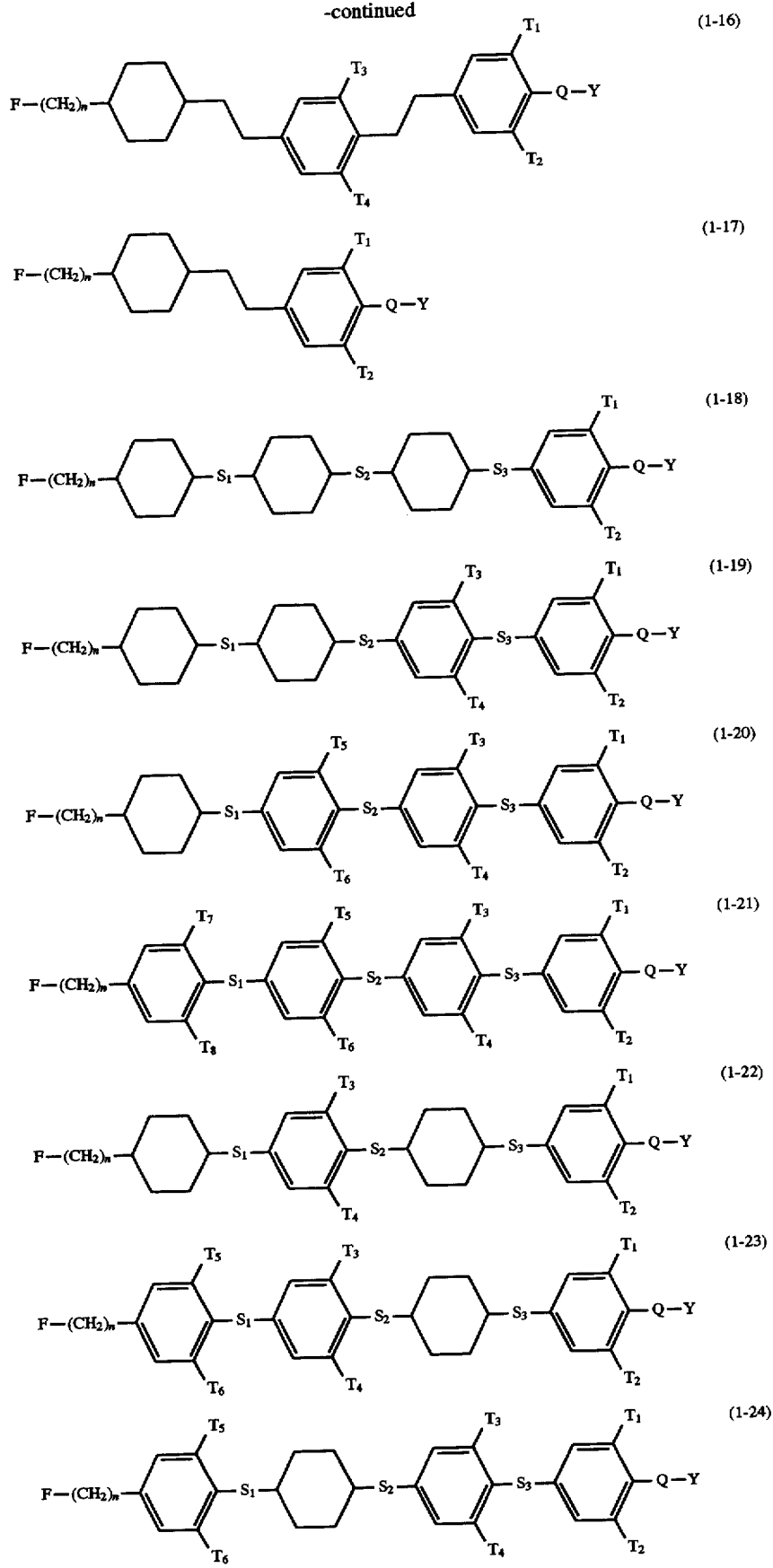

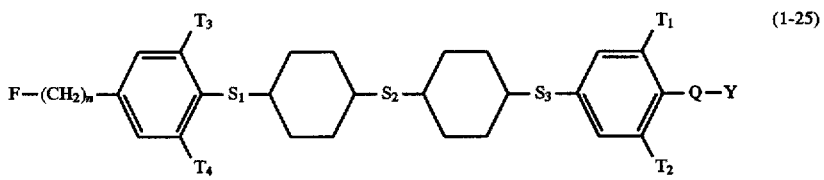

In these compounds, compounds expressed by the bicyclic formulas (1-1), (1-2) and (1-17) exhibit superior characteristics of a very good compatibility and also a low viscosity. Among these, particularly those included in the formulas (1-1) and (1-2) wherein two rings are both phenyl group, have also a characteristic of a large Δn. Thus, these bicyclic compounds are effective when they are used as a component of composition needing a low viscosity.

Tricyclic compounds (1-3) to (1-16) and tetracyclic compounds (1-18) to (1-25) both have a high clearing point; hence they are effective for broadening a mesomorphic range. In addition to this, particularly among the tricyclic compounds, compounds having an ethylene bond between the rings, have a superior compatibility; hence they are effective as a component of a liquid crystal composition used in use applications needing the above characteristic, for example, in the liquid crystal display element of TFT mode used in a television in an automobile. Further, the tetracyclic compounds are effective for elevating the upper limit of the clearing point of the compositions containing them even by using a small quantity thereof. When they are used, those having linear rings having the respective rings bonded by covalent bonds are suitable to compositions needing a low viscosity, and on the other hand, those having ethylene bonds between the respective rings, which have a further superior compatibility, are suitable to compositions needing a further broad mesomorphic range.

Among the substituent Q—Y, those having a particularly superior characteristic are $CF_3$, $OCF_3$, —$OCF_2H$, $OCF_2CFHCF_3$, —$CF_2CF_2H$ or F. However, in the case where the substituent is F, this F has a property of increasing Δε; hence substituent F other than the above F may be 3-position substituent or 3-position and 5-position substituent. In the case where the substituent Q—Y is a substituent other than F, i.e. a fluoroalkyl group or fluoroalkoxy group each of 1 to 3 carbon atoms, the resulting liquid crystalline compound exhibits a particularly large Δε. In particular, a compound wherein Q—Y is —$CF_3$, exhibits a very large Δε, and a compound wherein Q—Y is —$OCF_3$ exhibits a large Δε and also a low viscosity. Further, a compound wherein Q—Y is —$OCF_2CFHCF_3$ or $OCF_2CF_2H$ exhibits a large Δε and also a particularly large Δn. Namely, by variously altering Q—Y as described above, it is possible to obtain a compound having desired characteristics.

In the case where a further large Δε value is required, fluorine atom(s) may be further introduced into rings E, G, L and Z.

Further, in the case where a larger Δn is required, a compound containing more phenyl groups may be chosen.

The compound expressed by the formula (I) can be effectively prepared according to a known process, for example according to the following processes:

(Introduction of Q—Y group)

In the following description, $T_1$ and $T_2$ in the formulas are as defined above; $r_1$ represents an integer of 0 to 2, $r_0$, $r_2$ and $r_3$ each represent an integer of 0 or 1.

A case where Q—Y represents perfluoroalkoxy group:

The compound of this case can be prepared according to a known process, for example according to a process described in "Japanese patent application Kai No. Hei 4-501575, pages 7–9", wherein $CCl_4$ and HF are reacted with a phenol.

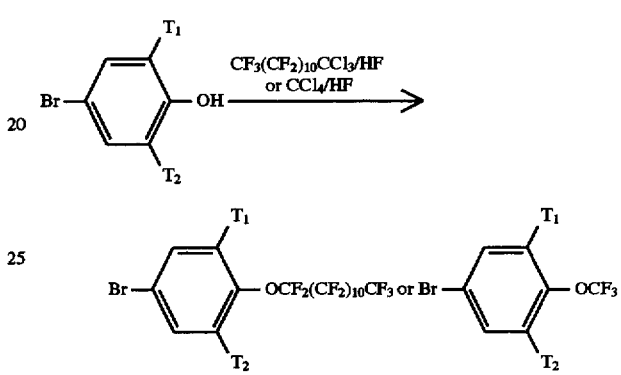

A case where Q—Y represents perfluoroalkyl group:

The compound of this case can be prepared according to a known process, for example according to a process described in "Fourth edition, Lecture of Experimental Chemistry, 19, page 403", wherein copper powder is reacted with a perfluorohalide as a perfluoroalkylating agent in an aprotic solvent, followed by reacting an iodobenzene derivative with the resulting solution of $CF_3$.Cu complex.

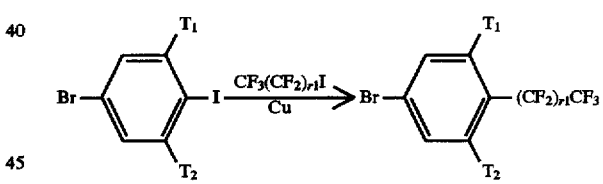

Further, according to a process described in "Fourth edition, Lecture of Experimental Chemistry, 19, page 390", a preferable result is also obtained by treating a carboxylic acid with $SF_4$. In addition, as the perfluoroalkylating agent, besides the above, $CF_3CO_2Na$, $FO_2SCF_2CO_2Me$, n-$Bu_4N^+$ $H_2F_3^-$, $CF_3SiMe_3$, $CF_2Br_2$, etc. can be preferably used.

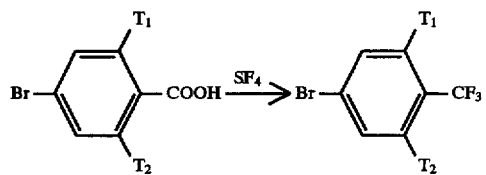

A case where Q—Y represents a fluoroalkoxy group containing hydrogen atom(s):

In this case, the objective compound can be preferably prepared according to a known process, for example by using an unsaturated fluoroalkene. For example, it is possible to produce a fluoroalkoxy site containing hydrogen atom(s), using hexafluoropropene or tetrafluoroethylene, as follows:

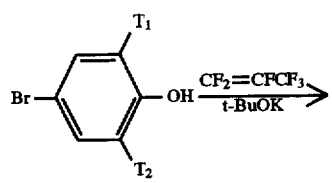

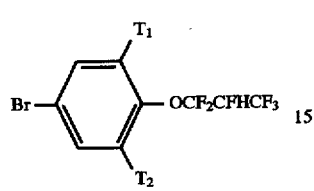

Further, it can also be prepared by carrying out etherification reaction using a fluoroalkylhalide e.g. a fluoroalkyliodide, under basic condition:

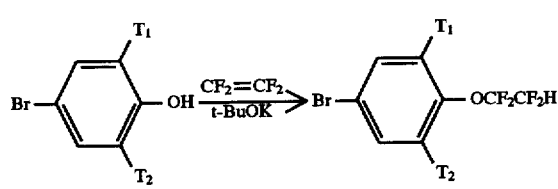

A case where Q—Y represents a fluoroalkyl group containing hydrogen atom(s):

In this case, the compound can be prepared for example by treating a benzaldehyde derivative with diethylaminosulfur trifluoride (DAST), as described in "J.O.C., 40, 578 (1975), or by treating it by ultrasonic wave in the presence of a fluoroalkyl iodide and zinc, followed by treating the resulting material with DAST, as described in "Organosynthetic Chemistry, Vol. 41, No. 5, page 53", or by reacting a fluoroalkyl iodide with a phenyllithium derivative according to a known process:

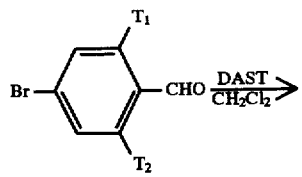

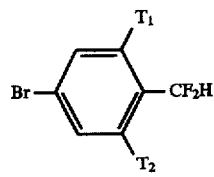

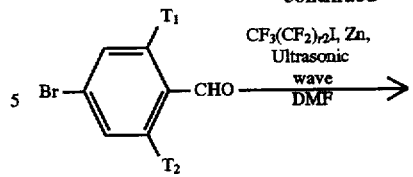

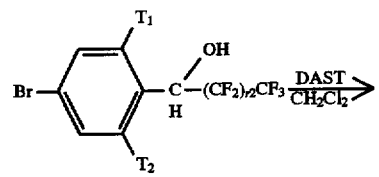

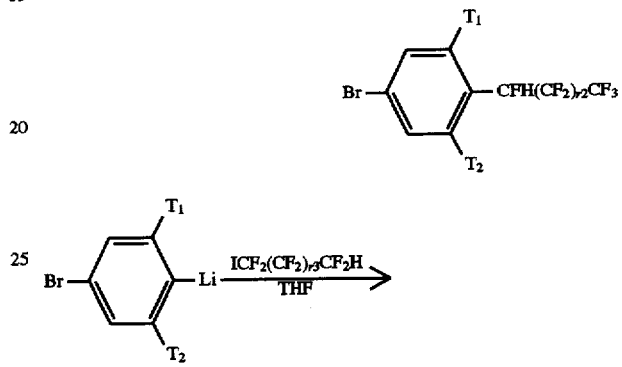

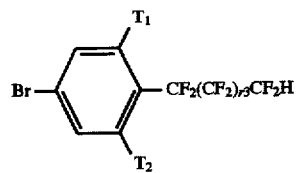

Synthesis of the compound of the present invention:

Using the compounds having Q—Y group introduced as described above or a commercially available fluorine-substituted-phenyl derivative, it is possible to prepare the compound of the present invention, for example, representative compounds shown in the formulas (1-1) to (1-25):

Firstly, preparation processes of bicyclic or tricyclic compounds will be described.

Compound of the formula (1-1):

The hydroxyl group of a normal alkane derivative substituted by hydroxyl group and a halogen such as bromine at both the respective ends is protected, followed by reacting the resulting compound with Mg in an aprotic solvent such as ether or tetrahydrofuran (hereinafter abbreviated to THF), at a temperature of −50° C. to room temperature, to obtain a Grignard agent, reacting this agent with a bromobenzene derivative (6) in the presence of a catalyst such as Ni acetylacetonate and then deprotecting to prepare an alcohol derivative (7), and reacting this derivative (7) with DAST in a solvent such as chloroform, dichloromethane, etc. at a temperature of −50° C. to the boiling point of the solvent, to prepare a fluoroalkyl derivative (8). With this derivative, alkyl lithium like butyl lithium etc. is reacted in THF, at a temperature of −50° C. to room temperature, to prepare compound (9). However, in the case where the benzene derivative (6) is bromobenzene, lithio-derivative reaction of (8) to (9) does not advance preferably. Thus, it is preferred that bromine is reacted with the compound (8) in the presence of a catalyst such as aluminum chloride, etc. to once prepare 4-(ω-fluoroalkyl)bromobenzene, followed by subjecting this compound to lithio-derivation to obtain com-

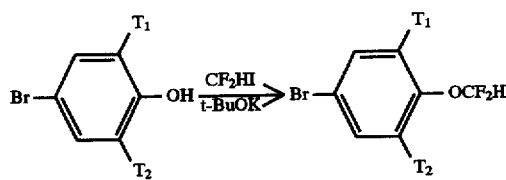

pound (9). The thus obtained compound (9) is reacted with zinc chloride in THF at a temperature of −50° C. to room temperature, to prepare compound (10). To a THF solution of this compound (10) is added tetrakistriphenylphosphine palladium as a catalyst, followed by dropwise adding a bromobenzene derivative (11), stirring the mixture at room temperature or refluxing it, and recrystallizing to obtain compound (1-1).

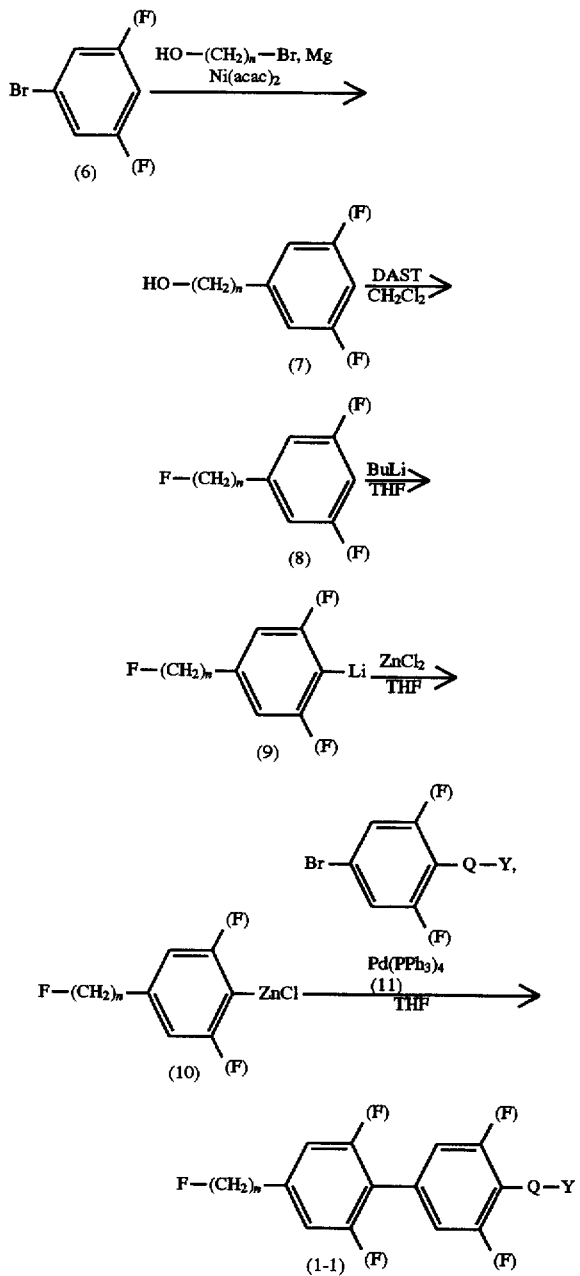

Compound of the formula (1-2):

Firstly, a Grignard reagent (hereinafter referred to as (11)-Mg) obtained from the above bromobenzene derivative (11) as raw material is prepared in an aproic solvent such as ether, THF, etc. at a temperature of −50° C. to room temperature, followed by dropwise adding ethylene oxide to the resulting product at the above temperature, to obtain a phenetylalcohol derivative (12), and reacting this derivative with a brominating reagent such as HBr, tribromophosphine, etc., to prepare a phenetyl bromide derivative (13). On the other hand, iodine is reacted with the above compound (9) in THF, to prepare a compound (14), followed by adding this compound to a Grignard reagent (13)-Mg prepared by using the above phenetyl bromide derivative (13) in an aproic solvent such as ether, THF, etc., and reacting the mixture in the presence of a catalyst such as Ni acetylacetonate, etc. at a temperature of −50° C. to room temperature, to prepare compound (1-2).

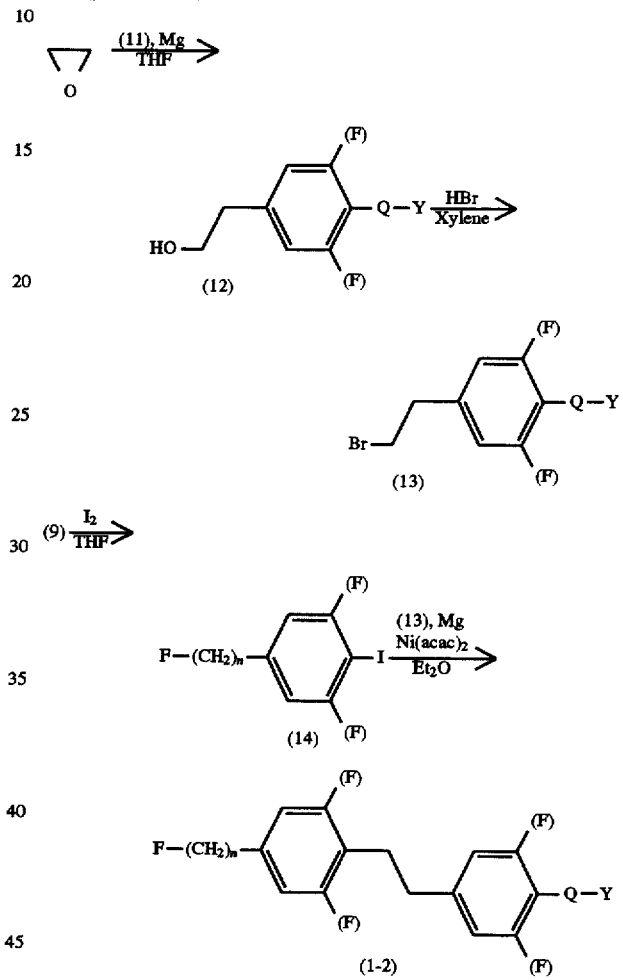

Compound the formula (1-3) or (1-5):

Bromine is reacted with the above compound (9) in THF, to prepare compound (15). But, in the case where 4-(ω-fluoroalkyl)bromobenzene is prepared, the fluoroalkyl derivative (8) is brominated in the presence of a catalyst such as aluminum chloride, etc. to obtain compound (15). Thereafter, a Grignard reagent of the thus obtained compound (15) is prepared, followed by reacting the reagent with cyclohexanedione monoethylene ketal in THF, a temperature of 0° C. to room temperature, to prepare an alcohol derivative (17), reacting this compound (17) with ion-exchange resin or an organic acid such as paratoluene-sulfonic acid, to carry out dehydration reaction and thereby prepare a cyclohexene derivative (18). This derivative (18) is subjected to catalytic hydrogenetion in the presence of a heterogeneous catalyst such as Pd/C, Raney Ni, etc. to prepare a compound (19). The protective group of the compound (19) is removed by reacting with an acid. The thus obtained compound (20) is reacted with a Grignard reagent (11)-Mg or (13)-Mg prepared in an aproic solvent such as ether, THF, etc., followed by carrying out dehydration and catalytic hydrogenation in the same manner as the reaction from the above compound (17) to (19), and further carrying out purification procedure such as recrystallization, etc., to obtain compound (1-3) or (1-5).

Next, compound (1-4) or (1-9) can be obtained in the same manner as in the process of obtaining compound (1-3) or (1-5), except that compound (15) is replaced by its derivative (22).

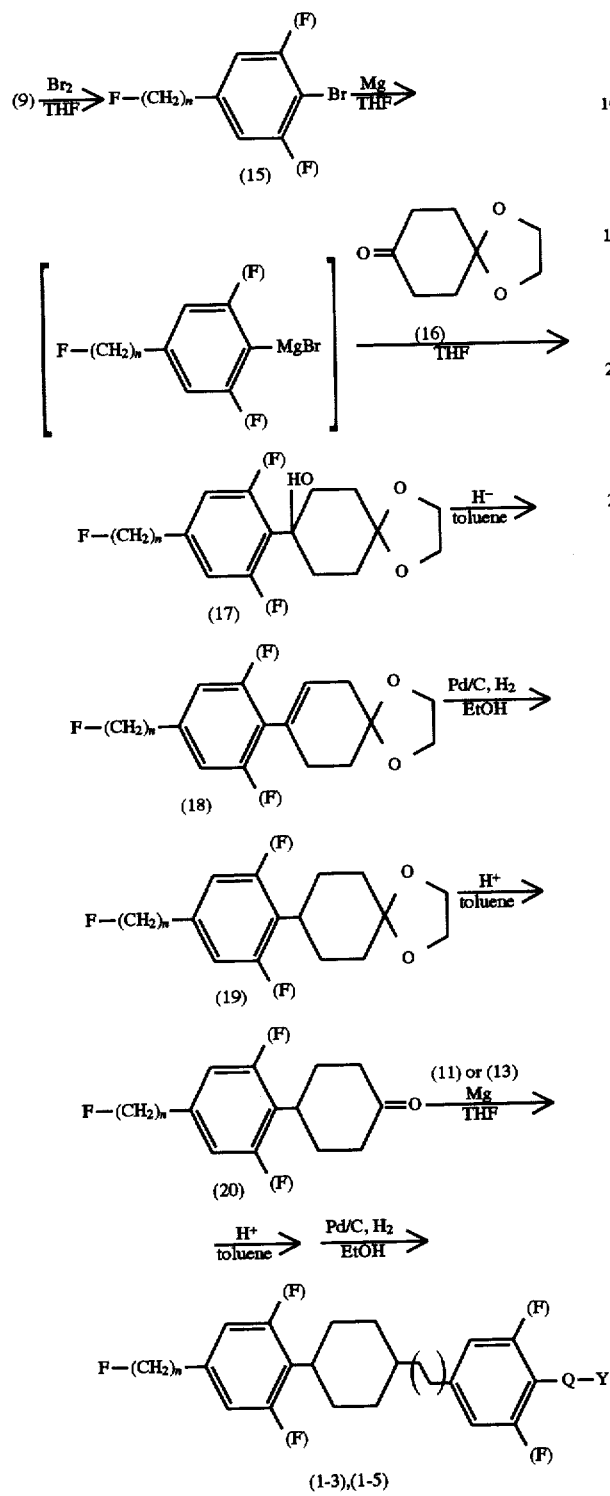

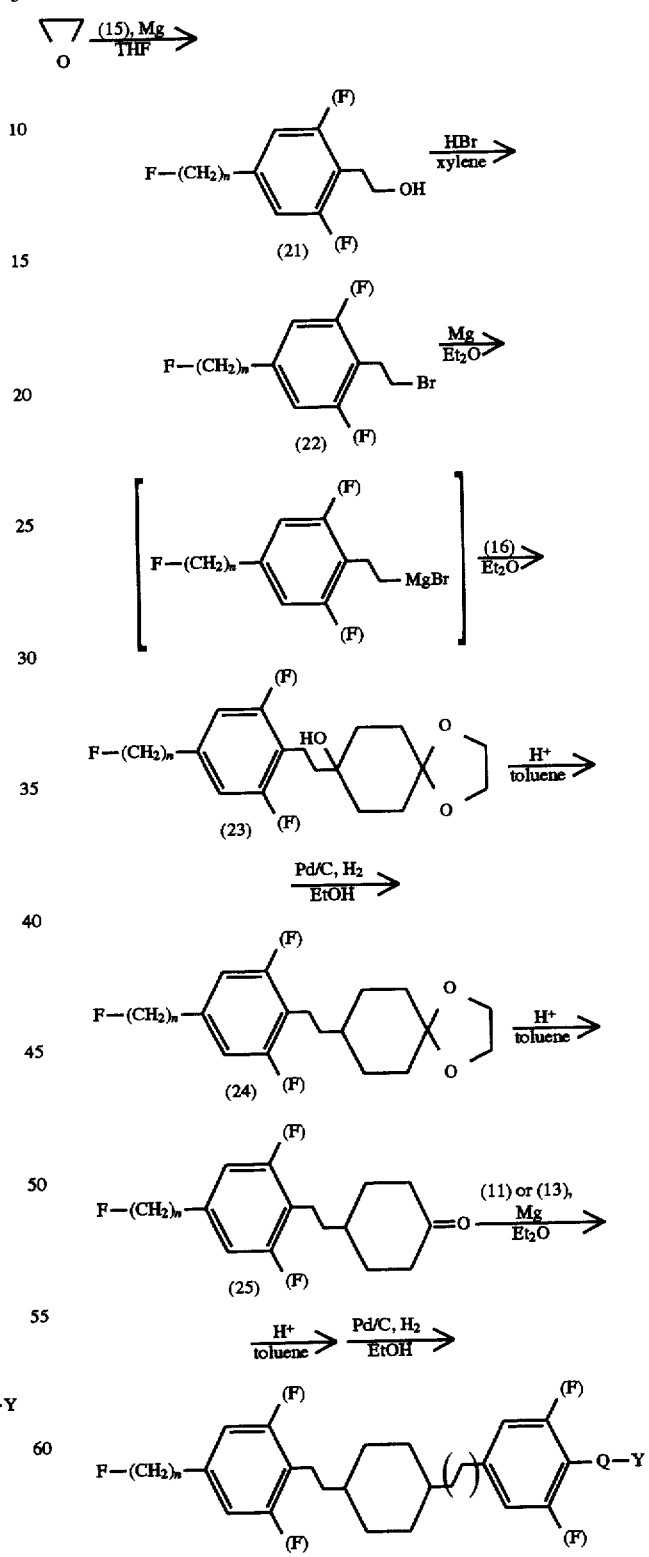

Compounds of formula (1-4) or (1-9):
A phenetylbromide derivative (22) is prepared in the same manner as in the process of obtaining compound (1-2), except that compound (11) is replaced by compound (15).

Compound of formula (1-6):

To a THF solution of the above compound (10) is added tetrakistriphenylphosphine palladium as a catalyst, followed by dropwise adding the above bromobenzene derivative (6), stirring the mixture at room temperature or refluxing, to obtain compound (26). Compound (1-6) can be obtained in the same manner as in the process of obtaining compound (1-1) except that compound (8) is replaced by compound (26).

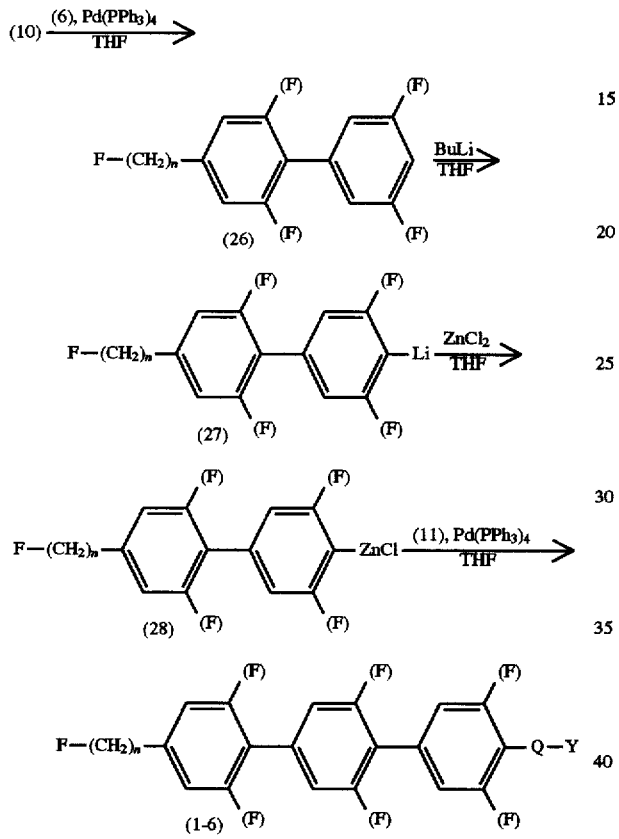

Compound of formula (1-7):

A Grignard reagent obtained using the above bromobenzene derivative (6) as a raw material is prepared in an aproic solvent such as ether, THF, etc. at a temperature of −50° C. to room temperature, followed by dropwise adding thereto ethylene oxide at the same temperature, to obtain a phenetyl alcohol derivative (29), reacting this derivative (29) with a brominating reagent such as HBr, tribromophosphine, etc. to obtain a phenetyl bromide derivative (30), preparing a Grignard reagent thereof in an aproic solvent such as ether, THF, etc. at a temperature of −50° C. to room temperature, and reacting the agent with the above compound (15) in the presence of a catalyst such as Ni acetylacetonate, to obtain compound (31). Compound (1-7) can be obtained in the same manner as in the process of obtaining compound (1-1), except that compound (8) is replaced by compound (31).

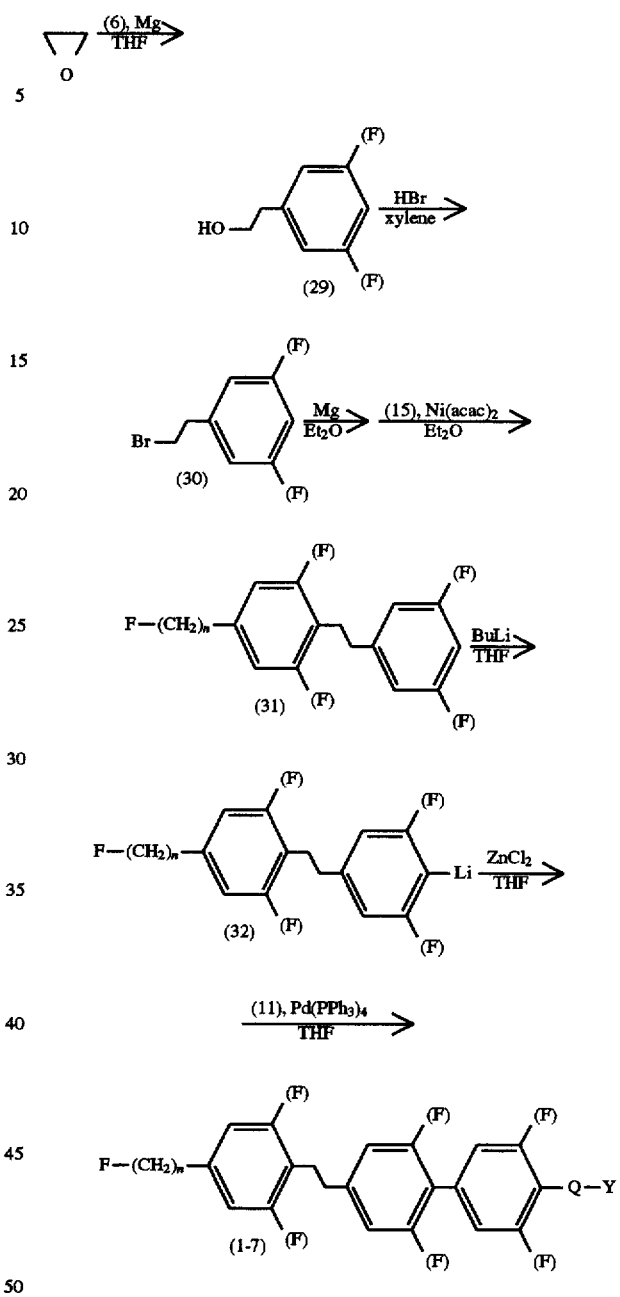

Compounds of the formula (1-8) or (1-10):

Bromine is reacted with the above compound (27) or (32) in THF, or bromine is reacted with the above compound (26) or (31) in the presence of aluminum chloride, etc., to prepare compound (33) or (34), followed by reacting therewith a Grignard reagent of the above compound (13) prepared in an aproic solvent such as ether THF, etc. at a temperature of −50° C. to room temperature, in the presence of a catalyst such as Ni acetyl acetonate, etc., to obtain compound (1-8) or (1-10).

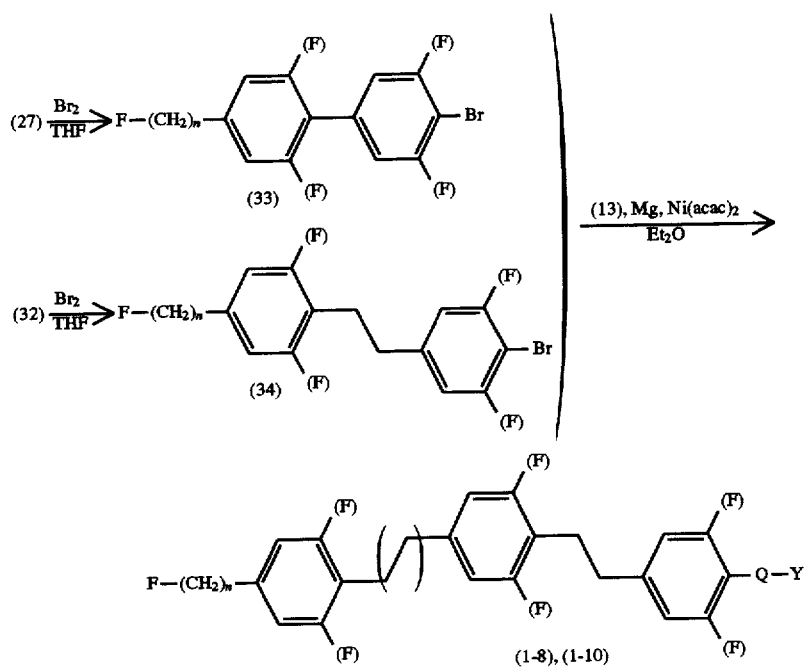

Compound of formula (1-11):

Compound (35) obtained from 4-(2-(4-oxocyclohexyl)ethyl)cyclohexanone is subjected to Wittig reaction using a suitable phosphonium salt, to prepare compound (36), followed by hydrogenating it in the presence of a heterogeneous catalyst such as Raney Ni, Pd/C, etc., to obtain compound (37). This compound is treated in the same manner as in the process of obtaining compound (1-4), except that compound (24) is replaced by compound (37), to obtain compound (1-11).

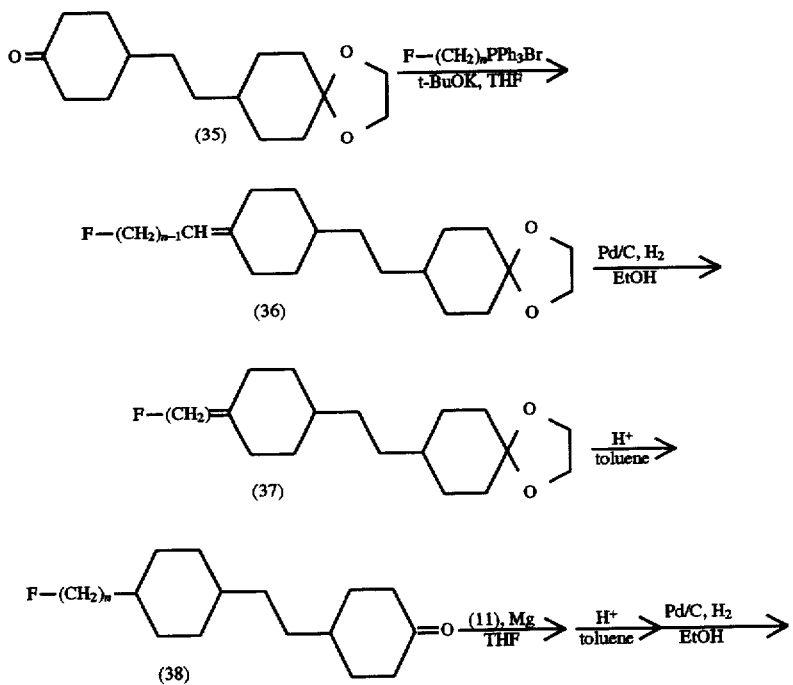

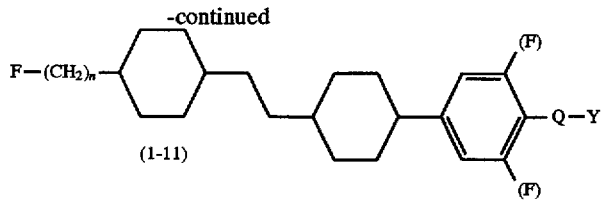

(1-11)

Compound of formula (1-12):

Compound (39) is prepared in the same manner as in the process of obtaining compound (1-11), except that the above compound (35) is replaced by compound (16), followed by reacting the compound (35) with a Grignard reagent of the above compound (30) prepared in an aproic solvent such as ether, THF, etc. at a temperature of −50° C. to room temperature, at the same temperature, successively carrying out dehydration reaction and hydrogenation reaction, to prepare compound (40). Compound (1-12) is obtained in the same manner as in the process of obtaining compound (1-1), except that compound (8) is replaced by compound (40).

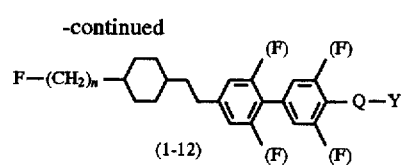

(1-12)

Compound of formula (1-13):

Compound (43) is prepared in the same manner as in the process of obtaining compound (1-11), except that the above compound (35) is replaced by compound (42). Compound (1-13) is obtained in the same manner as in the process of obtaining compound (1-5), except that the above compound (20) is replaced by compound (43).

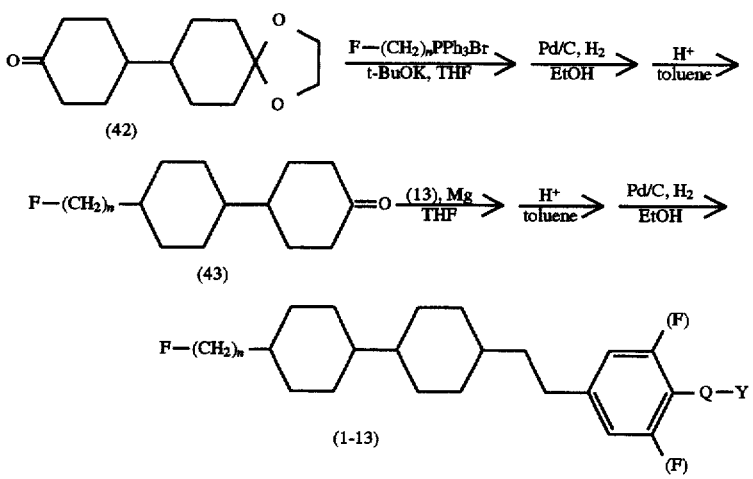

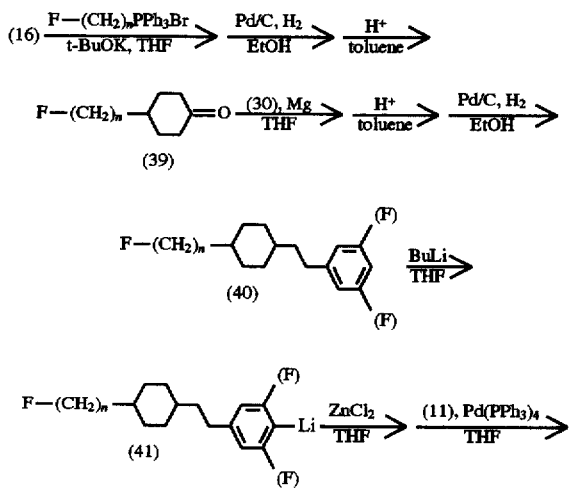

Compound of formula (1-14):

The above cyclohexanone derivative (39) is reacted with a Grignard reagent of the above compound (6) prepared in an aproic solvent such as ether, THF, etc. at a temperature of −50° C. to room temperature, at the same temperature, followed by successively carrying out dehydration reaction and hydrogenation, to prepare compound (44), reacting this compound with an alkyllithium such as butyllithium, etc. in THF at a temperature of −50° C. to room temperature, to prepare compound (45), reacting this compound with bromine in THF, to obtain compound (46). However, in the case where compound (44) is a 1-fluoroalkyl-4-phenylcyclohexane, it is preferred that bromine is reacted therewith in the presence of a catalyst such as aluminum chloride, to prepare compound (46). Compound (1-14) can be obtained in the same manner as in the process of obtaining compound (1-8), except that compound (33) is replaced by compound (46).

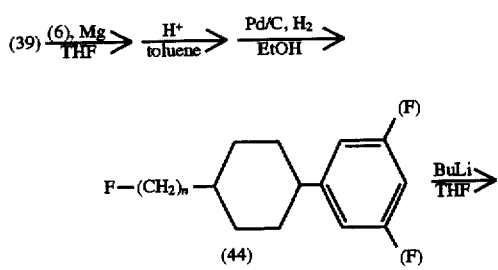

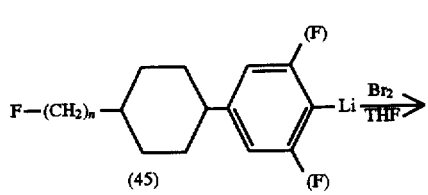

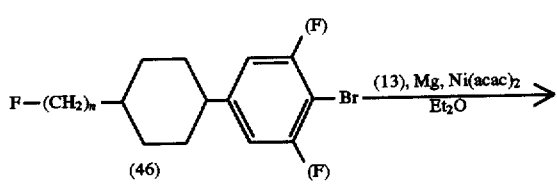

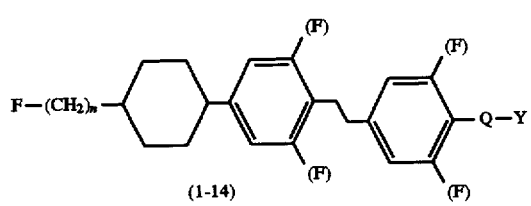

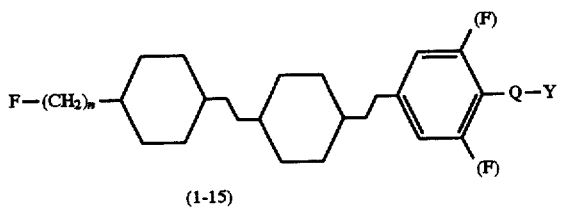

Compound of formula (1-15):

Compound (1-15) can be obtained in the same manner as in the process of obtaining compound (1-5), except that the above compound (20) is replaced by the above cyclohexanone derivative (38).

Compound of formula (1-16):

Bromine is reacted with the above compound (41) in THF, or compound (40) is brominated in the presence of a catalyst such as aluminum chloride, etc., to prepare compound (47). Compound (1-16) can be obtained in the same manner as in the process of obtaining compound (1-10), except that the above compound (33) is replaced by compound (47).

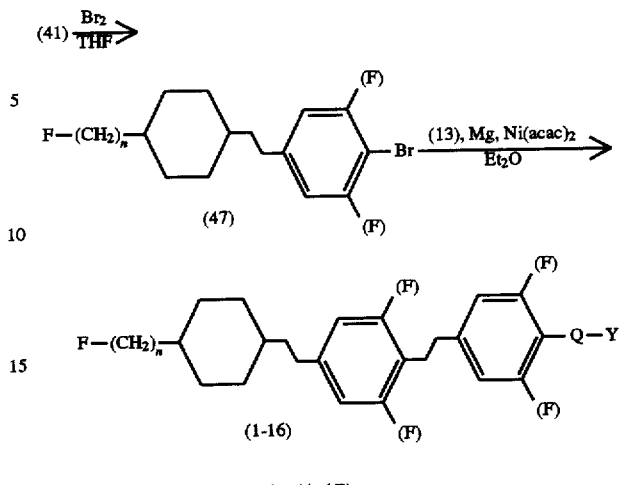

Compound of formula (1-17):

Compound (1-17) can be obtained in the same manner as in the process of obtaining compound (1-5), except that the above compound (20) is replaced by the above cyclohexanone derivative (39).

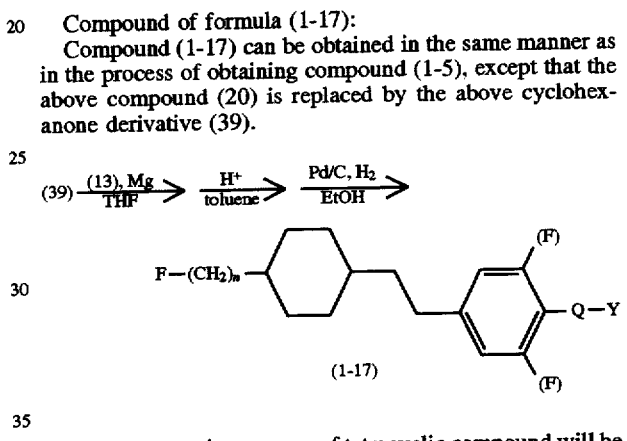

Next, preparation process of tetracyclic compound will be described.

In addition, in the below description, when a lithio-deriving reagent such as alkyllithium, etc. is reacted in THF with the above compounds (44), (40), (26) or (31), or bromine is reacted therewith in the presence of a catalyst such as aluminum chloride, etc., followed by reacting the reaction product with a lithio-deriving reagent, the resulting compounds (45), (41), (27) or (32) are collectively referred to as Ar-Li, and the above cyclohexane derivatives (43), (38), (20) or (25) are collectively referred to as R=O.

Compounds of formula (1-19) to (1-21) or (1-24):

Firstly, using these compounds Ar—Li or R=O as starting materials, tetracyclic precursor compounds (49), (50), (51) or (52) are prepared. Namely, zinc chloride is reacted with Ar—Li in THF at a temperature of −50° C. to room temperature to prepare compound (48), followed by adding tetraxistriphenylphosphine palladium as catalyst to a THF solution of the compound (48), dropwise adding the above bromobenzene derivative (6) and stirring the mixture at room temperature or refluxing, to prepare compound (49).

Further, a Grignard reagent of compound (6) prepared in an aproic solvent such as ether, THF, etc. at a temperature of −50° C. to room temperature is reacted with a cyclohexanone derivative R=O, followed by successively carrying out dehydration reaction and hydrogenation, to prepare compound (50).

Further, a Grignard reagent of compound (30) prepared in an aproic solvent such as ether, THF, etc. at a temperature of −50° C. to room temperature is reacted with Ar—Li in the presence of a catalyst such as nickel acetylacetonate, etc., to prepare compound (51).

Further, a Grignard reagent of compound (30) prepared in an aproic solvent such as ether, THF, etc. at a temperature of −50° C. to room temperature is reacted with a cyclohexanone derivative R=O, followed by successively carrying out dehydration reaction and hydrogenation, to prepare compound (52).

An alkyllithium such as butyllithium is reacted with the precursor compounds (49) to (52) obtained above, in THF, to prepare compound (53), or bromine is reacted in a halide solvent such as methylene chloride in the presence of aluminum chloride to prepare compound (55), followed by reacting an alkyllithium such as butyllithium with the compound (55) in THF, to prepare compound (56). Compounds of (1-19) to (1-21) or (1-24) (in the case of m=0) can be obtained in the same manner as in the process of obtaining compound (1-1), except that compound (9) is replaced by compound (53) or (56).

In addition, when bromine is reacted with the above compound (53) in THF, it is possible to prepare (54). When the above phenetyl bromide derivative (13) is reacted with the compound (54) or the above compound (55) in an aproic solvent such as ether, THF, etc. at a temperature of −50° C. to room temperature and in the presence of a catalyst such as Ni acetylacetonate, etc., it is possible to prepare compounds (1-19) to (1-21) or (1-24) (in the case of m=1).

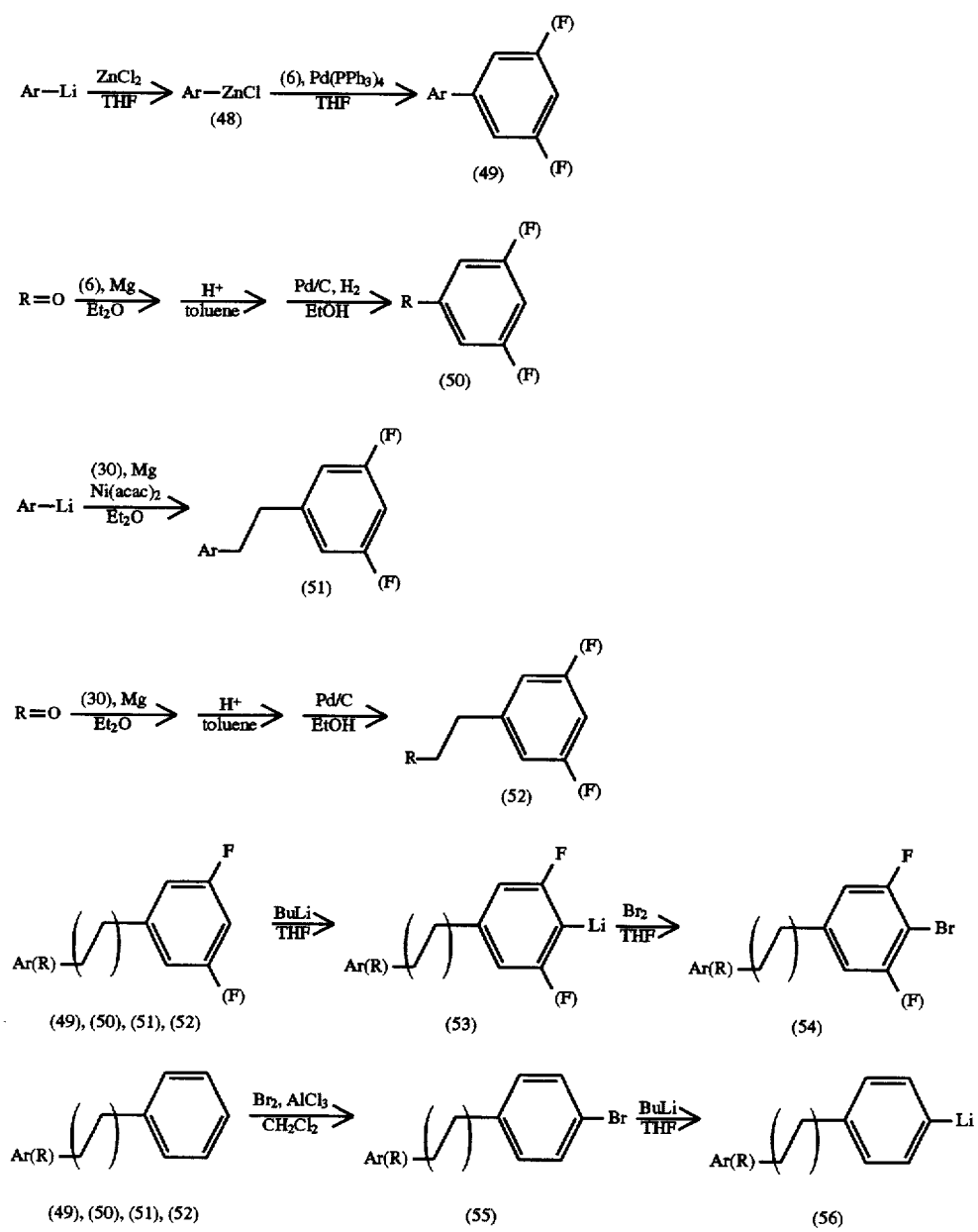

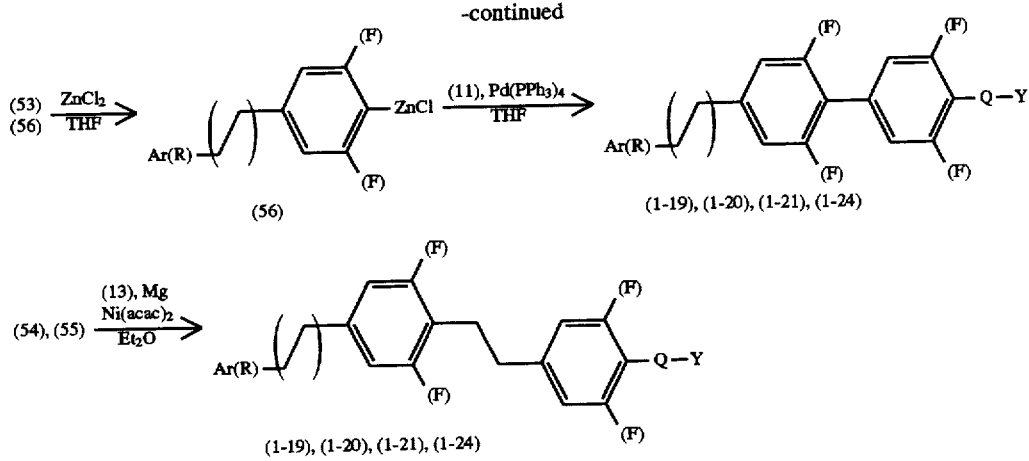

Compounds of formula (1-18), (1-12), (1-23), or (1-25):

Firstly, using the above Ar—Li or R=O as starting material, cyclohexane derivatives (58), (63), (68) or (73) as tetracyclic precursor compounds are prepared. Namely, the above cyclohexanedione monoethylene ketal (16) is reacted with Ar—Li in an aprotic solvent such as ether, THF, etc. at a temperature of −50° C. to room temperature, followed by successively carrying out dehydration with acid and hydrogenation reaction in the presence of a catalyst such as Raney Ni or Pd/C, to prepare compound (57). By removing the protective group of this compound (57), a cyclohexanone derivative (58) is obtained.

Further, a Grignard reagent of 4-methoxybromobenzene (59) is reacted with R=O, followed by successively carrying out dehydration with acid, and catalytic hydrogenation treatment in the presence of a catalyst of Pd/C, to prepare compound (60). This compound (60) is refluxed in the presence of an acid catalyst in toluene or xylene to obtain a phenol derivative (61), followed by nucleushydrogenating in the presence of Pd/C catalyst, to obtain a cyclohexanol derivative (62). In addition, in this reaction, even in the case where phenyl group is contained in R, benzene ring having hydroxyl group bonded is almost selectively hydrogenated. When the above cyclohexanol derivative (62) is oxydized with an oxydizing agent, cyclohexane derivative (63) is prepared.

Further, when ethylene oxide is reacted with Ar—Li, compound (64) is obtained, and when this compound is brominated with HBr or tribromophosphine, compound (65) is obtained. Next, when compound (16) is reacted with a Grignard reagent (66) of the compound (65), compound (67) is obtained. When the protective group of the compound is removed with an acid, a cyclohexanone derivative (68) is obtained.

Further, when a Grignard reagent of the above 4-methoxybromobenzene (59) is reacted with ethylene oxide, followed by brominating with HBr or tribromophosphine, compound (69) is obtained. A cyclohexanone derivative (73) is prepared in the same manner as in the reaction of preparing compound (63), except that compound (59) is replaced by compound (69).

A Grignard reagent of the above compound (11) or (13) is reacted with the above obtained precursor compounds (58), (63), (68) or (73), followed by successively carrying out dehydration with an acid and catalytic hydrogenation treatment in the presence of a catalyst such as Raney Ni, Pd/C, etc., to prepare compounds (1-18), (1-22), (1-23) or (1-25).

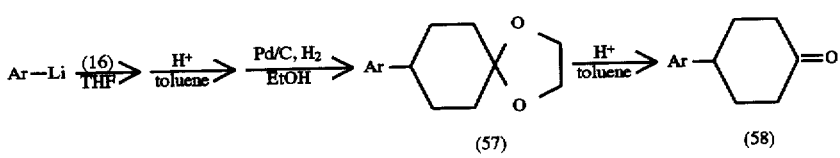

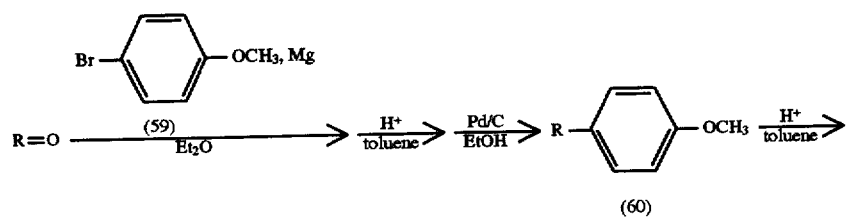

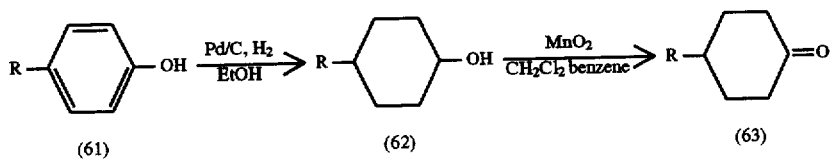

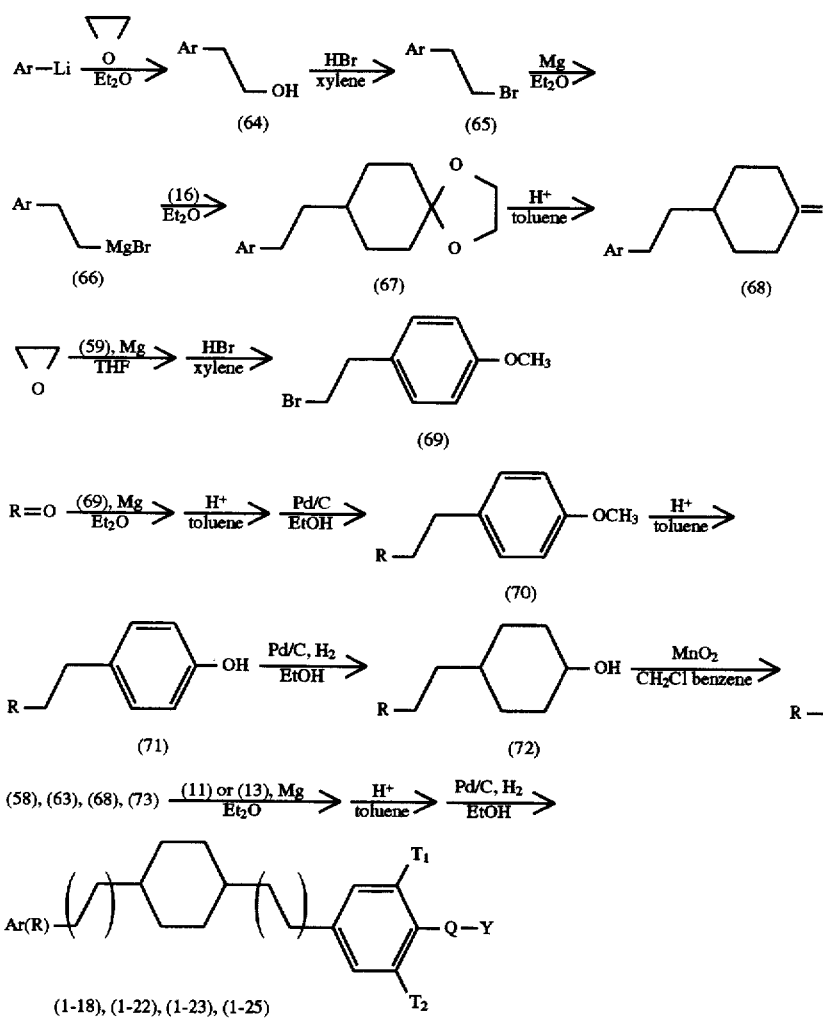

However, in the case where Q—Y represents $CF_2H$, $CF_2CF_2H$, $CF_2CFHCF_3$, $OCF_2H$, $OCF_2CFHCF_3$ or $OCF_2CF_2CF_2H$, in the liquid crystalline compound expressed by the formula (I) of the present invention, it is preferred to introduce ring Z—Q—Y site by the following route, differently from the above:

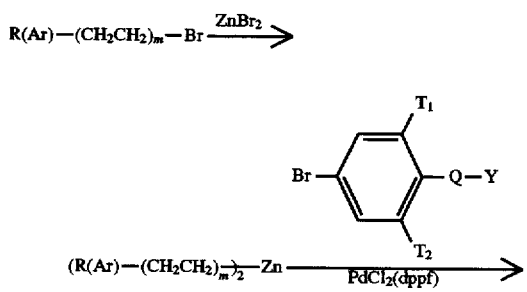

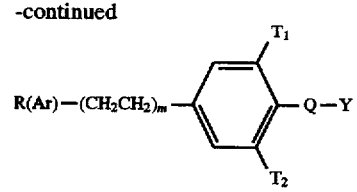

The liquid crystal composition provided by the present invention may be constituted by only a first component containing at least one member of the liquid crystalline compound expressed by the formula (I), but a blend of the first component and besides, as a second component, at least one member of compounds selected from the group consisting of the already mentioned formulas (II), (III) and (VI) (hereinafter referred to as the second component A) and/or at least one member of compounds selected from the group consisting of the formulas (V), (VI), (VII), (VIII) and (IX) (hereinafter referred to as the second component B) is preferred, and further, a known compound may be also blended as a third component, in order to adjust the threshold voltage, liquid crystal phase temperature range, $\Delta n$, $\Delta \epsilon$, viscosity, etc.

Among the second component A, the following (2-1) to (2-15) as preferable examples of compounds included in the formula (II), the following (3-1) to (3-48) as preferable examples of compounds included in the formula (III) and the following (4-1) to (4-41) as preferable examples of compounds included in the formula (IV), may be respectively mentioned:
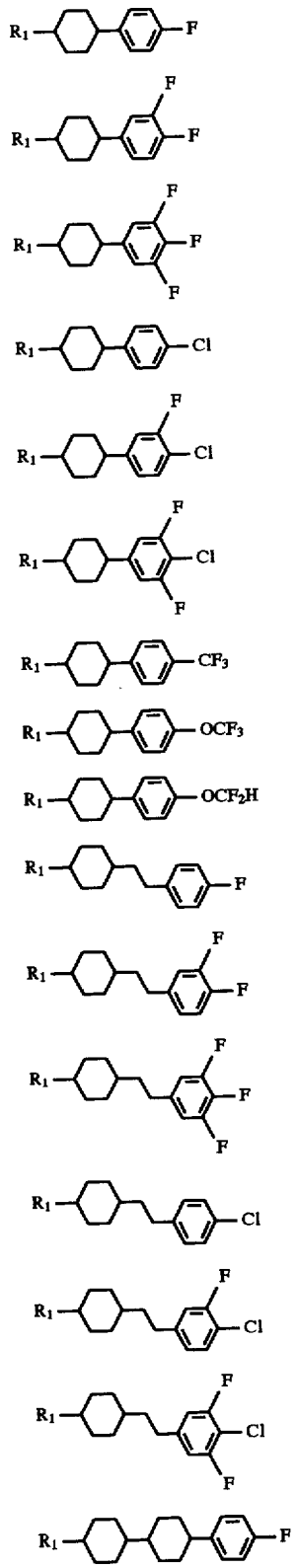
(2-1)
(2-2)
(2-3)
(2-4)
(2-5)
(2-6)
(2-7)
(2-8)
(2-9)
(2-10)
(2-11)
(2-12)
(2-13)
(2-14)
(2-15)
(3-1)
-continued
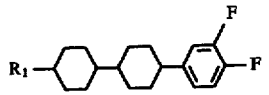  (3-2)
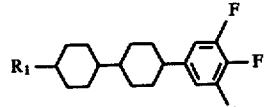  (3-3)
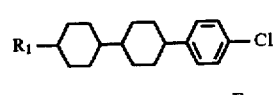  (3-4)
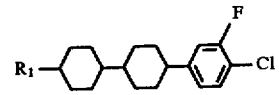  (3-5)
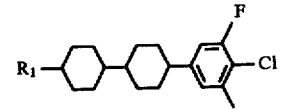  (3-6)
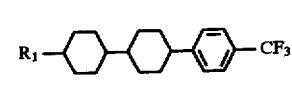  (3-7)
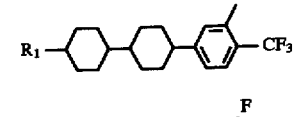  (3-8)
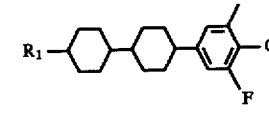  (3-9)
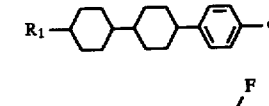  (3-10)
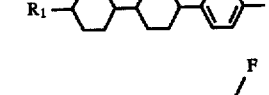  (3-11)
  (3-12)
  (3-13)
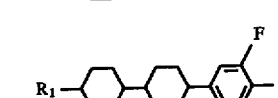  (3-14)
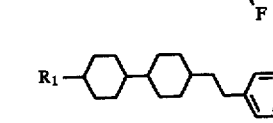  (3-15)
(3-16)

| | |
|---|---|
| (3-17) | (3-32) |
| (3-18) | (3-33) |
| (3-19) | (3-34) |
| (3-20) | (3-35) |
| (3-21) | (3-36) |
| (3-22) | (3-37) |
| (3-23) | (3-38) |
| (3-24) | (3-39) |
| (3-25) | (3-40) |
| (3-26) | (3-41) |
| (3-27) | (3-42) |
| (3-28) | (3-43) |
| (3-29) | (3-44) |
| (3-30) | (3-45) |
| (3-31) | (3-46) |

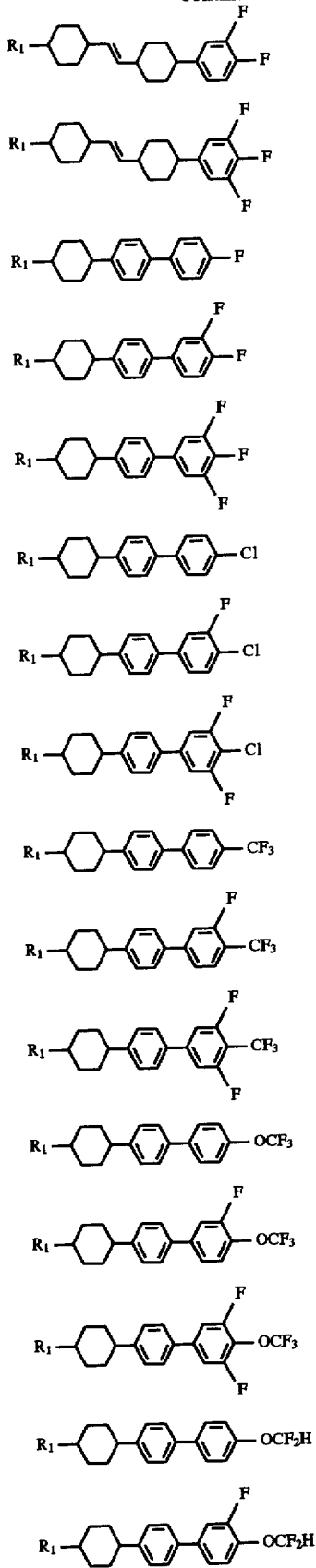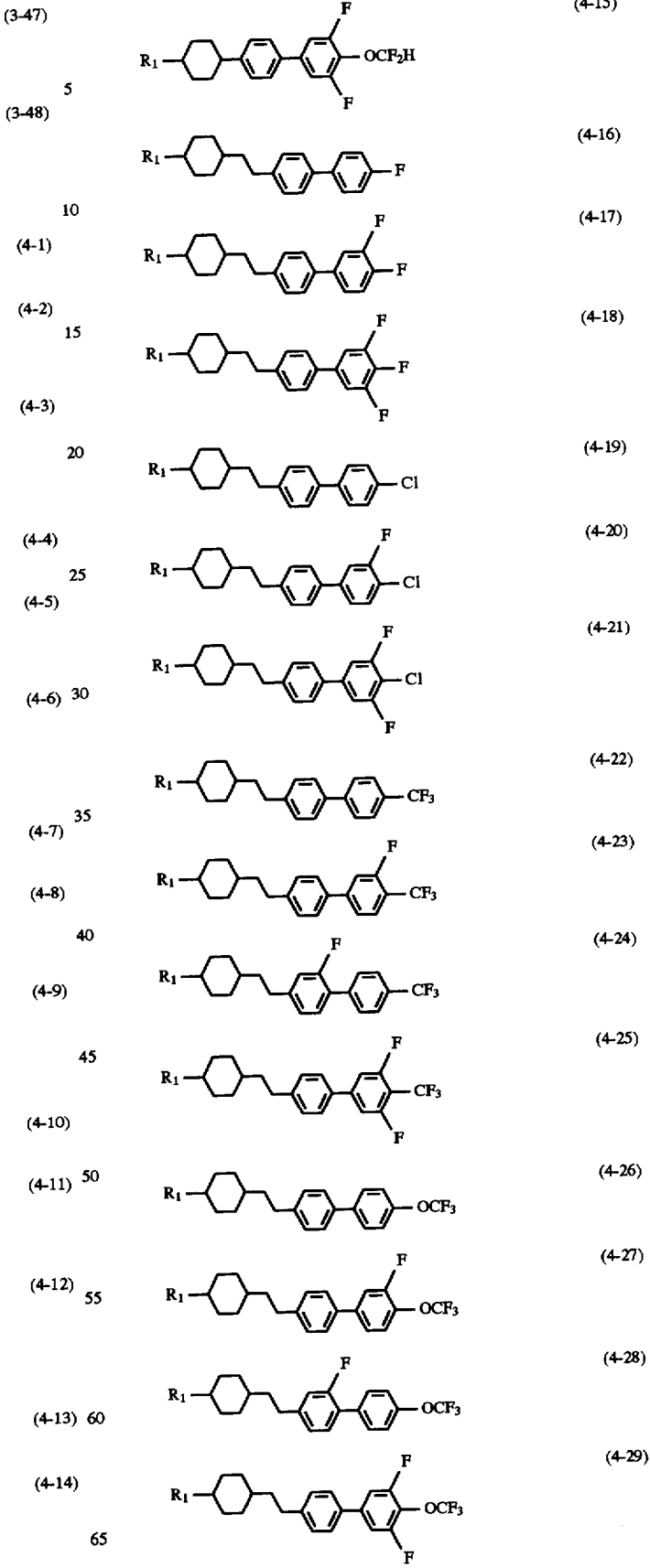

 (4-30)

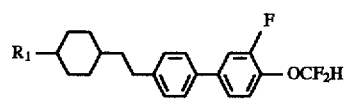 (4-31)

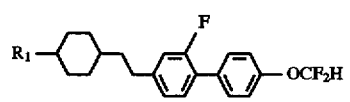 (4-32)

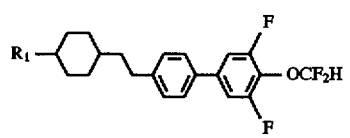 (4-33)

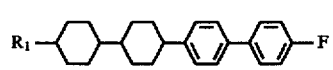 (4-34)

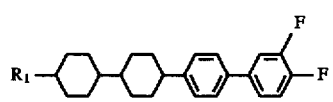 (4-35)

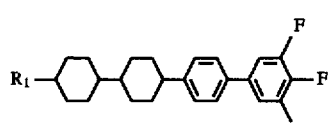 (4-36)

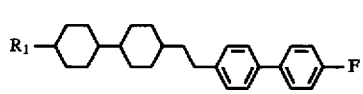 (4-37)

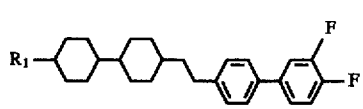 (4-38)

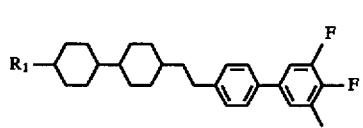 (4-39)

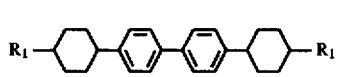 (4-40)

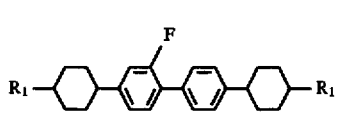 (4-41)

The compounds expressed by these formulas (II) to (IV) exhibit a positive Δε and are far superior in the heat stability and chemical stability.

As to the quantities of the compounds used, a range of 1 to 99% by weight based upon the total weight of the liquid crystal composition is suitable, and the range is preferably 10 to 97% by weight, more preferably 40 to 95% by weight.

Next, among the compounds of the above second component B, as preferable examples of compounds included in the formulas (V), (VI) and (VII), (5-1) to (5-27), (6-1) to (6-3) and (7-1) to (7-13) can be mentioned.

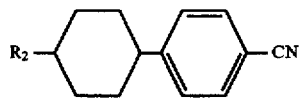 (5-1)

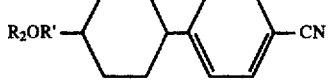 (5-2)

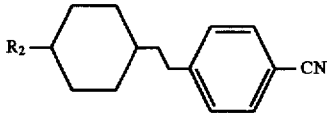 (5-3)

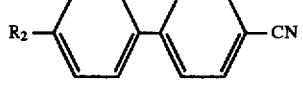 (5-4)

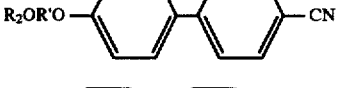 (5-5)

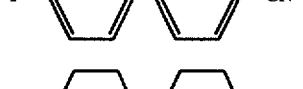 (5-6)

 (5-7)

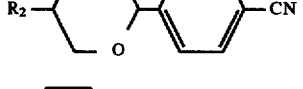 (5-8)

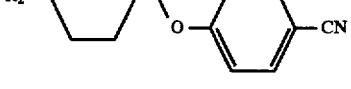 (5-9)

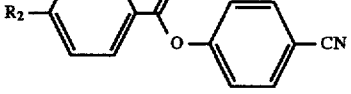 (5-10)

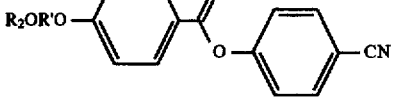 (5-11)

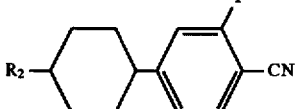 (5-12)

 (5-13)

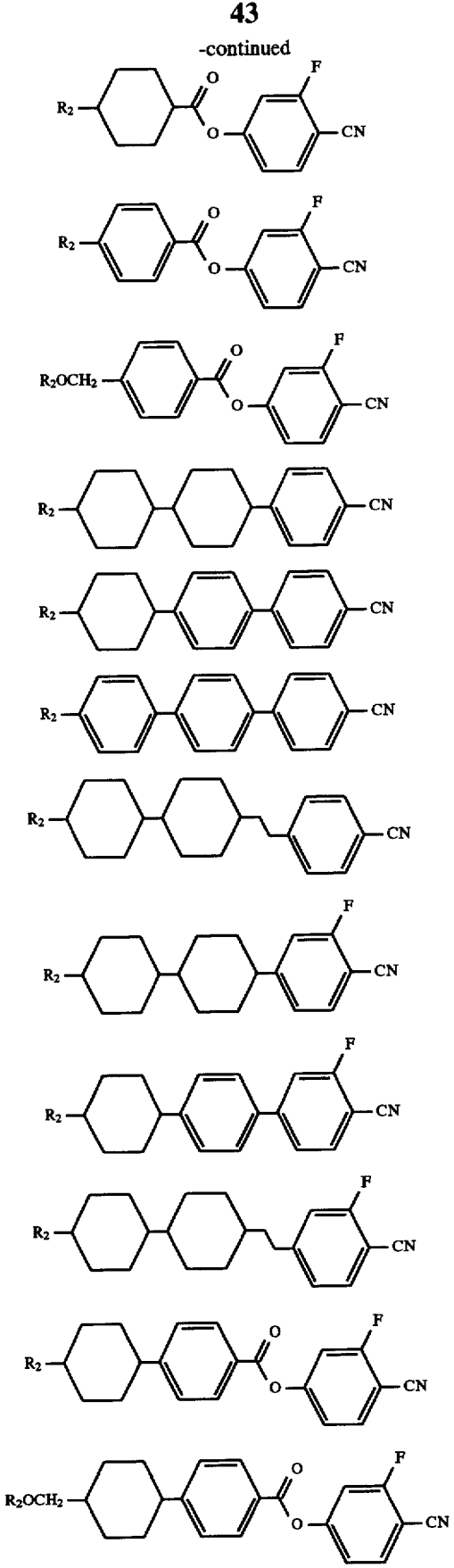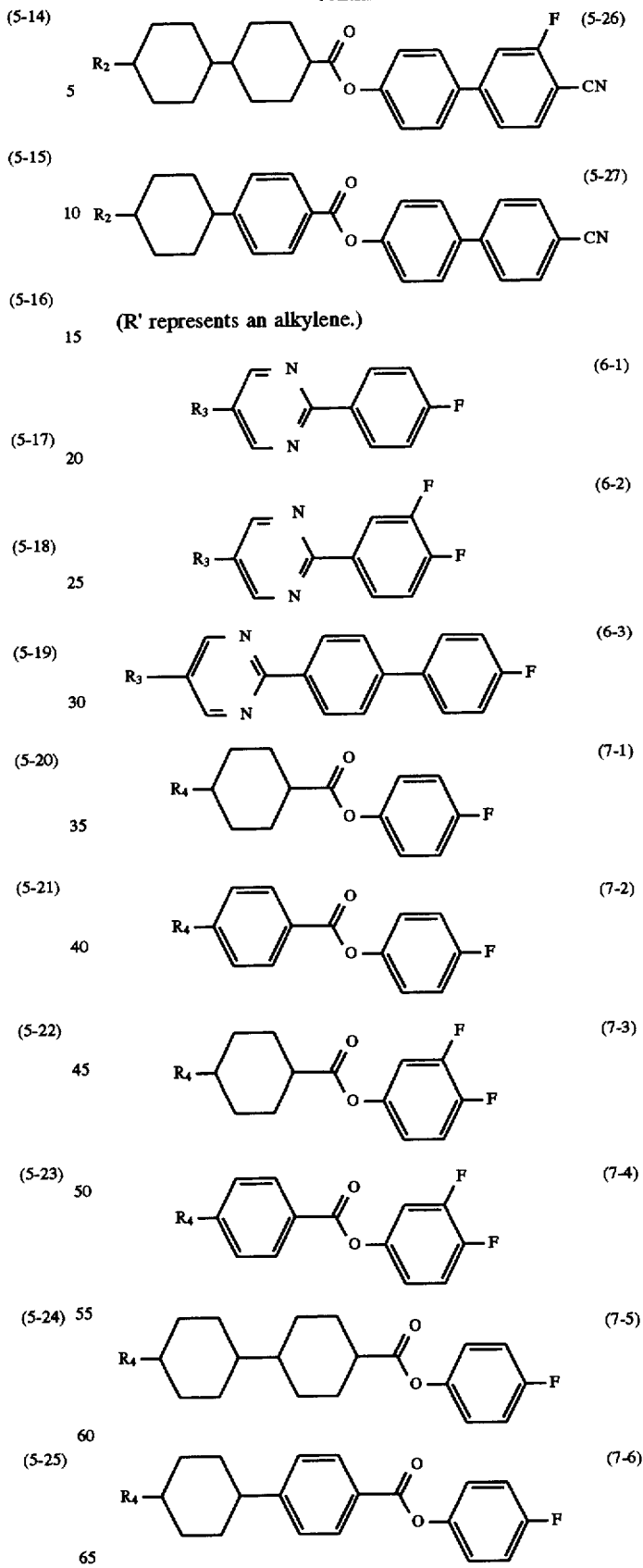
(R' represents an alkylene.)

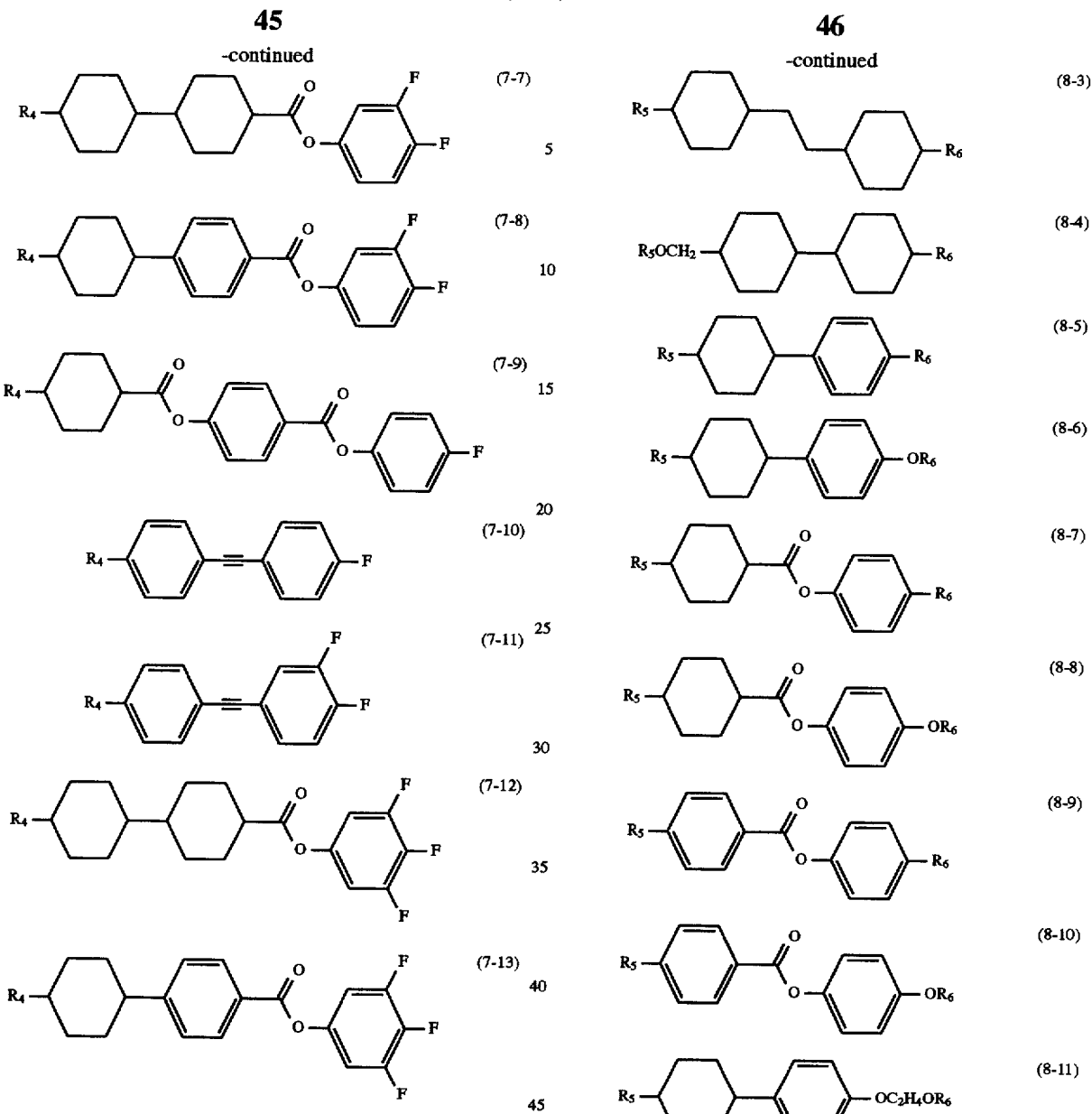

The compounds expressed by these formulas (V) to (VII) have a large positive Δε value; thus, they are used as a composition component particularly in order to lower the threshold voltage. Further, they are also used for adjusting the viscosity, adjusting the Δn, broadening the liquid crystal phase temperature range and so on, and further for improving the steepness.

Further, among the second component B, as preferable examples of compounds included in the formulas (VIII) and (IX), (8-1) to (8-15) and (9-1) to (9-14) are mentioned.

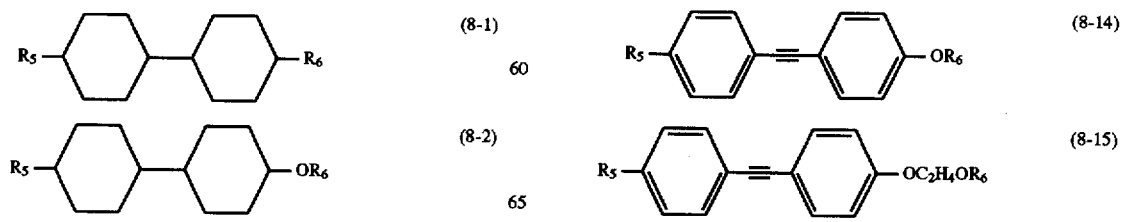

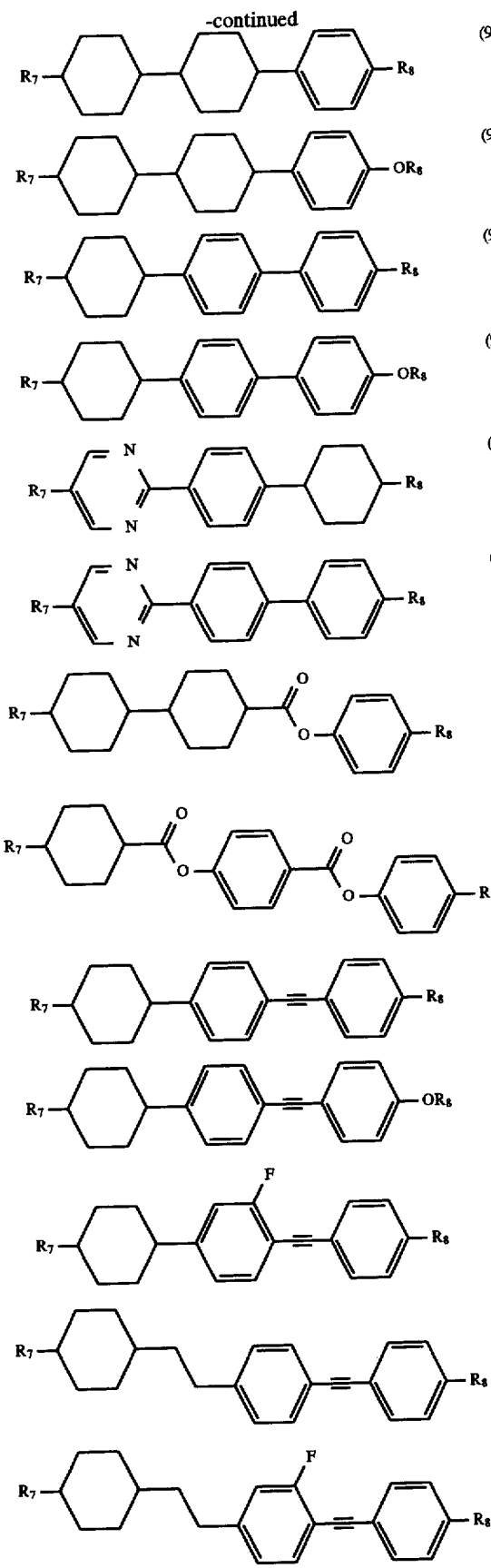

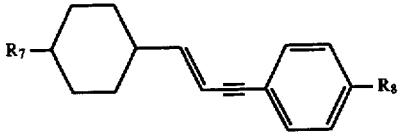

Compounds expressed by these formulas (VIII) and (IX) have negative or weakly positive Δε, and among these compounds, the compounds expressed by the formula (VIII) are used as composition components, mainly for lowering the viscosity and adjusting the Δn, and the compounds expressed by the formula (IX) are used for broadening the mesomorphic range and/or for adjusting the Δn.

Compounds expressed by the formulas (V) to (IX) are indispensable particularly in the case where a liquid crystal composition for STN mode display or conventional TN mode display are prepared. The quantity of the compounds used is suitable to be in the range of 1 to 99% by weight based upon the total weight of the liquid crystal composition when a liquid crystal composition for usual STN mode display or TN mode display is prepared, but the quantity is preferably in the range of 10 to 97% by weight, more preferably 40 to 95% by weight.

As to the liquid crystal composition provided by the present invention, it is preferred that the composition contains at least one member of the liquid crystalline compound expressed by the formula (I) in a ratio of 1 to 99% by weight, in order to exhibit superior characteristics.

The liquid crystal composition is generally prepared according to a process which is known, for example, according to a process of dissolving mutually various components at a high temperature, or other processes. Further, if necessary, by adding a suitable additive, improvement in accordance with objective use applications is made to perform optimization. Such an additive has been well known and described in literatures in details. Usually, a chiral doping agent or the like is added, which induces the spiral structure of liquid crystal to adjust necessary twist angle, thereby preventing reverse twist.

Further, by adding a dichroic dyestuff such as those of merocyanine group, styryl group, azo group, azomethine group, azoxy group, quinophthalone group, anthraquinone group, tetrazine group, etc., the composition can be also used as that for GH mode. The liquid crystal composition of the present invention can be used not only as those of NCAP mode prepared by microcapsulating nematic liquid crystal, polymer-dispersion mode liquid crystal display element (PDLCD) prepared by forming a three-dimensional, reticulated, polymer substance, for example, polymer network liquid crystal display element (PNLCD), but also as those of birefringence control (ECB) mode or DS mode.

As examples of the liquid crystal composition containing the compound of the present invention, the following can be mentioned, wherein compound numbers are the same as those shown in the below mentioned examples. Further, the double bond of 1,4-cyclohexylene and that in alkyl chain are all directed to a trans-form.

COMPOSITION EXAMPLE 1

(Compound No. 17)   10%

-continued

FC₃H₆—[Cy]—[Cy]—CH₂CH₂—[Ph]—OCF₃  9%
(Compound No. 19)

C₂H₅—[Cy]—[Cy]—[Ph](F,F)  10%

C₃H₇—[Cy]—[Cy]—[Ph](F,F)  10%

C₅H₁₁—[Cy]—[Cy]—[Ph](F,F)  10%

C₇H₁₅—[Cy]—[Ph](F,F)  7%

C₂H₅—[Cy]—CH₂CH₂—[Cy]—[Ph](F,F)  4%

C₃H₇—[Cy]—CH₂CH₂—[Cy]—[Ph](F,F)  2%

C₅H₁₁—[Cy]—CH₂CH₂—[Cy]—[Ph](F,F)  4%

C₂H₅—[Cy]—[Ph]—[Ph](F,F)  6%

C₃H₇—[Cy]—[Ph]—[Ph](F,F)  6%

C₅H₁₁—[Cy]—[Ph]—[Ph](F,F)  12%

C₃H₇—[Cy]—[Cy]—[Ph]—F  5%

C₃H₇—[Cy]—[Ph]—[Ph]—F  5%

COMPOSITION EXAMPLE 2

FC₂H₄—[Cy]—[Cy]—CH₂CH₂—[Ph]—OCF₃  7%
(Compound No. 17)

FC₃H₆—[Cy]—[Cy]—CH₂CH₂—[Ph]—OCF₃  7%
(Compound No. 19)

FC₃H₆—[Cy]—[Cy]—CH₂CH₂—[Ph]—CF₃  7%
(Compound No. 18)

-continued

C₇H₁₅—[Cy]—[Ph](F,F,F)  2%

C₂H₅—[Cy]—[Cy]—[Ph](F,F)  6%

C₃H₇—[Cy]—[Cy]—[Ph](F,F)  6%

C₅H₁₁—[Cy]—[Cy]—[Ph](F,F)  6%

C₂H₅—[Cy]—[Ph]—[Ph](F,F)  2%

C₃H₇—[Cy]—[Ph]—[Ph](F,F)  2%

C₅H₁₁—[Cy]—[Ph]—[Ph](F,F)  4%

C₃H₇—[Cy]—[Cy]—[Ph](F,F,F)  7%

C₃H₇—[Cy]—CH₂CH₂—[Cy]—[Ph](F,F,F)  7%

C₅H₁₁—[Cy]—CH₂CH₂—[Cy]—[Ph](F,F,F)  7%

C₃H₇—[Cy]—[Cy]—CH₂CH₂—[Ph](F,F,F)  7%

C₅H₁₁—[Cy]—CH₂CH₂—[Ph](F,F,F)  7%

C₃H₇—[Cy]—[Ph]—[Ph](F,F,F)  5%

-continued
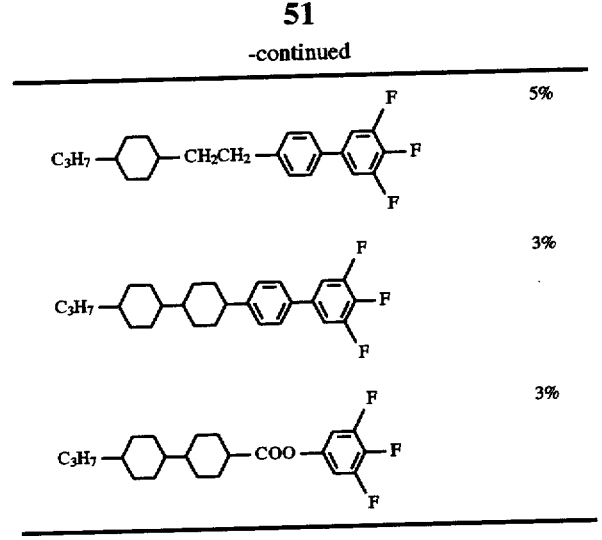
COMPOSITION EXAMPLE 3
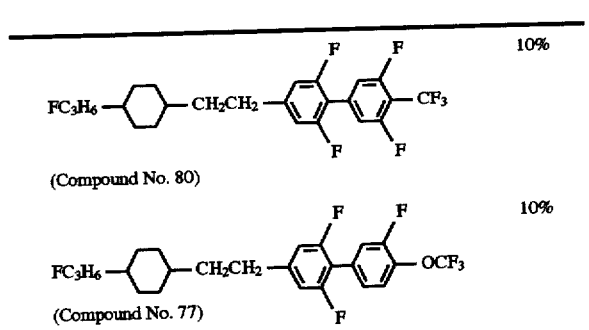
-continued
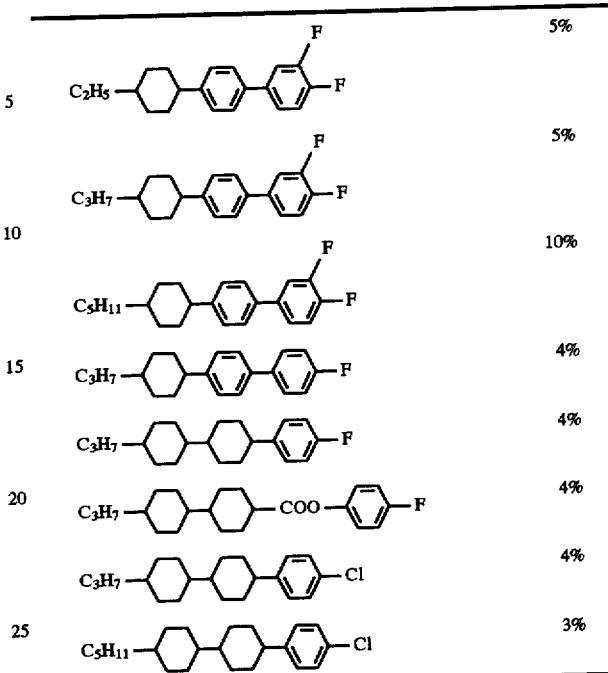
COMPOSITION EXAMPLE 4
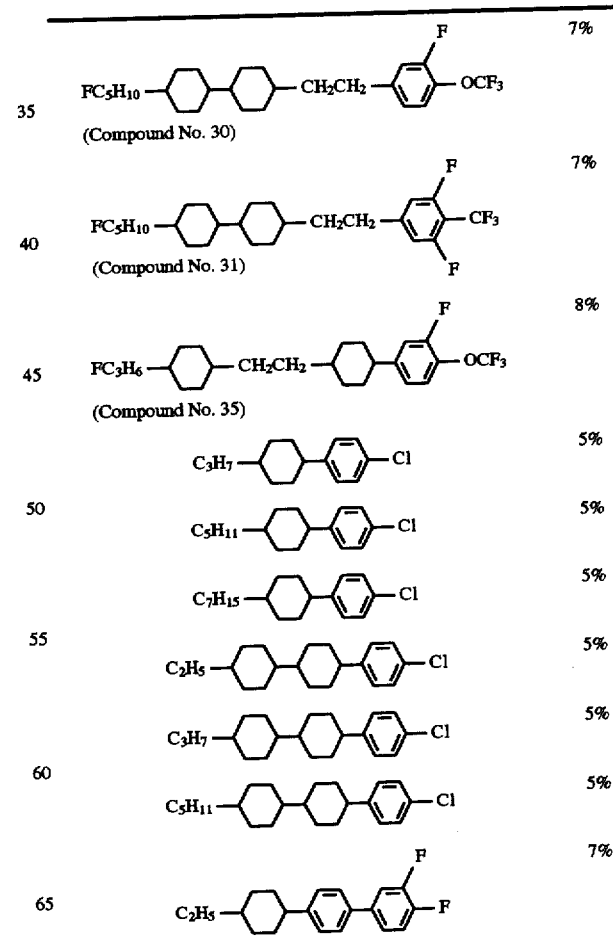

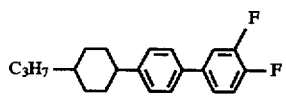 7%
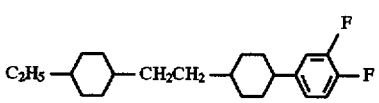 14%
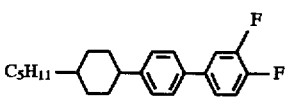 6%
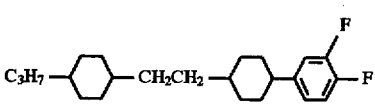 6%
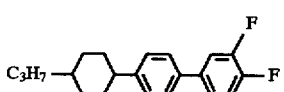 4%
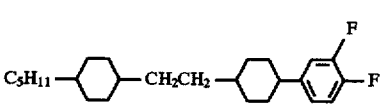 4%
COMPOSITION EXAMPLE 5
 6%
(Compound No. 125)
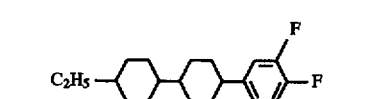 6%
(Compound No. 11)
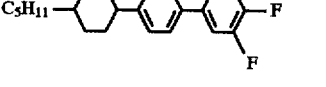 4%
(Compound No. 240)
 5%
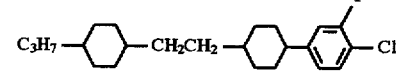 10%
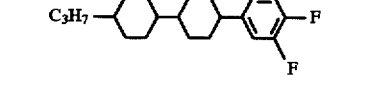 10%
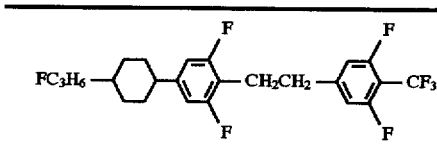 10%
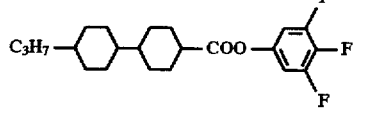 6%
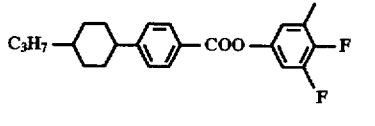 3%
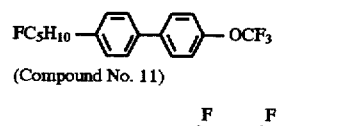 6%
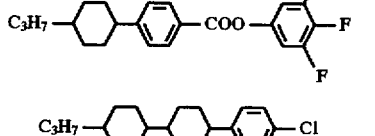 4%
 4%
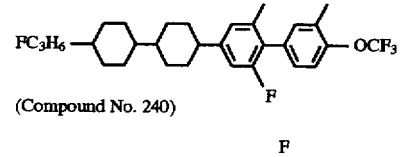 4%
 4%
 3%
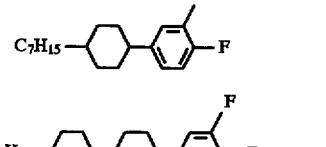 3%
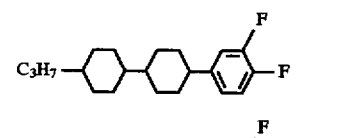 3%
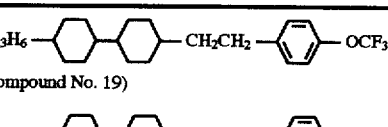 3%
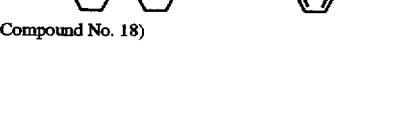 4%
C₃H₇—⟨cyclohexyl⟩—⟨cyclohexyl⟩—⟨phenyl⟩—OCH₃  4%
COMPOSITION EXAMPLE 6
FC₃H₆—⟨cyclohexyl⟩—⟨cyclohexyl⟩—CH₂CH₂—⟨phenyl⟩—OCF₃  6%
(Compound No. 19)
FC₃H₆—⟨cyclohexyl⟩—⟨cyclohexyl⟩—CH₂CH₂—⟨phenyl⟩—CF₃  5%
(Compound No. 18)

55
-continued
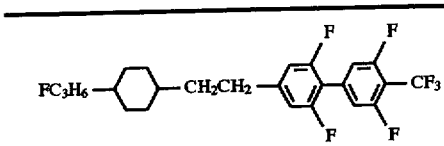 5%
(Compound No. 80)
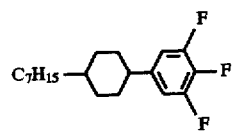 8%
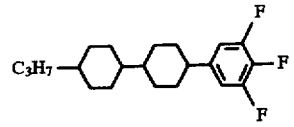 8%
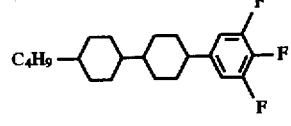 5%
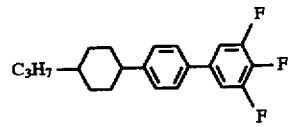 8%
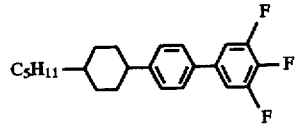 8%
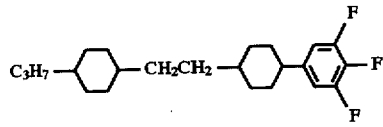 10%
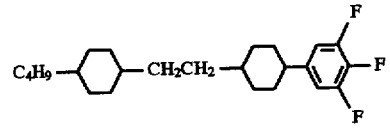 8%
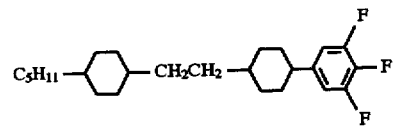 8%
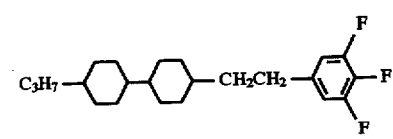 11%
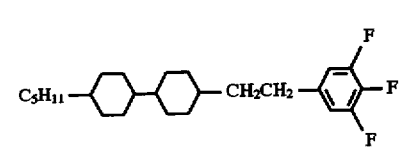 6%
56
-continued
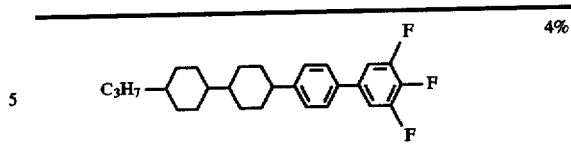 4%
COMPOSITION EXAMPLE 7
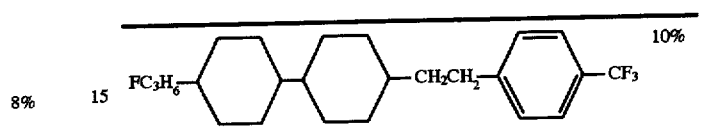 10%
(Compound No. 18)
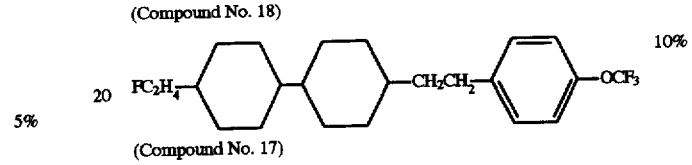 10%
(Compound No. 17)
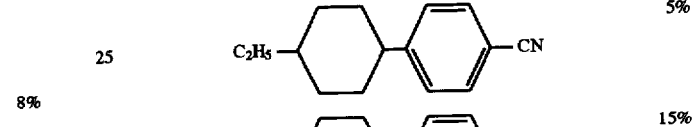 5%
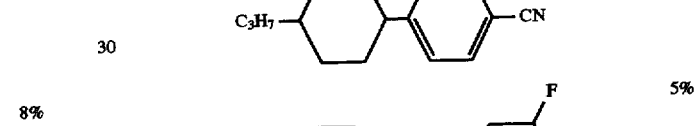 15%
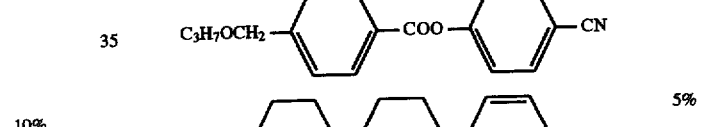 5%
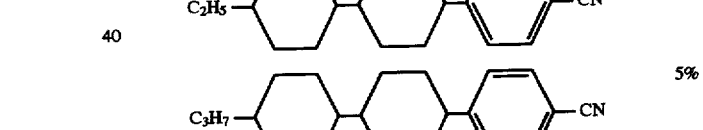 5%
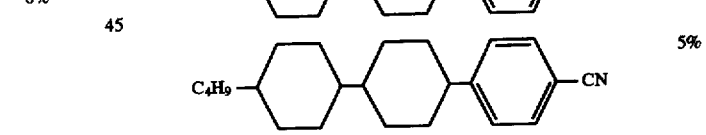 5%
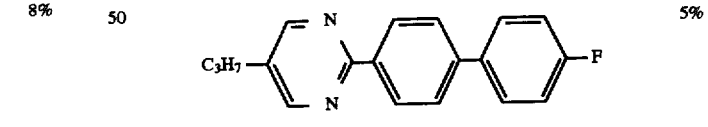 5%
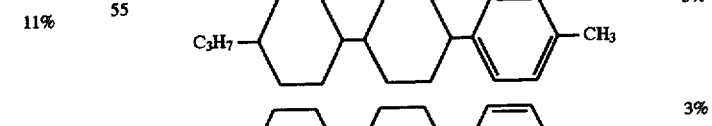 5%
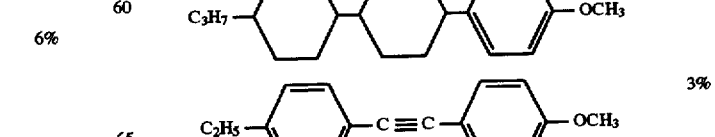 5%
 3%
 3%

-continued

| Structure | % |
|---|---|
| C₃H₇—⟨phenyl⟩—C≡C—⟨phenyl⟩—OCH₃ | 3% |
| C₄H₉—⟨phenyl⟩—C≡C—⟨phenyl⟩—OCH₃ | 3% |
| C₄H₉—⟨phenyl⟩—C≡C—⟨phenyl⟩—OC₂H₅ | 3% |
| C₅H₁₁—⟨phenyl⟩—C≡C—⟨phenyl⟩—OCH₃ | 3% |
| C₃H₇—⟨cyclohexyl⟩—⟨cyclohexyl⟩—C₄H₉ | 9% |
| C₃H₇—⟨cyclohexyl⟩—⟨cyclohexyl⟩—C₅H₁₁ | 3% |

COMPOSITION EXAMPLE 8

| Structure | % |
|---|---|
| FC₃H₆—⟨cyclohexyl⟩—CH₂CH₂—⟨C₆H₂F₂⟩—⟨C₆H₂F₂⟩—CF₃ (Compound No. 80) | 11% |
| FC₃H₆—⟨cyclohexyl⟩—CH₂CH₂—⟨C₆H₂F₂⟩—⟨C₆H₃F⟩—OCF₃ (Compound No. 77) | 10% |
| C₃H₇—⟨cyclohexyl⟩—⟨phenyl⟩—CN | 7% |
| CH₂=CHCH₂—⟨cyclohexyl⟩—⟨phenyl⟩—CN | 9% |
| CH₃CH=CHCH₂—⟨cyclohexyl⟩—⟨phenyl⟩—CN | 9% |
| C₃H₇—⟨cyclohexyl⟩—⟨cyclohexyl⟩—⟨phenyl⟩—CN | 5% |

-continued

| Structure | % |
|---|---|
| C₃H₇—⟨pyridazine⟩—⟨phenyl⟩—⟨phenyl⟩—F | 7% |
| C₂H₅—⟨pyridazine⟩—⟨phenyl⟩—⟨cyclohexyl⟩—C₃H₇ | 5% |
| C₃H₇—⟨pyridazine⟩—⟨phenyl⟩—⟨cyclohexyl⟩—C₃H₇ | 5% |
| C₂H₅—⟨phenyl⟩—C≡C—⟨phenyl⟩—CH₃ | 4% |
| CH₃—⟨phenyl⟩—C≡C—⟨phenyl⟩—C₆H₁₃ | 8% |
| C₄H₉—⟨phenyl⟩—C≡C—⟨phenyl⟩—C₄H₉ | 4% |
| CH₃OCH₂—⟨cyclohexyl⟩—⟨cyclohexyl⟩—C₃H₇ | 5% |
| C₃H₇—⟨cyclohexyl⟩—⟨cyclohexyl⟩—C₄H₉ | 8% |
| C₃H₇—⟨cyclohexyl⟩—⟨cyclohexyl⟩—⟨phenyl⟩—CH₃ | 3% |

COMPOSITION EXAMPLE 9

| Structure | % |
|---|---|
| FC₅H₁₀—⟨cyclohexyl⟩—⟨cyclohexyl⟩—CH₂CH₂—⟨C₆H₃F⟩—OCF₃ (Compound No. 30) | 10% |
| FC₃H₆—⟨cyclohexyl⟩—CH₂CH₂—⟨cyclohexyl⟩—⟨C₆H₃F⟩—OCF₃ (Compound No. 35) | 10% |
| C₂H₅—⟨phenyl⟩—⟨phenyl⟩—CN | 7% |

-continued

| Structure | % |
|---|---|
| CH₃OCH₂–(Cy)–(Ph)–CN | 8% |
| C₂H₅OCH₂–(Cy)–(Ph)–CN | 8% |
| C₂H₅–(Ph)–COO–(Ph)–CN | 4% |
| C₅H₁₁–(pyrimidine)–(Ph)–F | 5% |
| C₃H₇–(pyrimidine)–(Ph)–(Ph)–F | 6% |
| C₂H₅–(pyrimidine)–(Ph)–C₂H₅ | 3% |
| C₃H₇–(pyrimidine)–(Ph)–C₂H₅ | 3% |
| C₄H₉–(pyrimidine)–(Ph)–C₂H₅ | 3% |
| C₂H₅–(pyrimidine)–(Ph)–(Cy)–C₃H₇ | 4% |
| C₃H₇–(pyrimidine)–(Ph)–(Cy)–C₃H₇ | 4% |
| C₄H₉–(pyrimidine)–(Ph)–(Cy)–C₃H₇ | 4% |
| C₃H₇–(pyrimidine)–(Ph)–OC₂H₅ | 4% |
| C₂H₅–(Cy)–(Cy)–(Ph)–CH₃ | 5% |
| C₃H₇–(Cy)–(Cy)–(Ph)–CH₃ | 5% |
| C₃H₇–(Cy)–(Cy)–(Cy)–C₃H₇ | 7% |

COMPOSITION EXAMPLE 10

| Structure | % |
|---|---|
| FC₅H₁₀–(Ph)–(Ph)–OCF₃  (Compound No. 11) | 6% |
| FC₃H₆–(Cy)–(Cy)–(Ph,F,F)–(Ph,F)–OCF₃  (Compound No. 240) | 4% |
| FC₅H₁₀–(Cy)–(Cy)–CH₂CH₂–(Ph,F,F)–CF₃  (Compound No. 31) | 10% |
| C₂H₅OCH₂–(Ph)–COO–(Ph,F)–CN | 3% |
| C₃H₇OCH₂–(Ph)–COO–(Ph,F)–CN | 10% |
| C₂H₅–(Cy)–(Ph,F)–CN | 8% |
| C₃H₇–(Cy)–(Ph,F)–CN | 9% |
| C₃H₇–(Cy)–(Cy)–(Ph,F)–CN | 4% |
| C₂H₅–(Cy)–(Cy)–(Ph,F,F) | 3% |
| C₃H₇–(Cy)–(Cy)–(Ph,F,F) | 3% |
| C₅H₁₁–(Cy)–(Cy)–(Ph,F,F) | 3% |
| C₃H₇–(Cy)–CH₂CH₂–(Ph)–C≡C–(Ph)–C₂H₅ | 3% |
| C₃H₇–(Cy)–CH₂CH₂–(Ph)–C≡C–(Ph)–C₃H₇ | 3% |

-continued

| Structure | % |
|---|---|
| C₃H₇—⬡—CH₂CH₂—⌬—C≡C—⌬—C₄H₉ | 3% |
| C₃H₇—⬡—⌬(F)—C≡C—⌬—C₂H₅ | 4% |
| C₃H₇—⬡—⌬(F)—C≡C—⌬—C₃H₇ | 4% |
| C₃H₇—⬡—⌬(F)—C≡C—⌬—C₄H₉ | 4% |
| C₃H₇—⬡—⬡—⌬—CH₃ | 8% |
| C₃H₇—⬡—⬡—⌬—C₃H₇ | 4% |
| C₃H₇—⬡—⬡—⌬—OCH₃ | 4% |

COMPOSITION EXAMPLE 11

| Structure | % |
|---|---|
| FC₂H₄—⬡—⬡—CH₂CH₂—⌬—OCF₃ (Compound No. 17) | 7% |
| FC₃H₆—⬡—⌬(F,F)—CH₂CH₂—⌬(F)—OCF₃ (Compound No. 122) | 6% |
| FC₅H₁₀—⬡—⬡—⌬(F,F)—⌬—OCF₃ (Compound No. 247) | 3% |
| C₂H₅—⬡—⌬(F)—CN | 13% |
| C₃H₇—⬡—⌬(F)—CN | 13% |
| C₃H₇OCH₂—⌬—COO—⌬(F)—CN | 8% |
| C₃H₇—⬡—⬡—COO—⌬—F | 4% |
| C₅H₁₁—⬡—⬡—COO—⌬—F | 4% |

-continued

| Structure | % |
|---|---|
| C₃H₇—⬡—⬡—COO—⌬(F,F,F) | 12% |
| C₅H₁₁—⬡—⬡—COO—⌬(F,F,F) | 8% |
| C₃H₇—⬡—⌬—COO—⌬(F,F,F) | 4% |
| C₅H₁₁—⬡—⌬—COO—⌬(F,F,F) | 4% |
| C₃H₇—⬡—⬡—⌬—CH₃ | 7% |
| C₃H₇—⬡—⬡—⌬—OCH₃ | 4% |
| C₃H₇—⬡—⬡—⌬—C₃H₇ | 3% |

COMPOSITION EXAMPLE 12
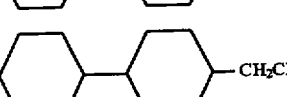 (Compound No. 19) 6%
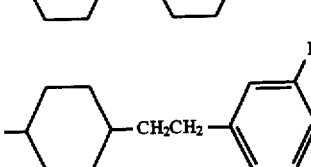 (Compound No. 18) 6%
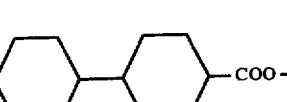 (Compound No. 77) 7%
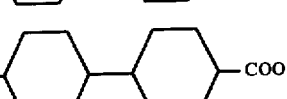 3%
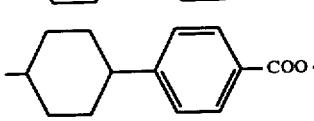 3%
 3%
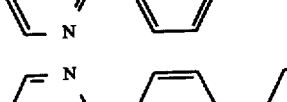 7%
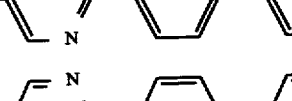 5%
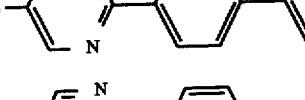 5%
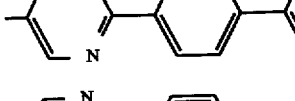 5%
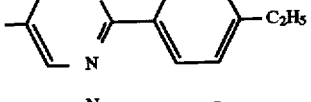 5%
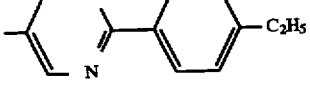 5%

| Structure | % |
|---|---|
| C₃H₇–[Cy]–COO–[Ph]–OC₄H₉ | 5% |
| C₄H₉–[Cy]–COO–[Ph]–OC₄H₉ | 5% |
| C₅H₁₁–[Cy]–COO–[Ph]–OC₄H₉ | 5% |
| C₂H₅–[Cy]–CH₂CH₂–[Ph]–C≡C–[Ph]–C₄H₉ | 4% |
| C₃H₇–[Cy]–CH₂CH₂–[Ph]–C≡C–[Ph]–C₄H₉ | 5% |
| C₃H₇–[Cy]–[Cy]–[Ph]–CH₃ | 6% |
| C₃H₇–[Cy]–[Cy]–[Ph]–C₃H₇ | 5% |

COMPOSITION EXAMPLE 13

| Structure | % |
|---|---|
| FC₅H₁₀–[Cy]–CH₂CH₂–[Cy]–[Ph]–OCF₃ (Compound No. 48) | 7% |
| FC₅H₁₀–[Cy]–CH₂CH₂–[Cy]–[Ph(2,6-F₂)]–CF₃ (Compound No. 90) | 8% |
| C₃H₇–[Cy]–[Cy]–OCH₃ | 4% |
| C₃H₇–[Cy]–[Cy]–OC₃H₇ | 4% |
| C₅H₁₁–[Cy]–[Cy]–OCH₃ | 6% |
| C₅H₁₁–[Cy]–[Ph]–F | 6% |
| C₂H₅–[Cy]–[Cy]–[Ph]–OCF₃ | 4% |
| C₃H₇–[Cy]–[Cy]–[Ph]–OCF₃ | 4% |
| C₄H₉–[Cy]–[Cy]–[Ph]–OCF₃ | 6% |
| C₅H₁₁–[Cy]–[Cy]–[Ph]–OCF₃ | 6% |
| C₃H₇–[Cy]–[Cy]–CH₂CH₂–[Ph(3,4-F₂)] | 6% |
| C₅H₁₁–[Cy]–[Cy]–CH₂CH₂–[Ph(3,4-F₂)] | 6% |
| C₃H₇–[Cy]–[Cy]–[Ph(3,5-F₂)]–OCHF₂ | 10% |
| C₃H₇–[Cy]–[Cy]–COO–[Ph(3,4-F₂)] | 5% |
| C₅H₁₁–[Cy]–[Ph]–[Ph(3,4-F₂)] | 3% |
| C₅H₁₁–[Cy]–[Ph]–[Ph(3-F)]–C₂H₅ | 3% |
| C₃H₇–[Cy]–[Cy]–[Ph]–OCHF₂ | 6% |
| C₅H₁₁–[Cy]–[Cy]–[Ph]–OCHF₂ | 6% |

COMPOSITION EXAMPLE 14
| Structure | % |
|---|---|
| 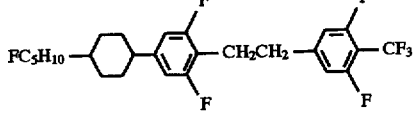 (Compound No. 134) | 8% |
| 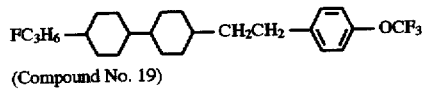 (Compound No. 19) | 8% |
| 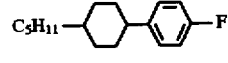 | 8% |
| 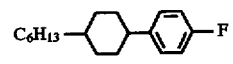 | 8% |
| 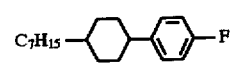 | 8% |
| 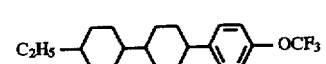 | 7% |
| 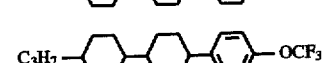 | 7% |
| 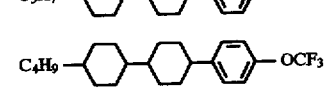 | 7% |
|  | 7% |
-continued
| Structure | % |
|---|---|
| 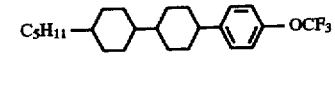 | 5% |
| 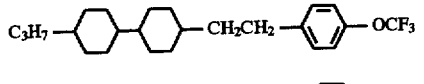 | 5% |
| 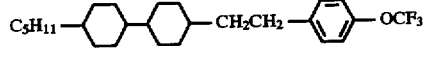 | 8% |
| 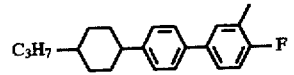 | 8% |
|  | 3% |
| 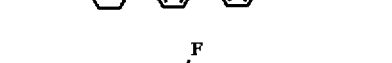 | 3% |
COMPOSITION EXAMPLE 15
| Structure | % |
|---|---|
| 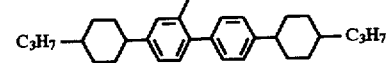 (Compound No. 30) | 9% |
| 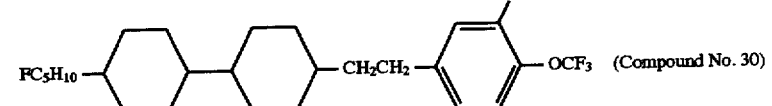 (Compound No. 48) | 7% |
| 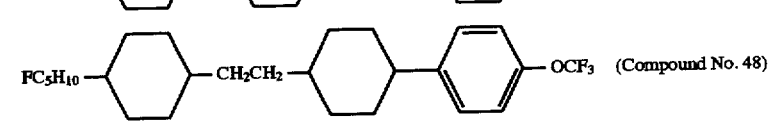 | 5% |
| 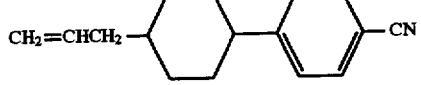 | 4% |
| 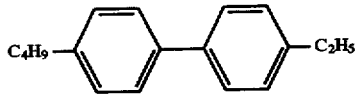 | 6% |
| 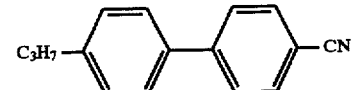 | 6% |
|  | 6% |

-continued

| Structure | % |
|---|---|
| C₃H₇–(Cy)–CH₂CH₂–(Ph)–OC₂H₅ | 6% |
| C₅H₁₁–(Cy)–CH₂CH₂–(Ph)–OC₃H₇ | 8% |
| C₃H₇–(Ph)–COO–(Ph)–CN | 6% |
| C₅H₁₁–(Cy)–COO–(Ph)–OCH₃ | 11% |
| C₅H₁₁–(Cy)–COO–(Ph)–OC₃H₇ | 11% |
| C₅H₁₁–(Ph)–(Ph)–(Ph)–CN | 3% |
| C₄H₉–(Ph)–(pyrimidine)–(Ph)–CN | 3% |
| C₄H₉–(Ph)–(pyrimidine)–(Ph)–C₅H₁₁ | 3% |
| C₅H₁₁–(Cy)–(Ph)–CH₂CH₂–(Ph)–C₄H₉ | 3% |
| C₅H₁₁–(Cy)–(Ph)–(Ph)–CH₂CH₂–(Ph)–C₃H₇ | 3% |

COMPOSITION EXAMPLE 16
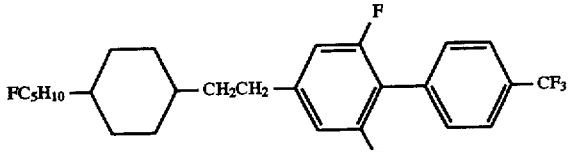 7%
(Compound No. 90)
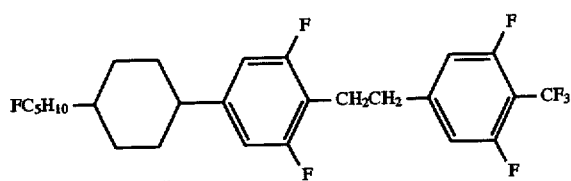 7%
(Compound No. 134)
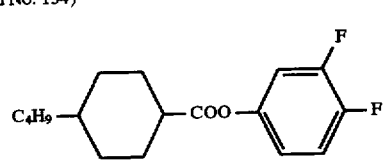 6%
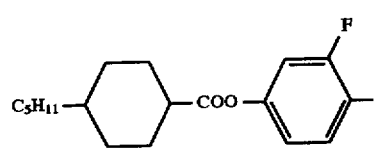 6%
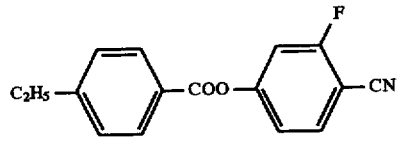 5%
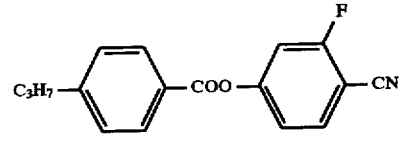 5%
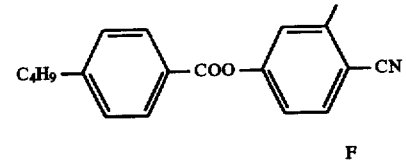 6%
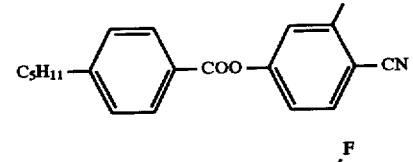 6%
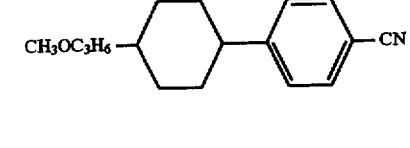 10%
 6%

-continued
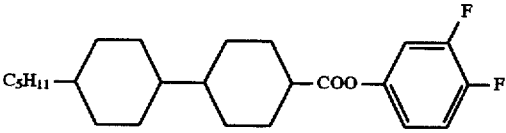 6%
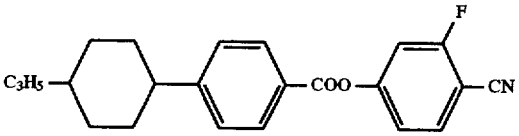 4%
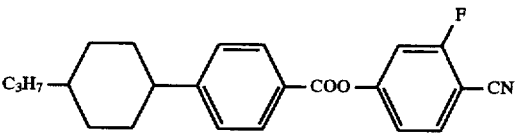 4%
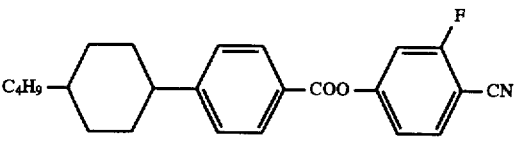 6%
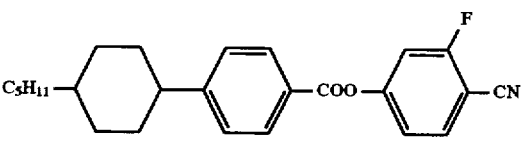 6%
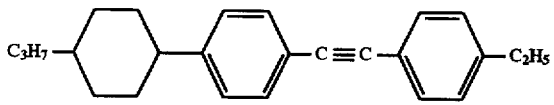 10%
COMPOSITION EXAMPLE 17
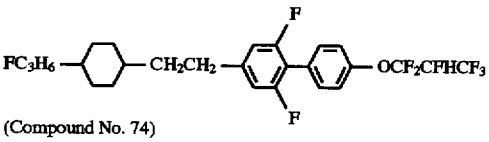 10%
(Compound No. 74)
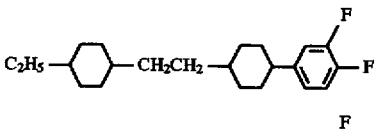 10%
(Compound No. 77)
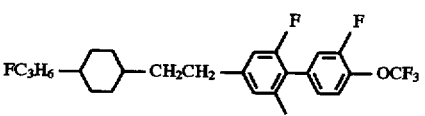 6%
(Compound No. 13)
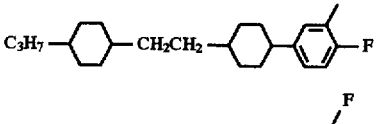 5%
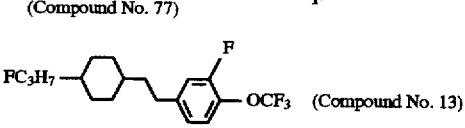 5%
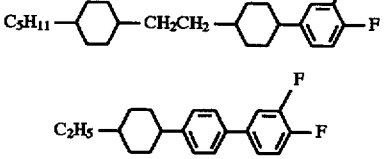 5%
-continued
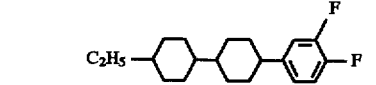 8%
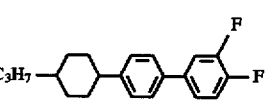 4%
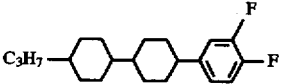 8%
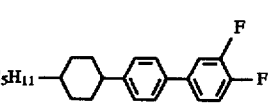 5%
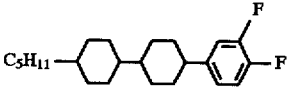 5%
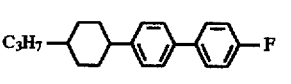 10%
 4%

-continued
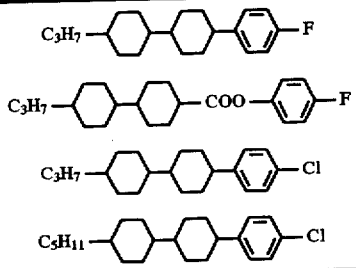
4%
4%
4%
3%
COMPOSITION EXAMPLE 18
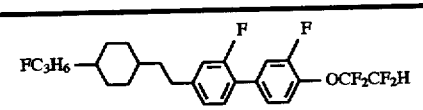  10%
(Compound No. 86)
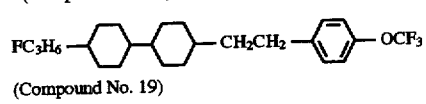  9%
(Compound No. 19)
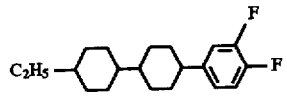  10%
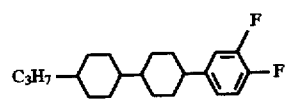  10%
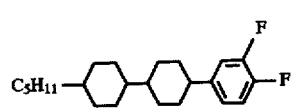  10%
  7%
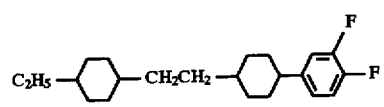  4%
  2%
  4%
  6%
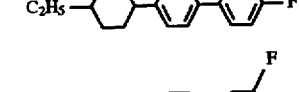  6%
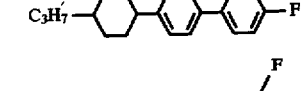  12%
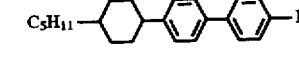
-continued
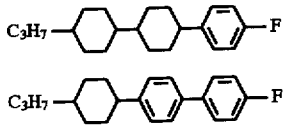  5%
5%
COMPOSITION EXAMPLE 19
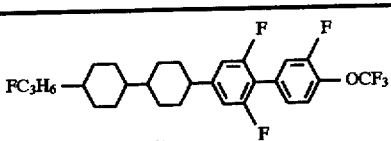  4%
(Compound No. 240)
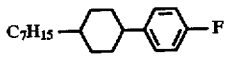  3%
  4%
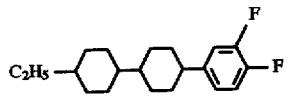  13%
  13%
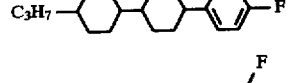  13%
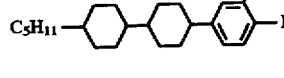  4%
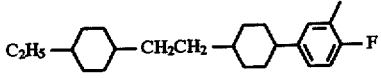  2%
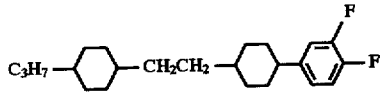  4%
  3%
  3%
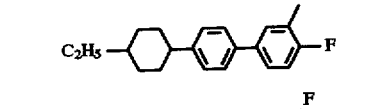  6%
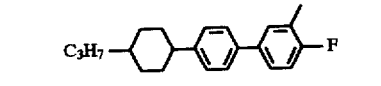  8%
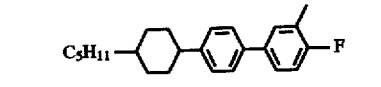  3%

-continued

| Structure | % |
|---|---|
| C₅H₁₁—⟨Cy⟩—⟨Cy⟩—COO—⟨Ph⟩—F | 3% |
| C₃H₇—⟨Cy⟩—⟨Cy⟩—CH₂CH₂—⟨Ph⟩—OCF₃ | 3% |
| C₃H₇—⟨Cy⟩—⟨Cy⟩—⟨Ph⟩—OCF₃ | 5% |
| C₃H₇—⟨Cy⟩—⟨Cy⟩—CH₂CH₂—⟨Ph(F,F)⟩ | 6% |

This composition exhibited a clearing point of 113.8° C., a threshold value in a cell thickness of 8.7 μm of 2.59 V, a Δε of 4.5, a Δn of 0.090 and a viscosity at 20° C. of 23.1 mPa.S.

COMPOSITION EXAMPLE 20

| Structure | % |
|---|---|
| FC₃H₆—⟨Cy⟩—⟨Cy⟩—⟨Ph(F,F)⟩—⟨Ph(F,OCF₃)⟩ (Compound No. 240) | 8% |
| FC₃H₆—⟨Cy⟩—⟨Cy⟩—CH₂CH₂—⟨Ph⟩—CF₃ (Compound No. 18) | 8% |
| C₇H₁₅—⟨Cy⟩—⟨Ph(F,F,F)⟩ | 4% |
| C₃H₇—⟨Cy⟩—CH₂CH₂—⟨Ph(F,F,F)⟩ | 10% |
| C₅H₁₁—⟨Cy⟩—CH₂CH₂—⟨Ph(F,F,F)⟩ | 9% |
| C₃H₇—⟨Cy⟩—⟨Cy⟩—⟨Ph(F,F,F)⟩ | 6% |
| C₄H₉—⟨Cy⟩—⟨Cy⟩—⟨Ph(F,F,F)⟩ | 6% |
| C₃H₇—⟨Cy⟩—⟨Cy⟩—CH₂CH₂—⟨Ph(F,F,F)⟩ | 6% |

-continued

| Structure | % |
|---|---|
| C₅H₁₁—⟨Cy⟩—⟨Cy⟩—CH₂CH₂—⟨Ph(F,F,F)⟩ | 6% |
| C₃H₇—⟨Cy⟩—⟨Ph⟩—⟨Ph(F,F,F)⟩ | 10% |
| C₅H₁₁—⟨Cy⟩—⟨Ph⟩—⟨Ph(F,F,F)⟩ | 10% |
| C₃H₇—⟨Cy⟩—⟨Cy⟩—COO—⟨Ph(F,F,F)⟩ | 9% |
| C₄H₉—⟨Cy⟩—⟨Cy⟩—COO—⟨Ph(F,F,F)⟩ | 2% |
| C₅H₁₁—⟨Cy⟩—⟨Cy⟩—COO—⟨Ph(F,F,F)⟩ | 2% |
| C₂H₅—⟨Cy⟩—⟨Cy⟩—⟨Ph⟩—⟨Ph(F,F)⟩ | 2% |
| C₃H₇—⟨Cy⟩—⟨Cy⟩—⟨Ph⟩—⟨Ph(F,F)⟩ | 2% |

This composition exhibited a clearing point of 92.1° C., a threshold voltage in a cell thickness of 8.7 μm of 1.78 V, a Δε of 9.1, a Δn of 0.093 and a viscosity at 20° C. of 31.2 mPa.S.

COMPOSITION EXAMPLE 21

| Structure | % |
|---|---|
| FC₃H₆—⟨Cy⟩—⟨Cy⟩—CH₂CH₂—⟨Ph⟩—CF₃ (Compound No. 18) | 4% |
| C₃H₇—⟨Cy⟩—⟨Ph⟩—Cl | 7% |

-continued

| Structure | % |
|---|---|
| C₇H₁₅—[Cy]—[Ph(F,F,F)] | 10% |
| C₂H₅—[Cy]—[Ph]—[Ph(F,F)] | 7.5% |
| C₃H₇—[Cy]—[Ph]—[Ph(F,F)] | 7.5% |
| C₅H₁₁—[Cy]—[Ph]—[Ph(F,F)] | 15% |
| C₂H₅—[Cy]—[Cy]—[Ph]—Cl | 5% |
| C₄H₉—[Cy]—[Cy]—[Ph]—Cl | 10% |
| C₅H₁₁—[Cy]—[Cy]—[Ph]—Cl | 5% |
| C₃H₇—[Cy]—[Ph]—[Ph(F,F,F)] | 10% |
| C₅H₁₁—[Cy]—[Ph]—[Ph(F,F,F)] | 9% |
| C₃H₇—[Cy]—[Ph(F)]—CH=CH—[Ph]—C₂H₅ | 5% |
| C₃H₇—[Cy]—[Ph(F)]—C≡C—[Ph]—C₃H₇ | 5% |

This composition exhibited a clearing point of 89.5° C., a threshold voltage in a cell thickness of 8.7 μm of 2.09 V, a Δε of 5.5, a Δn of 0.128 and a viscosity at 20° C. of 22.7 mPa.S.

COMPOSITION EXAMPLE 22

| Structure | % |
|---|---|
| FC₃H₆—[Cy]—[Cy]—[Ph(F,F)]—[Ph(F)]—OCF₃ (Compound No. 240) | 2% |

-continued

| Structure | % |
|---|---|
| FC₃H₆—[Cy]—[Cy]—CH₂CH₂—[Ph]—CF₃ (Compound No. 18) | 4% |
| CH₂=CHC₂H₄—[Cy]—[Ph]—CN | 9% |
| (CH₃)(H)C=C(H)—C₂H₄—[Cy]—[Ph]—CN | 9% |
| C₃H₇—[Cy]—[Ph]—CN | 14% |
| CH₃OCH₂—[Cy]—[Ph]—CN | 8% |
| C₂H₅OCH₂—[Cy]—[Ph]—CN | 4% |
| C₃H₇—[Cy]—[Cy]—[Ph]—CN | 4% |
| C₃H₇—[Cy]—[Cy]—C₄H₉ | 5% |
| C₃H₇—[Cy]—C₂H₄—C(H)=C(CH₃)(H) | 5% |
| CH₃OCH₂—[Cy]—[Cy]—C₅H₁₁ | 8% |
| C₂H₅—[Ph]—C≡C—[Ph]—OCH₃ | 11% |
| C₃H₇—[Cy]—[Cy]—[Ph]—CH₃ | 4% |
| C₃H₇—[Cy]—[Cy]—[Ph]—C₃H₇ | 9% |
| CH₂=CH—C(H)=C(H)—[Cy]—[Cy]—[Ph]—CH₃ | 4% |

This composition exhibited a clearing point of 76.1° C., a threshold voltage in a cell thickness of 8.7 mm of 1.89 V, a Δε of 7.6, a Δn of 0.124 and a viscosity at 20° C. of 18.4 mPa.S.

COMPOSITION EXAMPLE 23

| Structure | % |
|---|---|
| FC₃H₆—[Cy]—[Cy]—[Ph(F,F)]—[Ph(F)]—OCF₃ (Compound No. 240) | 10% |

-continued

| Structure | % |
|---|---|
| (CH₃)₂CH-C₂H₄-⌬-COO-⌬(F,F)-CN | 11% |
| C₂H₅OCH₂-⌬-COO-⌬(F)-CN | 5% |
| C₃H₇OCH₂-⌬-COO-⌬(F)-CN | 9% |
| C₃H₇-cyclohexyl-⌬(F)-CN | 15% |
| C₃H₇-cyclohexyl-cyclohexyl-C₄H₉ | 9% |
| CH₃OCH₂-cyclohexyl-cyclohexyl-C₃H₇ | 3% |
| C₄H₉-⌬-C≡C-⌬-OC₂H₅ | 5% |
| C₂H₅-⌬-C≡C-⌬-CH₃ | 1% |
| CH₃-⌬-C≡C-⌬-C₆H₁₃ | 2% |
| C₄H₉-⌬-C≡C-⌬-C₄H₉ | 1% |
| C₂H₅-cyclohexyl-cyclohexyl-⌬(F)-CN | 9% |
| C₃H₇-cyclohexyl-cyclohexyl-⌬(F)-CN | 8% |
| C₃H₇-cyclohexyl-CH₂CH₂-⌬-C≡C-⌬-C₂H₅ | 4% |
| C₃H₇-cyclohexyl-CH₂CH₂-⌬-C≡C-⌬-C₃H₇ | 4% |
| C₃H₇-cyclohexyl-CH₂CH₂-⌬-C≡C-⌬-C₄H₉ | 4% |

This composition exhibited a clearing point of 77.0° C., a threshold voltage in a cell thickness of 8.7 μm of 0.96 V, a Δε of 24.2, a Δn of 0.145 and a viscosity at 20° C. of 39.8 mPa.S.

PREFERRED EMBODIMENTS OF THE PRESENT INVENTION

The present invention will be described in more details. In the following Examples, C, S, N and I respectively represent crystal, smectic phase, nematic phase and isotropic phase. The units of the transition points are all directed to ° C.

EXAMPLE 1

Preparation of 1-(2-(4-(3-fluoropropyl)cyclohexyl)ethyl)-3,5-difluoro-4-(3,5-difluoro-4-trifluoromethylphenyl) benzene (a compound No. 80)(in the formula (I), wherein n=3, ring E=1,4-cyclohexylene, G=covalent bond, L=ring Z=3,5-difluoro-1,4-phenylene, k=1, l=0, m=0, Q=covalent bond and Y=CF₃)

(First step)

A Grignard reagent was prepared from 3,5-dibromobenzene (150 g, 0.78 mol), and dried Mg (18.9 g, 0.78 mol) in ether (600 ml), followed by slowly dropwise adding a 100 ml ether solution of ethylene oxide (100 g, 2.27 mol) to the reagent under −50° C. cooling, heating the mixture up to room temperature, stirring the reaction solution for one hour, adding it into 6N hydrochloric acid (500 ml), extracting the resulting product with toluene, washing the extraction solution successively with a saturated aqueous solution of sodium bicarbonate and water, drying over magnesium sulfate, distilling off the solvent, adding an aqueous HBr (47%) (500 ml) to the residue, refluxing the mixture for 7 hours, and distilling under reduced pressure using Vigoureux tube, to obtain a colorless, transparent liquid, 3,5-difluorophenetylbromide (41 g, 0.19 mol) (b.p. 52° to 53° C. under 2 Torr). The yield of this product from 3,5-difluorobromobenzene was 23.8%. A Grignard reagent was prepared from the product (20.0 g, 90.5 mmol) and dried Mg (2.2 g, 90.5 mmol) in ether (150 ml), cooling the agent down to 0° C., dropwise adding thereto a 130 ml ether solution of commercially available cyclohexanedione monoethylene ketal (14.2 g, 90.9 mmol), heating the reaction solution up to room temperature, stirring it for 3 hours, adding the reaction solution to 6N HCl (500 ml), extracting the product with toluene, washing the extract successively with a saturated, aqueous solution of sodium bicarbonate and water, drying over magnesium sulfate, distilling off the solvent, adding to the residue (20 g), toluene (100 ml) and Amberlist (1 g), refluxing the mixture for 5 hours while removing water formed by the reaction, by means of Dean Stark, adding ethyleneglycol (2 g), further refluxing for 2 hours, adding water (100 ml) to the reaction solution, washing the organic layer successively with a saturated aqueous solution of sodium bicarbonate and water, drying over magnesium sulfate, distilling off the solvent, purifying the residue according to column chromatography using toluene/ethyl acetate (4:1) as a developing solvent, hydrogenating the resulting purified substance in ethanol in the presence of 5% Pd/C catalyst (1.02 g), filtering off the catalyst, distilling off under reduced pressure, refluxing the resulting concentrate in formic acid (80 ml) for 3 hours, adding water (200 ml), extracting the product with toluene, washing the extraction liquid successively with a saturated aqueous solution of sodium bicarbonate and water, drying the toluene layer over magnesium sulfate, and distilling off toluene to obtain 4-(3,5-difluorophenylethyl)-1-cyclohexanone (10.1 g, 42.4 mmol). The yield of this product from 3,5-difluorobromobenzene was 46.6%.

(Second step)

3-Fluorobromopropane (200.0 g, 1.42 mol) was dissolved in toluene (3), followed by adding to the solution, triphenylphosphine (37.2 g, 1.42 mol), refluxing the mixture for 15 hours, filtering off the resulting product, and suction-drying, to obtain 3-fluoropropyltriphenylphosphine bromide (486 g, 1.21 mol). Yield: 85.2%.

(Third step)

THF (100 ml) was added to the above 3-fluoropropyltriphenylphosphine bromide (22.0 g, 54.6 mmol), followed by cooling the mixture down to −50° C. in a nitrogen atmosphere, adding to the mixture, a 70 ml THF solution of potassium-t-butoxide (6.10 g, 54.5 mmol), stirring the mixture for 3 hours, dropwise adding to the reaction solution, a 80 ml THF solution of 4-(3,5-difluorophenetyl)-1-cyclohexanone (10.0 g, 42.0 mmol), stirring the mixture for one hour at the same temperature, and heating it up to room temperature for 4 hours, adding water (200 ml) to the resulting reaction solution, extracting the resulting product with ethyl acetate, washing the extraction solution successively with a saturated aqueous solution of sodium bicarbonate and water, drying the organic layer over magnesium sulfate, distilling off the solvent under reduced pressure, purifying the residue according to column chromatography treatment using toluene as a developing solvent, hydrogenating the resulting purified substance in the presence of 5% Pd/C catalyst, in ethanol, and thereafter filtering off the catalyst to obtain 4-(3,5-difluorophenetyl)-1-(3-fluoropropyl)cyclohexane (2.51 g, 8.83 mmol). Yield: 21.0%.

(Fourth step)

THF (30 ml) was added to the above 4-(3,5-difluorophenetyl)-1-(3-fluoropropyl)cyclohexane (2.51 g, 8.83 mmol), followed by cooling the mixture down to −50° C. in a nitrogen gas atmosphere, dropwise adding thereto a hexane solution (7 ml, 11.4 mmol) of 1.63N n-butyllithium by means of a syringe, stirring the mixture for one hour at the same temperature, dropwise adding a 0.5 mol ZnCl$_2$ THF solution (22.8 ml, 11.4 mol), heating the reaction substance up to room temperature, further stirring it for 2 hours, adding to the reaction solution, tetraxistriphenylphosphine palladium (250 mg) as a catalyst, dropwise adding 3,5-difluoro-4-trifluoromethylphenyl bromide (2.97 g, 11.4 mmol), refluxing the mixture for 2 hours adding the reaction solution to cooled 6N-HCl, extracting the resulting product with toluene, washing the extraction solution successively with a saturated aqueous solution of sodium bicarbonate and water, drying over magnesium sulfate, distilling off the solvent, to obtain an orange color suspension (8.5 g), purifying it according to column chromatography treatment using a developing solvent of toluene/heptane (1/1), on silica gel, and recrystallization, to obtain trans-form of 1-(2-(4-(3-fluoropropyl)cyclohexyl)ethyl)-3,5-difluoro-4-(3,5-difluoro-4-trifluoromethylphenyl)benzene (0.35 g, 0.75 mmol). Yield: 8.49%, C-I point: 83.7° C. 1H-NMR (CDCl3) δ(ppm): 7.10 (d, 2H), 6.84 (d, 2H), 4.69 (t, 1H), 4.16 (t, 1H), 2.66 (t, 2H), 1.84–0.88 (m, 18H).

EXAMPLE 2

Preparation of 1-(2-(4-(4-(2-fluoroethyl)cyclohexyl) cyclohexyl)ethyl-4-trifluoromethoxybenzene (a compound No. 17) (in the formula (1), wherein n=2, ring E=1,4-cyclohexylene, G=covalent bond, L=1,4-cyclohexylene, ring Z=1,4-phenylene, k=l=0, m=1, Q=—O—and Y=CF$_3$)

(First step)

THF (1 l) was added to ethoxycarbonylmethyldimethylphosphonate (125 g, 0.556 mol), followed by cooling the mixture down to −50° C. in a nitrogen gas atmosphere, followed by gradually adding to the mixture, potassium-t-butoxide (62.3 g, 0.556 mol), stirring the mixture at the same temperature for one hour, adding thereto, a THF 400 ml solution of bicyclohexanedione monoethylene ketal (117 g, 0.464 mol), stirring the mixture at room temperature for 10 hours, adding water (500 ml) to the reaction solution, extracting the resulting product with toluene, washing the extraction solution successively with a saturated aqueous solution of sodium bicarbonate and water, drying over magnesium sulfate, distilling off the solvent under reduced pressure to obtain an yellow liquid (218.2 g), dissolving it in ethanol, hydrogenating in the presence of Raney Ni catalyst, filtering off the catalyst, distilling off ethanol under reduced pressure, purifying the residue according to column chromatography using toluene as a developing solvent on silica gel, to isolate colorless, oily 4-(1,4-dioxaspiro[4.5]decyl) cyclohexylmethanoic acid ethyl ester (183.2 g, 0.464 mol).

(Second step)

Dried THF (100 ml) was added to lithium aluminum hydride (17.6 g, 0.464 mol), followed by cooling the mixture down to 0° C., dropwise adding thereto a 800 ml THF solution of the above 4-(1,4-dioxaspiro[4.5]decyl) cyclohexylmethanoic acid ethyl ester (183.2 g, 0.464 mol), stirring at 0° C. for 3 hours, stirring at room temperature for 2 hours, washing the reaction solution successively with 3N HCl, a saturated aqueous solution of sodium bicarbonate and water, distilling off the solvent, and recrystallizing, to isolate colorless crystals of 2-(4-(1,4-dioxaspiro[4.5]decyl) cyclohexyl)ethanol (50.6 g, 0.179mol). Yield from bicyclohexanedione monoethylene ketal was 38%.

(Third step)

The above 2-(4-(1,4-dioxaspiro[4.5]decyl)cyclohexyl) ethanol (20 g, 70.8 mmol) was dissolved in dichloromethane (70 ml), followed by dropwise adding to the solution, DAST (13 g, 80.7 mmol), stirring at 0° C. for one hour, adding water to the reaction solution, washing the resulting organic layer successively with a saturated aqueous solution of sodium bicarbonate and water, distilling off the solvent, purifying the residue according to column chromatography using heptane/ethyl acetate as a developing solvent, on silica gel, to obtain 1-(4-(1,4-dioxaspiro[4.5]decyl)cyclohexyl)-2-fluoroethane, adding thereto formic acid (80 ml), refluxing the mixture for 2 hours, extracting the resulting product with toluene, washing the extraction solution successively with a saturated aqueous solution of sodium bicarbonate, distilling off the solvent, to isolate 4-(4-(2-fluoroethyl)cyclohexyl) cyclohexanone (8.0 g, 35.3 mmol). The yield of this product from 2-(4-(1,4-dioxaspiro[4.5]decyl)cyclohexyl)ethanol was 49.9%.

(Fourth step)

A Grignard reagent prepared from 4-trifluoromethoxybromobenzene (54 g, 220 mmol) and dried Mg (5.4 g, 220 mmol) in 250 ml ether solvent was cooled down to −50° C., followed by gradually dropwise adding thereto ethylene oxide (29.3 g, 670 mmol), gradually heating the resulting reaction mixture up to room temperature, further stirring it for one hour at room temperature, adding the reaction solution to 6N HCl (300 ml), extracting the resulting product with ethyl acetate, washing the extraction solution successively with a saturated aqueous solution of sodium bicarbonate and water, drying over magnesium sulfate, distilling off the solvent, distilling the residue under reduced pressure by means of a Vigoureaux tube, to isolate a colorless liquid, 2-(4-trifluoromethoxyphenyl)ethanol (14.5 g, 70.3 mmol) having a b.p. of 82° to 84° C. under 3.5 Torr, adding to this liquid, xylene (60 ml) and HBr aqueous solution (47%) (60 ml), refluxing the mixture for 9 hours, adding water to the reaction mixture, extracting the resulting product with toluene, washing the reaction solution successively with a saturated aqueous solution of sodium bicarbonate and water, drying the resulting organic layer over magnesium sulfate, distilling off the solvent, distilling the residue under reduced pressure using Vigoureux tube, to isolate a colorless liquid, 2-(4-trifluoromethoxyphenyl)bromoethane (12.0 g, 51.9 mmol) having a b.p. of 75° C. under 4 Torr. The yield of this product from 4-trifluoromethoxybromobenzene was 23.6%.

(Fifth step)

A Grignard reagent prepared from the above 2-(4-trifluoromethoxyphenyl)bromoethane (7.0 g, 30.3 mmol) and dried Mg (0.74 g, 30.4 mmol) in an ether solvent (40 ml) was cooled down to 0° C., followed by dropwise adding thereto a 30 ml ether solution of 4-(4-(2-fluoroethyl)cyclohexyl)cyclohexanone (2.2 g, 9.7 mmol) prepared at the third step, stirring the mixture at 0° C. for 3 hours, adding 6N HCl to the reaction solution, extracting the resulting product with toluene, washing the extraction solution successively with a saturated aqueous solution of sodium bicarbonate and water, drying over magnesium sulfate, distilling off the solvent, adding toluene (100 ml) and Amberlist (500 mg) to the resulting yellow oily substance, refluxing the mixture for 4 hours, while removing water formed by the reaction by means of Dean-Stark, filtering off Amberlist, distilling off the solvent, purifying the residue according to column chromatography treatment using toluene as a developing solvent, on silica gel, to isolate 4-(4-(2-fluoroethyl)cyclohexyl)-1-(2-(4-trifluoromethoxyphenyl)ethyl)-1-cyclohexene (1.8 g, 4.5 mmol), hydrogenating this product (1.2 g, 3.0 mmol) in the presence of 5% Pd/C catalyst (0.12 g) in ethanol solution, filtering off the catalyst, distilling off the solvent under reduced pressure, and recrystallizing the residue, to isolate only trans-form of colorless 1-(2-(4-(4-(2-fluoroethyl)-cyclohexyl)cyclohexyl)ethyl-4-trifluoromethoxybenzene (0.37 g, 0.90 mmol) exhibiting smectic phase. The yield of this product from 4-(4-(2-fluoroethyl)chclohexyl)cyclohexanone was 9.3%.

$S_B$-N point 68.8° C., N-I point 103.5° C.

1H-NMR (CDCl3) δ(ppm): 7.19 (t, 4H), 4.74 (t, 1H), 4.21 (t, 1H), 2.58 (t, 2H), 1.82–0.99 (m, 26H).

EXAMPLE 3

Preparation of 1-(4-(3-fluoropropyl)cyclohexyl)-3,5-difluoro-4-(2-(3-fluoro-4-trifluoromethoxyphenyl)-ethyl)benzene (in the formula (1), n=3, ring E=1,4-cyclohexylene, G=covalent bond, L=3,5-difluoro-1,4-phenylene, ring Z=3-fluoro-1,4-phenylene, k=l=0, m=1, Q=—O—and Y=CF$_3$) (Compound No. 122)

(First step)

A Grignard reagent prepared from 3,5-difluorophenylbromide (193.1 g, 1.00 mol) and dried Mg (24.3 g, 1.00 mol) in THF solvent was cooled down to 0° C., followed by dropwise adding to the agent, a 300 ml ether solution of cyclohexanedione monoethyleneketal (156 g, 1.00 mol), heating the reaction solution up to room temperature, stirring the mixture for 3 hours, adding it to 6N HCl (1 l), extracting the resulting product with toluene, washing the extraction solution successively with a saturated aqueous solution of sodium bicarbonate and water, drying over magnesium sulfate, distilling off the solvent under reduced pressure, adding to the residue, Amberlist (8 g) and toluene (1,000 ml), refluxing for 7 hours while removing water formed by the reaction by means of Dean-Stark, filtering off the Amberlist in the product, distilling off toluene under reduced pressure, purifying the residue according to column chromatography treatment using toluene as a developing agent, on silica gel, to obtain a cyclohexene derivative, adding formic acid (500 ml) to the cyclohexene derivative (62 g), refluxing the mixture for 5 hours, adding water (500 ml) to the reaction solution, extracting the resulting product with toluene, washing the toluene layer successively with a saturated aqueous solution of sodium bicarbonate and water, drying over magnesium sulfate, distilling off toluene under reduced pressure and distilling the residue under reduced pressure, to obtain 4-(3,5-difluorophenyl)cyclohexanone (43.8 g, 20.8 mmol). Yield: 20.8%

(Second step)

THF (60 ml) was added to 3-fluoropropyltriphenylphosphinebromide (10.3 g, 25.5 mmol) prepared at the second step of Example 1, followed by cooling the mixture down to −50° C. in nitrogen atmosphere, adding to the mixture, a 40 ml THF solution of potassium-t-butoxide (2.86 g, 25.5 mmol), stirring the mixture at the same temperature for 3 hours, dropwise adding to the reaction solution, a 100 ml THF solution of 4-(3,5-difluorophenyl)cyclohexanone (43.8 g, 20.8 mmol) prepared at the first step, stirring the mixture at the same temperature for one hour, stirring at room temperature for 3 hours, adding water (200 ml) to the reaction solution, extracting the resulting product with ethyl acetate, washing the organic layer successively with a saturated aqueous solution of sodium bicarbonate and water, drying over magnesium sulfate, purifying an yellow solution obtained by distilling off the solvent, according to column chromatography treatment using toluene as a developing solvent, on silica gel, hydrogenating the resulting cyclohexylidene derivative using a catalyst of Pd/C, in ethanol, filtering off the catalyst after the reaction, distilling off ethanol under reduced pressure and recrystallizing the resulting product using a mixed solvent of heptane with ethanol, to obtain 4-(3,5-difluorophenyl)-1-(3-fluoropropyl)cyclohexane (1.50 g, 6.14 mmol). Yield: 29.5%.

(Third step)

THF (20 ml) was added to the above 4-(3,5-difluorophenyl)-1-(3-fluoropropyl)cyclohexane (1.50 g, 6.14 mmol), followed by cooling the mixture down to −50° C. in a nitrogen atmosphere, dropwise adding thereto a hexane solution 4 ml (6.51 mmol) of 1.63N normal butyllithium by means of a syringe, stirring the mixture at the same temperature for one hour, dropwise adding to the reaction solution, THF 10 ml solution of iodine (1.65 g, 6.51 mmol), stirring the mixture at the same temperature for 30 minutes, adding the reaction solution to 6N HCl, extracting the resulting product with toluene, washing the extraction solution successively with a saturated aqueous solution of sodium bicarbonate and water, drying the organic layer over magnesium sulfate, distilling off the solvent, and purifying the residue according to column chromatography treatment using heptane as a developing solvent, on silica gel, to obtain 4-(3,5-difluorophenyl-4-iodo)-1-3-fluoropropyl)cyclohexane (2.12 g, 5.73 mmol). Yield: 93.3%.

(Fourth step)

A Grignard reagent prepared from 3-fluoro-4-trifluoromethoxyphenylbromide (200.0 g, 772 mmol) and dried Mg (18.8 g, 774 mmol) in ether was cooled down to −50° C. in a nitrogen atmosphere, followed by dropwise adding thereto a 100 ml ether solution of ethylene oxide (100 g, 2.27 mol), stirring the reaction solution at 0° C. for 2 hours, adding the resulting reaction product to 6N HCl, extracting the product with toluene, washing the extraction solution successively a saturated aqueous solution of sodium bicarbonate and water, drying over the organic layer over magnesium sulfate, distilling off the solvent, adding to the residue, 47% hydrogen bromic acid (300 ml) and xylene (300 ml), refluxing the mixture for 9 hours, while removing water formed by the reaction by means of Dean-Stark, adding water (500 ml) to the resulting reaction product, extracting the resulting product with toluene, washing the extraction solution successively with a saturated aqueous solution of sodium bicarbonate and water, distilling off the solvent, and distilling the residue under reduced pressure, to obtain 3-fluoro-4-trifluoromethoxyphenetylbromide (68.3 g, 238 mmol). Yield: 30.7%.

(Fifth step)

A Grignard reagent prepared from the above 3-fluoro-4-trifluoromethoxyphenetylbromide (1.64 g, 5.71 mmol) and dried Mg (0.14 g, 5.76 mmol) in ether (10 ml) was cooled down to 0° C., followed by adding thereto Ni acetylacetonate (0.10 g, 0.39 mmol), dropwise adding a 20 ml ether solution of 4-(3,5-difluorophenyl-4-iodo)-1-(3-fluoropropyl)cyclohexane (2.12 g, 5.73 mmol) prepared at the third step, stirring the reaction solution at 0° C. for one hour, heating it up to room temperature, stirring it for 3 hours, adding the resulting reaction solution to 6N HCl, extracting the resulting product with toluene, washing the extraction solution successively with a saturated aqueous solution of sodium bicarbonate and water, drying the organic layer over magnesium sulfate, distilling off the solvent, purifying the residue according to column chromatography treatment using toluene as a developing solvent on silica gel, and recrystallizing from a mixed solvent of heptane with ethanol, to obtain 1-(4-(3-fluoropropyl)cyclohexyl)-3,5-difluoro-4-(2-(3-fluoro-4-trifluoromethoxyphenyl)ethyl)benzene (320 mg, 0.692 mmol). Yield: 12.0%. The data of 1H-NMR well supported its structure.

EXAMPLE 4

Preparation of 1-(4-(4-(3-fluoropropyl)cyclohexyl)cyclohexyl)-3,5-difluoro-4-(3-fluoro-4-trifluoromethoxyphenyl)benzene (in the formula (1), n=3, ring E=G=1,4-cyclohexylene, L=3,5-difluoro-1,4-phenylene, ring Z=3-fluoro-1,4-phenylene, k=l=m=0, Q=—O—and Y=CF$_3$) (Compound No. 240).

(First step)

A 500 ml THF solution of bicyclohexanedione monopropyleneketal was dropwise added at room temperature to a Grignard reagent prepared from 3,5-difluorophenylbromide (107.1 g, 555 mmol) and dried Mg (14.0 g, 575 mmol) in THF (600 ml), followed by stirring the mixture at the same temperature for 5 hours, cooling the reaction solution to 0° C., adding thereto a saturated aqueous solution of NH$_4$Cl, extracting the resulting product with ethyl acetate, washing the extraction solution with water, drying the organic layer over magnesium sulfate, distilling off the solvent, to obtain yellow crystals (158 g), adding thereto toluene (700 ml) and 5% paratoluenesulfonic acid (7.9 g), refluxing the mixture for 9 hours, further 2 hours before completion of the reflux, adding propylene glycol (37 g) and 5% paratoluenesulfonic acid (8.3 g) into the system, washing the reaction solution successively with 6N HCl, a saturated aqueous solution of sodium bicarbonate and water, drying the organic layer over magnesium sulfate, distilling off the solvent, and purifying the resulting residue (169 g) according to column chromatography treatment using toluene/ethyl acetate (1/9) as a developing solvent, on silica gel, to obtain 4-(3,5-difluorophenyl)-3-cyclohexenyl-1-cyclohexanone propyleneketal (114 g, 327 mmol). Yield: 56.9%.

(Second step)

The above 4-(3,5-difluorophenyl)-3-cyclohexenyl-1-cyclohexanone propyleneketal (114 g, 327 mmol) was hydrogenated in a mixed solvent of ethyl acetate with ethanol in the presence of Raney Ni catalyst (44.8 g), followed by filtering off the catalyst, distilling off the solvent under reduced pressure, adding to the residue, formic acid (50.0 g, 1.09 mol) and toluene (300 ml), refluxing the mixture for 4 hours, adding water to the reaction solution, washing the organic layer successively with a saturated aqueous solution of sodium bicarbonate and water, drying over magnesium sulfate, distilling off toluene under reduced pressure, and purifying the residue according to column chromatography treatment using toluene as a developing solvent, on silica gel, to obtain 4-(3,5-difluorophenyl)cyclohexyl-1-cyclohexanone (56.8 g, 194 mmol). Yield: 59.3%.

(Third step)

THF (250 ml) was added to 3-fluoropropyltriphenylphosphine bromide (36.1 g, 89.5 mmol) prepared at the second step of Example 1, followed by cooling the mixture down to −50° C. in nitrogen gas atmosphere, adding to the mixture, a 100 ml THF solution of potassium-t-butoxide (10.0 g, 89.5 mmol), stirring the mixture for 3 hours, dropwise adding to the reaction solution, a 200 ml THF solution of 4-(3,5-difluorophenyl)cyclohexyl-1-cyclohexanone (20.0 g, 68.9 mmol) prepared at the second step, stirring the mixture at the same temperature for one hour, heating the mixture up to room temperature, stirring for 4 hours, adding water (1 l) to the reaction solution, extracting the resulting product with toluene, washing the extraction solution with water, drying the organic layer over magnesium sulfate, distilling off the solvent, purifying the residue according to column chromatography treatment using toluene as a developing solvent, on silica gel, to obtain an yellow solution (12.99 g), hydrogenating it in the presence of a 5% Pd/C catalyst (1.20 g) in ethanol, distilling off the solvent, and purifying the residue using toluene as a developing solvent on silica gel, to obtain 4-(3-fluoropropylcyclohexyl)cyclohexyl)-3,5-difluorobenzene (8.33 g, 24.6 mmol). Yield: 35.7%.

(Fourth step)

THF (80 ml) was added to the above 4-(3-fluoropropylcyclohexyl)cyclohexyl-3,5-difluorobenzene (8.10 g, 23.9 mmol), followed by cooling the mixture down to −50° C. in nitrogen gas atmosphere, dropwise adding thereto a hexane solution (16.9 ml, 28.7 mmol) of 1.63N normal butyllithium by means of a syringe, stirring the mixture at the same temperature for one hour, further dropwise adding a THF solution (58.4 ml, 29.2 mol) of 0.5 mol zinc chloride, heating the reaction solution up to room temperature, further stirring for 2 hours, adding to the reaction solution, tetraxistriphenylphosphine palladium (0.72 g, 622 mol), dropwise adding 3-fluoro-4-trifluoromethoxyphenylbromide (7.44 g, 28.7 mmol), refluxing the mixture for 2 hours, adding to the reaction solution, 6N HCl, extracting the product with ethyl acetate, washing the extraction solution successively with a saturated aqueous solution of sodium bicarbonate and water, drying the organic layer over magnesium sulfate, distilling off the solvent, purifying the residue (13.9 g) according to column chromatography treatment using heptane as a developing solvent on silica gel, and recrystallizing from a mixed solvent of heptane with ethanol, to obtain 1-(4-(4-(3-fluoropropyl)cyclohexyl)cyclohexyl)-3,5-difluoro-4-(3-fluoro-4-trifluoromethoxyphenyl)benzene (1.31 g, 2.54 mmol). Yield: 10.6%. C-N point: 78.5° C. N-I point: 224.5° C.

1H-NMR(CDCl$_3$) δ(ppm): 7.37 (t, 3H), 6.85 (d, 2H), 4.69 (t, 1H), 4.16 (t, 1H), 2.46 (m, 1H), 2.02–0.81 (m, 23H).

EXAMPLE 5

Preparation of 1-(2-(4-(3-fluoropropyl)cyclohexyl)ethyl)-3,5-difluoro-4-(3-fluoro-4-trifluoromethoxyphenyl)benzene (in the formula (1), n=3, ring E=1,4-cyclohexylene, G=covalent bond, L=3,5-difluoro-1,4-phenylene, ring Z=3-fluoro-1,4-phenylene, k=1, l=0, m=0, Q=—O—, Y=CF$_3$) (compound No. 77)

(First step)

THF (50 ml) was added to 4-(3,5-difluorophenetyl)-1-(3-fluoropropyl)cyclohexane (5.0 g, 17.6 mmol) prepared in the same manner as in Example 1, followed by cooling the mixture down to −50° C. in a nitrogen gas atmosphere, dropwise adding thereto a hexane solution (13 ml, 21.8 mmol) of 1.68N normal-butyllithium by means of a syringe, stirring the mixture at the same temperature for one hour, dropwise adding a THF solution (43.6 ml, 21.8 mmol) of zinc chloride (0.5 mol/l), heating the reaction product up to room temperature, further stirring it for 2 hours, adding to the reaction solution, tetrakistriphenylphosphine palladium (500 mg) as a catalyst, dropwise adding 3-fluoro-4-trifluoromethoxybromobenzene (5.64 g, 21.8 mmol), refluxing the mixture for 2 hours, adding the reaction solution to cooled 6N HCl, extracting the resulting product with toluene, washing the extraction solution successively with a saturated, aqueous solution of sodium bicarbonate, and water, drying over magnesium sulfate, distilling off the solvent, to obtain an yellow suspension (7.7 g), purifying it according to column chromatography treatment using toluene/heptane (1:1) as a developing solvent, on silica gel, and recrystallizing to obtain trans form of 1-(2-(4-(3-fluoropropyl)cyclohexyl)ethyl)-3,5-difluoro-4-(3-fluoro-4-trifluoromethoxyphenyl)benzene (0.58 g, 1.25 mmol). Yield: 7.1%, C-I point: 44.8° C., (N-I point: 13.6° C.). 1H-NMR (CDCl3) δ(ppm): 7.38~6.77 (m, 5H), 4.69 (t, 1H), 4.16 (t, 1H), 2.65 (t, 2H), 1.84~0.93 (m, 16H).

EXAMPLE 6

1-(2-(4-(4-(3-fluoropropyl)cyclohexyl)cyclohexyl)ethyl)-4-trifluoromethylbenzene (in the formula (1), n=3, ring E=G=1,4-cyclohexylene, L=covalent bond, ring Z=1,4-phenylene, k=l=0, m=1, Q=covalent bond, Y=CF$_3$) (Compound No. 18).

(First step)

THF (1 l) was added to methoxymethyltriphenylphosphine chloride (128 g, 370 mmol), followed by adding to the mixture, potassium-t-butoxide (41.5 g, 370 mmol) at 0° C., stirring the mixture at the same temperature for 3 hours, dropwise adding to the reaction solution, a 500 ml THF solution of commercially available 4-trifluoromethylbenzaldehyde (50.0 g, 287 mmol), stirring the mixture at the same temperature for one hour, stirring it at room temperature for 3 hours, adding water (1.5 l) to the reaction solution, extracting the resulting product with ethyl acetate, washing the organic layer successively with a saturated aqueous solution of sodium bicarbonate and water, drying over magnesium sulfate, distilling off the solvent, purifying the resulting yellow solution according to column chromatography treatment using heptane/ethyl acetate (3:2) as a developing solvent, on silica gel, and distilling the purified substance under reduced pressure by means of Vigoureux tube, to obtain 1-trifluoromethyl-4-(2-methoxyvinyl)benzene (19.5 g, 96.5 mmol) (b.p. 93.5° C. under 9 Torr). Yield: 33.6%.

(Second step)

The above 1-trifluoromethyl-4-(2-methoxyvinyl)benzene (19.5 g, 96.5 mmol) was dissolved in acetone (100 ml), followed by adding 6N HCl (100 ml) to the solution, stirring the mixture for 5 hours, extracting the resulting product with ethyl acetate, washing the organic layer successively with a saturated, aqueous solution of sodium bicarbonate and water, drying over magnesium sulfate and distilling off the solvent, to obtain 4-trifluoromethylbenzylaldehyde (17.5 g, 93.0 mmol). Yield: 96.4%.

(Third step)

Ethanol (200 ml) was added to the above 4-trifluoromethylbenzylaldehyde (17.5 g, 93 mmol), followed by cooling the mixture down to 0° C. in a nitrogen atmosphere, adding thereto sodiumboronhydride (1.78 g, 47.1 mmol) so that the liquid temperature might not exceed 10° C., stirring the mixture at 0° C. for 2 hours, extracting the resulting product with ethyl acetate, washing the organic layer successively with a saturated, aqueous solution of sodium bicarbonate and water, drying over magnesium sulfate, distilling off the solvent, adding an aqueous solution of HBr (47%) (100 ml) to the residue (about 18 g), refluxing the mixture for 7 hours and distilling under reduced pressure by means of Vigoureux tube, to obtain 2-(4-trifluoromethylphenyl) bromoethane (19.5 g, 77.1 mmol) (b.p.: 94° C. under 9 Torr). Yield: 82.9%.

(Fourth step)

A Grignard reagent prepared from the above 2-(4-trifluoromethylphenyl)bromoethane (19.5 g, 77.1 mmol and dried Mg (1.90 g, 78.2 mmol) in an ether solvent (100 ml), was cooled down to 0° C., followed by dropwise adding to the agent, a 100 ml ether solution of bicyclohexanedione monopropyleneketal (19.4 g, 76.9 mmol), heating the mixture up to room temperature, stirring it for 3 hours, adding this reaction solution to 6N HCl (100 ml), extracting the resulting product with toluene, washing the extraction solution successively with a saturated, aqueous solution of sodium bicarbonate and water, drying over magnesium sulfate, distilling off the solvent, adding toluene (300 ml) and Amberlist (1.5 g) to the resulting pale-yellow, oily substance (about 30 g), refluxing the mixture for 4 hours, while removing water formed by the reaction by Dean-Stark, filtering off the solvent, purifying thr residue according to column chromatography treatment using ethyl acetate/ toluene (1/1) as a developing solvent, on silica gel, to isolate 4-(4-oxocyclohexyl)-1-(2-(4-trifluoromethylphenyl)ethyl)-1-cyclohexene propyleneacetal (20.0 g, 48.9 mmol), hydrogenating the compound in the presence of a catalyst of 5% Pd/C (1.0 g) in ethanol solvent, filtering off the catalyst, distilling off the solvent under reduced pressure, adding formic acid (20.0 g, 444 mmol) and toluene (100 ml), to the residue, refluxing the mixture for 5 hours, washing the organic layer successively with a saturated, aqueous solution of sodium bicarbonate and water, drying over magnesium sulfate, purifying the residue according to column chromatography treatment using ethyl acetate/toluene (1/3) as a developing solvent, on silica gel, recrystallizing the purified product from heptane, to isolate 4-(4-oxocyclohexyl)-1-(2-4-trifluoromethylphenyl)ethyl)cyclohexane (2.7 g, 7.7 mmol). The yield of this product from bicyclohexanedione monopropyleneketal was 10.0%.

(Fifth step)

THF (70 ml) was added to 1,3-dioxan-2-ylethyltriphenylphosphinebromide (6.80 g, 14.9 mmol), followed by adding to the mixture, potassium-t-butoxide (1.68 g, 14.9 mmol) at 0° C., stirring the mixture at the same temperature for 3 hours, dropwise adding to the reaction solution, a 10 ml THF solution of the above 4-(4-oxocyclohexyl)-1-(2-(4-trifluoromethylphenyl)ethyl) cyclohexane (2.7 g, 7.7 mmol), stirring the mixture at the same temperature for one hour, further stirring at room temperature for 3 hours, adding water (50 ml) to the reaction solution, extracting the resulting product with ethyl acetate, washing the organic layer successively with a saturated, aqueous solution of sodium bicarbonate and water, drying over magnesium sulfate, distilling off the solvent, purifying the resulting residue according to column chromatography treatment using heptane/ethyl acetate (3/1) as a developing solvent, on silica gel, distilling off the solvent, hydrogenating the residue (3.2 g) in the presence of a catalyst of 5% Pd/C (0.15 g), in ethanol solvent, filtering off the catalyst distilling off the solvent under reduced pressure, and recrystallizing the residue from heptane/ethanol (5/1), to obtain 4-(4-(1,3-dioxan-2-ylethyl)cyclohexyl)-1-(2-(4-trifluoromethylphenyl)ethyl)cyclohexane (1.46 g, 3.23 mmol). The yield of this product from 4-(4-oxocyclohexyl)-1-(2-(4-trifluoromethylphenyl)ethyl)cyclohexane was 42%.

(Sixth step)

Formic acid (1.5 g, 33 mmol) and toluene (10 ml) were added to the above 4-(4-(1,3-dioxan-2-ylethyl)cyclohexyl)-1-(2-(4-trifluoromethylphenyl)ethyl)cyclohexane (1.46 g, 3.23 mmol), followed by refluxing the mixture for 5 hours, washing the organic layer successively with a saturated, aqueous solution of sodium bicarbonate and water, drying over magnesium sulfate, and distilling off the solvent, to obtain 3-(4-(4-(2-(4-trifluoromethylphenyl)ethyl)cyclohexyl)cyclohexyl)propanal (1.21 g, 3.07 mmol). Yield: 95.0%.

(Seventh step)

Ethanol (10 ml) was added to the above 3-(4-(4-(2-(4-trifluoromethylphenyl)ethyl)cyclohexyl)cyclohexyl)propanal (1.21 g, 3.07 mmol), followed by cooling the mixture down to 0° C. in a nitrogen gas atmosphere, adding thereto, sodiumboronhydride (0.13 g, 3.43 mmol) so that the solution temperature could not exceed 10° C., stirring the mixture at 0° C. for 2 hours, extracting the resulting product with ethyl acetate, washing the organic layer successively with a saturated, aqueous solution of sodium bicarbonate and water, drying over magnesium sulfate, and distilling off the solvent, to obtain 3-(4-(4-(2-(4-trifluoromethylphenyl)ethyl)cyclohexyl)cyclohexyl)propanol (1.20 g, 3.03 mmol). The yield was 98.7%.

(Eighth step)

Dimethoxyethane (10 ml) was added to the above 3-(4-(4-(2-(4-trifluoromethylphenyl)ethyl)cyclohexyl)cyclohexyl)propanol (1.20 g, 3.03 mmol), followed by dropwise adding thereto diethylaminosulfur trifluoride (DAST) (1.13 g, 7.01 mmol), refluxing the mixture for 5 hours, extracting the resulting product with toluene, washing the organic layer successively with a saturated, aqueous solution of sodium bicarbonate and water, drying over magnesium sulfate, distilling off the solvent, purifying the residue according to column chromatography treatment using heptane as a developing solvent, on silica gel, distilling off the solvent, and recrystallizing the residue from ethanol/heptane (9/1), to isolate only trans-form of 1-(2-(4-(4-(3-fluoropropyl)cyclohexyl)cyclohexyl)ethyl)-4-trifluoromethylbenzene (0.60 g, 1.5 mmol). Yield: 49.5%. $S_B$-I point: 118.9° C.

1H-NMR (CDC 13) δ(ppm): 7.52 (d, 2H), 7.27 (d, 2H), 4.68 (t, 1H), 4.16 (t, 1H), 2.68 (t, 2H), 1.75–0.99 (m, 26H).

EXAMPLE 7

Preparation of 1-(2-(4-(4-(3-fluoropropyl)cyclohexyl)cyclohexyl)ethyl)-4-trifluoromethoxybenzene (in the formula (1), n=3, ring E=1,4-cyclohexylene, G=covalent bond, L=1,4-cyclohexylene, ring Z=1,4-phenylene, k=l=0, m=1, Q=—O—, Y=CF$_3$) (Compound No. 19)

(First step)

THF (1.8 l) was added to methoxymethyltriphenylphosphine chloride (350 g, 1.02 mol), followed by adding to the mixture, potassium-t-butoxide (114 g, 1.02 mol), stirring the mixture at the same temperature, for 3 hours, dropwise adding to the reaction solution, a 750 ml THF solution of commercially available 4-trifluoromethoxybenzaldehyde (150.0 g, 0.79 mol), stirring the mixture at the same temperature for one hour, further stirring it at room temperature for 3 hours, adding water (1.5 l) to the reaction solution, extracting the resulting product with ethyl acetate, washing the organic layer successively with a saturated, aqueous solution of sodium bicarbonate and water, drying over magnesium sulfate, distilling off the solvent, purifying the resulting yellow solution according to column chromatography treatment using heptane/ethyl acetate (3/2) as a developing solvent, on silica gel, and distilling the purified product under reduced pressure, by means of Vigoureux tube, to obtain 1-trifluoromethoxy-4-(2-methoxyvinyl)benzene (138 g, 0.63 mol). (b.p. 91° C. under 9 Torr). Yield: 79.7%.

(Second step)

The above 1-trifluoromethoxy-4-(2-methoxyvinyl)benzene (138 g, 0.63 mol) was dissolved in acetone (500 ml), followed by adding 6N HCl (500 ml) to the solution, stirring the mixture for 5 hours, extracting the resulting product with ethyl acetate, washing the organic layer successively with a saturated aqueous solution of sodium bicarbonate and water, drying over magnesium sulfate, and distilling off the solvent, to obtain 4-trifluoromethoxybenzylaldehyde (123 g, 0.60 mol). Yield: 95.2%.

(Third step)

Ethanol (1.5 l) was added to the above 4-trifluoromethoxybenzylaldehyde (123 g, 0.60 mol), followed by cooling the mixture down to 0° C. in a nitrogen atmsophere, adding thereto sodiumboronhydride (11.7 g, 0.31 mol) so that the liquid temperature might not exceed 10° C., stirring the mixture at 0° C. for 2 hours, extracting the resulting product with ethyl acetate, washing the organic layer successively with a saturated, aqueous solution of sodium bicarbonate and water, drying over magnesium sulfate, distilling off the solvent, adding an aqueous solution of HBr (47%) (750 ml ) to the residue, refluxing the mixture for 7 hours, and distilling it under reduced pressure by means of Vigoureux tube, to obtain 2-(4-trifluoromethoxyphenyl)bromoethane (52.8 g, 0.20 mol) (b.p.: 52.0° C. under 1 Torr). Yield: 33.3%.

(Fourth step)

A Grignard reagent prepared from the above 2-(4-trifluoromethoxyphenyl)bromoethane (25.0 g, 92.9 mmol) and dried Mg (2.26 g, 93.0 mmol) in 100 ml ether solvent, was cooled down to 0° C., followed by dropwise adding thereto a 100 ml ether solution of bicyclohexanedione monopropyleneketal (22.0 g, 87.2 mmol), heating the mixture up to room temperature, stirring it for 3 hours, adding the reaction solution to 6N HCl (100 ml), extracting the resulting product with toluene, washing the extraction solution successively with a saturated, aqueous solution of sodium bicarbonate and water, drying over magnesium sulfate, distilling off the solvent, adding toluene (300 ml) and Amberlist (2.0 g) to the residue, refluxing for 5 hours, while removing water formed by the reaction by means of Dean-Stark, filtering off Amberlist, distilling off the solvent, purifying the residue according to column chromatography treatment using ethyl acetate/toluene (1/2) as a developing solvent, on silica gel, to isolate 4-(4-oxocyclohexyl)-1-(2-(4-trifluoromethoxyphenyl)ethyl)-1-cyclohexene propylene acetal (22.2 g, 52.3 mmol),hydrogenating it in the presence of a 5% Pd/C catalyst (1.2 g) in ethanol solvent, filtering off the catalyst after the reaction, distilling off the solvent under reduced pressure, adding to the residue, formic acid (20.0 g, 444 mmol) and toluene (100 ml), refluxing the mixture for 5 hours, washing the organic layer successively with a saturated, aqueous solution of sodium bicarbonate and water, drying over magnesium sulfate, distilling off the solvent, purifying the residue according to column chromatography treatment using ethyl acetate/toluene (1/3) as a developing solvent, on silica gel and recrystallizing the purified substance from heptane, to isolate 4-(4-oxocyclohexyl)-1-(2-(4-trifluoromethoxyphenyl)ethyl) cyclohexane (5.7 g, 15.6 mmol). The yield of this product from bicyclohexanedione monopropyleneketal was 17.9%.

(Fifth step)

THF (100 ml) was added to 1,3-dioxan-2-ylethyltriphenylphosphinebromide (10.0 g, 21.9 mmol), followed by adding thereto potassium-t-butoxide (2.46 g, 21.9 mmol), stirring the mixture at the same temperature for 3 hours, dropwise adding to the reaction solution, a 20 ml THF solution of the above 4-(4-oxocyclohexyl)-1-(2-(4-trifluoromethoxyphenyl)ethyl)cyclohexane (5.7 g, 15.6 mmol), stirring the mixture at the same temperature for one hour, stirring for 3 hours at room temperature, adding water (100 ml) to the reaction solution, extracting the product with ethyl acetate, washing the organic layer successively with a saturated aqueous solution of sodium bicarbonate and water, drying over magnesium sulfate, distilling off the solvent, purifying the resulting residue according to column chromatography treatment using heptane/ethyl acetate (3/1) as a developing solvent, on silica gel, distilling off the solvent, hydrogenating the residue (5.1 g) in the presence of a catalyst of 5% Pd/C (0.30 g) in an ethanol solution, filtering off the catalyst, distilling off the solvent under reduced pressure, and recrystallizing the residue from heptane/ethanol (5/1), to obtain 4-(4-(1,3-dioxan-2-ylethyl)cyclohexyl)-1-(2-(4-trifluoromethoxyphenyl)ethyl) cyclohexane (3.25 g, 6.94 mmol). The yield of this product from 4-(4-oxocyclohexyl)-1-(2-(4-trifluoromethoxyphenyl) ethyl)cyclohexane was 44.5%.

(Sixth step)

Formic acid (3.0 g, 66 mmol) and toluene (20 ml) were added to the above 4-(4-(1,3-dioxan-2-ylethyl)cyclohexyl)-1-(2-(4-trifluoromethoxyphenyl)ethyl)cyclohexane (3.25 g, 6.94 mmol), followed by refluxing the mixture for 5 hours, washing the organic layer successively with a saturated, aqueous solution of sodium bicarbonate and water, drying over magnesium sulfate, and distilling off the solvent, to obtain 3-(4-(4-(2-(4-trifluoromethoxyphenyl)ethyl) cyclohexyl)cyclohexyl)propanal (2.70 g, 6.58 mmol). Yield: 94.8%.

(Seventh step)

Ethanol (20 ml) was added to the above 3-(4-(4-(2-(4-trifluoromethoxyphenyl)ethyl)cyclohexyl)cyclohexyl) propanal (2.70 g, 6.58 mmol), followed by cooling the mixture down to 0° C. in a nitrogen gas atmosphere, adding thereto, sodiumboronhydride (0.13 g, 3.43 mmol) so that the liquid temperature could not exceed 10° C., stirring the mixture at 0° C. for 2 hours, extracting the resulting product with ethyl acetate, washing the organic layer successively with a saturated aqueous solution of sodium bicarbonate and water, drying over magnesium sulfate, distilling off the solvent, and recrystallizing the residue from heptane, to obtain 3-(4-(4-(2-(4-trifluoromethoxyphenyl)ethyl)cyclohexyl)cyclohexyl) propanol (2.10 g, 5.09 mmol). Yield: 77.4%.

(Eighth step)

Dimethoxyethane (20 ml) was added to the above 3-(4-(4-(2-(4-trifluoromethoxyphenyl)ethyl)cyclohexyl) cyclohexyl)propanol (2.10 g, 5.09 mmol), followed by dropwise adding thereto diethylaminosulfurtrifluoride (DAST) (1.73 g, 10.7 mmol), refluxing the mixture for 5 hours, extracting the resulting product with toluene, washing the organic layer successively with a saturated, aqueous solution of sodium bicarbonate and water, drying over magnesium sulfate, distilling off the solvent, purifying the residue according to column chromatography treatment using heptane/toluene (3/1) as a developing solvent, on silica gel, distilling off the solvent, and recrystallizing the residue from ethanol, to isolate only tran-form of 1-(2-(4-(4-(3-fluoropropyl)cyclohexyl)cyclohexyl)ethyl)-4-trifluoromethylbenzene (0.88 g, 2.12 mmol). Yield: 41.7%. $S_B$-N point: 73.8° C., N-I point: 131.8° C.

1H-NMR (CDC 13) δ(ppm): 7.20 (d, 4H), 4.68 (t, 1H), 4.15 (t, 1H), 2.62 (t, 2H), 1.75–0.99 (m, 26H).

EXAMPLE 8

Preparation of 1-(4-(3-fluoropropyl)cyclohexyl)-3-fluoro-4-trifluoromethoxybenzene (in the formula (1), n=3, ring E=1,4-cyclohexylene, G, L=covalent bond, ring Z=3-fluoro-1,4-phenylene, k=1, l=m=0, Q=—O—, Y=CF$_3$) (Compound No. 13)

(First step)

THF (3 l) was added to 1,3-dioxan-2-ylethyltriphenylphosphinebromide (500 g, 1.09 mol), followed by adding to the mixture, potassium-t-butoxide (122 g, 1.09 mol) at 0° C., stirring the mixture at the same temperature for 3 hours, dropwise adding to the reaction solution, a 700 ml THF solution of cyclohexanedionemonoethyleneketal (141.9 g, 0.91 mol), stirring the mixture at the same temperature for one hour, further stirring it at room temperature for 3 hours, adding water (2 l) to the reaction solution, extracting the resulting product with ethyl acetate, washing the organic layer successively with a saturated, aqueous solution of sodium bicarbonate and water, drying over magnesium sulfate, distilling off the solvent, purifying the residue according to column chromatography treatment using heptane/ethyl acetate (1/1) as a developing solvent, on silica gel, distilling off the solvent, hydrogenating the residue in the presence of 5% Pd/C catalyst (3.0 g) in an ethanol solution, filtering off the catalyst and distilling off the solvent under reduced pressure, to obtain 4-oxo-1-(1,3-dioxan-2-ylethyl)cyclohexane monoethyleneketal (98 g, 0.38 mol). The yield of this product from cyclohexanedionemonoethyleneketal was 42%.

(Second step)

3N HCl (200 ml) and acetone (200 ml) were added to the above 4-oxo-1-(1,3-dioxan-2-ylethyl)cyclohexane ethyleneacetal (60 g, 234 mmol), followed by stirring the mixture for 5 hours, extracting the resulting product with ethyl acetate, washing the organic layer successively with a saturated, aqueous solution of sodium bicarbonate and water, drying over magnesium sulfate, distilling off the solvent, purifying the residue according to column chromatography treatment using heptane/ethyl acetate (3/2) as a developing solvent, on silica gel, and distilling off the solvent, to obtain 4-oxo-1-(1,3-dioxan-2-ylethyl)cyclohexane (35.5 g, 167 mmol). Yield: 71.3%.

(Third step)

60% Sodium hydride (7.12 g, 178 mmol) was added to dimethoxyethane (280 ml) in a nitrogen gas atmosphere, followed by stirring the mixture at room temperature for 10 minutes, dropwise adding to the solution, diethylphosphonoacetic acid ethyl (40.0 g, 178 mmol), stirring the mixture at the same temperature till completion of evolution of hydrogen gas, dropwise adding the above 4-oxo-1-(1,3-dioxan-2-ylethyl)cyclohexane (30.0 g, 141 mmol) so that the liquid temperature might not exceed 30° C., stirring the mixture for 30 minutes, adding the reaction solution to water (300 ml), extracting the resulting product with ether, drying the organic layer over magnesium sulfate, distilling off the solvent, hydrogenating the resieue (36.6 g) in the presence of 5% Pd/C catalyst (1.8 g), in an ethanol solution, filtering off the catalyst, and distilling off the solvent under reduced catalyst, to obtain ethyl 2-(4-(1,3-dioxan-2-ylethyl)cyclohexylethanoate (30.2 g, 106 mmol). The yield of this product from 4-oxo-1-(1,3-dioxan-2-ylethyl)cyclohexane was 75.1%.

(Fourth step)

Toluene (450 ml) was added to the above ethyl 2-(4-(1,3-dioxan-2-ylethyl)cyclohexylethanoate (30.2 g, 106 mmol) in a nitrogen gas atmosphere, followed by cooling the mixture down to −65° C., dropwise adding to the solution, a toluene solution of diisobutylaluminum hydride (1.01 mol/l) 120 ml (121 mmol), stirring the mixture at the same temperature for 45 minutes, dropwise adding a saturated aqueous solution of ammonium chloride (33 ml), heating the mixture up to room temperature, adding ether (100 ml) to the reaction solution, stirring the mixture at the temperature for 1.5 hours, adding magnesium sulfate (10 g), stirring the mixture for one hour, filtering off the reaction solution, washing the filtrate with water, drying over magnesium sulfate, and distilling off the solvent, to obtain 2-(4-(1,3-dioxan-2-ylethyl)cyclohexyl)ethanol (22.0 g, 91.5 mmol). Yield: 86.3%.

(Fifth step)

A Grignard reagent prepared from 3-fluoro-4-trifluoromethoxybromobenzene (9.3 g, 38.7 mmol) and dried Mg (0.97 g 39.9 mmol) in a 50 ml ether solvent, was cooled down 0° C., followed by dropwise adding thereto, a 40 ml ether solution of the above 2-(4-(1,3-dioxan-2-ylethyl)cyclohexyl)ethanol (6.3 g, 26.2 mmol), heating the mixture up to room temperature, stirring it for 3 hours, adding this reaction solution to 6N HCl (100 ml), extracting the resulting product with ethyl acetate, washing the extraction solution successively with a saturated aqueous solution of sodium bicarbonate and water, drying over MgSO$_4$, distilling off the solvent, adding toluene (150 ml) and Amberlist (3.0 g) to the residue, refluxing for 5 hours, while removing water formed by the reaction by means of Dean-Stark, adding trimethylene glycol (1.0 g, 13.1 mmol), further refluxing for one hour, filtering off Amberlist, distilling off the solvent, purifying the residue according to column chromatography treatment using ethyl acetate/toluene (1/2) as a developing solvent, on silica gel, and distilling off the solvent, to isolate 1-(2-(4-(1,3-dioxan-2-ylethyl)cyclohexyl)vinyl-3-fluoro-4-trifluoromethoxybenzene (5.5 g, 13.7 mmol). The yield of this product from 2-(4-(1,3-dioxan-2-ylethyl)cyclohexyl)ethanol was 52.3%.

(Sixth step)

The above 1-(2-(4-(1,3-dioxan-2-ylethyl)cyclohexyl)vinyl-3-fluoro-4-trifluoromethoxybenzene (5.5 g, 13.7 mmol) was hydrogenated in the presence of 5% Pd/C catalyst (0.3 g) in an ethanol solution, followed by filtering off the catalyst, distilling off the solvent under reduced pressure, adding formic acid (2.8 g, 60.8 mmol) and toluene (50 ml) to the residue, refluxing the mixture for 5 hours, washing the organic layer successively with a saturated, aqueous solution of sodium bicarbonate and water, drying over MgSO$_4$, and distilling off the solvent, to obtain 3-(4-(2-(3-fluoro-4-trifluoromethoxyphenyl)ethyl)cyclohexyl)propanal (1.76 g, 5.1 mmol). The yield of this product from 1-(2-(4-(1,3-dioxan-2-ylethyl)cyclohexyl)vinyl-3-fluoro-4-trifluoromethoxybenzene was 37.2%.

(Seventh step)

Ethanol (12 ml) was added to the above 3-(4-(2-(3-fluoro-4-trifluoromethoxyphenyl)ethyl)cyclohexyl)propanal (1.76 g, 5.1 mmol), followed by cooling the mixture down to 0° C. in a nitrogen gas atmosphere, adding to the mixture, sodiumboron hydride (0.19 g, 5.0 mmol) so that the liquid temperature might not exceed 10° C., stirring the mixture at 0° C. for 2 hours, extracting the resulting product with ethyl acetate, washing the organic layer successively with a saturated, aqueous solution of sodium bicarbonate and water, drying over MgSO$_4$, distilling off the solvent, and recrystallizing the residue with heptane, to obtain 3-(4-(2-(3-fluoro-4-trifluoromethoxyphenyl)ethyl)cyclohexyl)propanol (1.52 g, 4.4 mmol). Yield: 86.3%.

(Eighth step)

Dimethoxyethane (15 ml) was added to the above 3-(4-(2-(3-fluoro-4-trifluoromethoxyphenyl)ethyl)cyclohexyl)propanol (1.52 g, 4.4 mmol), followed by-dropwise adding DAST (1.40 g, 8.7 mmol), refluxing the mixture for 5 hours, extracting the resulting product with toluene, washing the organic layer successively with a saturated aqueous solution of sodium bicarbonate and water, drying over MgSO$_4$, distilling off the solvent, purifying the residue according to column chromatography treatment using heptane as a developing solvent, on silica gel, distilling off the solvent, and recrystallizing the residue from ethanol, to isolate 1-(3-fluoropropyl)cyclohexyl)-3-fluoro-4-trifluoromethoxybenzene (0.12 g, 0.34 mmol). Yield: 7.7%. Its clearing point measured by PERKIN-ELMER 7 series Thermal Analysis System was −5.89° C.

1H-NMR (CDC 13) δ(ppm): 7.26–6.89 (m, 3H, 4.68 (t, 1H), 4.15 (t, 1H), 2.61 (t, 2H), 1.82–0.91 (m, 16H).

Example 9

Preparation of 1-(2-(4-(3-fluoropropyl)cyclohexyl)ethyl)-3,5-difluoro-4-(4-(1,1,2,3,3,3-hexafluoropropyloxy)phenyl)benzene (in the formula (1), n=3, ring E=1,4-cyclohexylene, G=covalent bond, L=3,5-difluoro-1,4-phenylene, ring Z=1,4-phenylene, k=1, l=0, m=0, Q=—O—, Y=CF$_2$CFHCF$_3$)
(Compound No. 74)

(First step)

THF (50 ml) was added to 4-(3,5-difluorophenetyl)-1-(3-fluoropropyl)cyclohexane (5.0 g, 17.6 mmol) prepared in the same manner as the process carried out in Example 1, followed by cooling the mixture down to −50° C. in nitrogen gas atmosphere, dropwise adding thereto a hexane solution (14 ml, 22.8 mmol) of 1.63N normal butyllithium by means of a syringe, stirring the mixture at the same temperature for one hour, dropwise adding a THF solution (45.6 ml, 22.8 mmol) of 0.5 mol zinc chloride, heating the resulting reaction product up to room temperature, further stirring it for 2 hours, adding to the reaction solution, tetraxistriphenylphosphinepalladium (500 g ) as a catalyst, dropwise adding 4-(1,1,2,3,3,3-hexafluoropropyloxy)bromobenzene (7.37 g, 22.8 mmol), refluxing the mixture for 2 hours, adding this reaction solution to cooled 6N HCl (50 ml), extracting the resulting product with toluene, washing the extraction liquid successively with a saturated, aqueous solution of sodium bicarbonate and water, drying over MgSO$_4$, distilling off the solvent, purifying the residue according to column chromatography treatment using toluene/heptane (1/1) as a developing solvent, on silica gel, and recrystallizing from ethanol, to obtain 1-(2-(4-(3-fluoropropyl)cyclohexyl)ethyl)-3,5-difluoro-4-4-(1,1,2,3,3,3-hexafluoropropyloxy)phenyl) benzene (1.25 g, 2.37 mmol). Yield: 13.5%.

The results of 1H-NMR well supported the structure.

Based upon Examples 1 to 9 and the detailed description of the present invention, it is possible to prepare the following compounds No. 1 to No. 286. In addition, the respective compounds are designated by extracting n, ring E, k, G, l, L, m, ring Z and group Q—Y as parameters in the compounds expressed by the formula (1). Further, designations H, B, M and D in the columns of ring E, G, L and ring Z among the parameters, respectively represent 1,4-cyclohexylene, 1,4-phenylene,

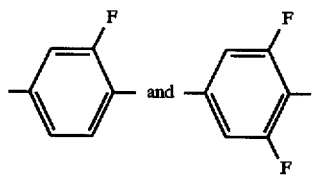

and the symbol, —in the columns of G and L represents covalent bond.

| Parameter No. | n | Ring E | G | L | Ring Z | k | l | m | Q—Y |
|---|---|---|---|---|---|---|---|---|---|
| 1 | 3 | B | — | — | B | 0 | 0 | 0 | CF$_3$ |
| 2 | 3 | B | — | — | B | 0 | 0 | 0 | OCF$_3$ |
| 3 | 3 | B | — | — | M | 0 | 0 | 0 | CF$_3$ |
| 4 | 3 | B | — | — | M | 0 | 0 | 0 | OCF$_3$ |
| 5 | 3 | B | — | — | D | 0 | 0 | 0 | CF$_3$ |
| 6 | 3 | B | — | — | D | 0 | 0 | 0 | OCF$_3$ |
| 7 | 3 | B | — | — | B | 0 | 0 | 0 | OCF$_2$CFHCF$_3$ |
| 8 | 3 | B | — | — | B | 0 | 0 | 0 | CH$_2$CF$_3$ |
| 9 | 3 | B | — | — | M | 0 | 0 | 0 | OCH$_2$CF$_3$ |
| 10 | 3 | B | — | — | B | 0 | 0 | 0 | CF$_2$CF$_3$ |
| 11 | 5 | B | — | — | B | 0 | 0 | 0 | OCF$_3$ |
| 12 | 3 | H | — | — | B | 1 | 0 | 0 | CF$_3$ |
| 13 | 3 | H | — | — | M | 1 | 0 | 0 | OCF$_3$ |
| 14 | 3 | B | — | — | B | 1 | 0 | 0 | CF$_3$ |
| 15 | 3 | B | — | — | M | 1 | 0 | 0 | OCF$_3$ |
| 16 | 2 | H | — | H | B | 0 | 0 | 1 | CF$_3$ |
| 17 | 2 | H | — | H | B | 0 | 0 | 1 | OCF$_3$ S$_B$ 69 NI104 |
| 18 | 3 | H | — | H | B | 0 | 0 | 1 | CF$_3$ S$_B$ I 120 |
| 19 | 3 | H | — | H | B | 0 | 0 | 1 | OCF$_3$ S$_B$ N 74 NI 132 |
| 20 | 3 | H | — | H | D | 0 | 0 | 1 | CF$_3$ |
| 21 | 3 | H | — | H | M | 0 | 0 | 1 | OCF$_3$ |
| 22 | 3 | H | — | H | M | 0 | 0 | 1 | F |
| 23 | 3 | H | — | H | D | 0 | 0 | 1 | F |
| 24 | 3 | H | — | H | B | 0 | 0 | 1 | OCF$_2$CFHCF$_3$ |
| 25 | 3 | H | — | H | M | 0 | 0 | 1 | OCF$_2$CFHCF$_3$ |
| 26 | 3 | H | — | H | D | 0 | 0 | 1 | OCF$_2$CFHCF$_3$ |
| 27 | 3 | H | — | H | M | 0 | 0 | 2 | OCF$_3$ |
| 28 | 3 | H | — | H | D | 0 | 0 | 2 | CF$_3$ |
| 29 | 3 | H | — | H | M | 0 | 0 | 1 | OCF$_2$H |
| 30 | 5 | H | — | H | M | 0 | 0 | 1 | OCF$_3$ |
| 31 | 5 | H | — | H | D | 0 | 0 | 1 | CF$_3$ |
| 32 | 3 | H | — | H | B | 1 | 0 | 0 | CF$_3$ |
| 33 | 3 | H | — | H | B | 1 | 0 | 0 | OCF$_3$ |
| 34 | 3 | H | — | H | M | 1 | 0 | 0 | CF$_3$ |
| 35 | 3 | H | — | H | M | 1 | 0 | 0 | OCF$_3$ |

-continued

| Parameter No. | n | Ring E | G | L | Ring Z | k | l | m | Q—Y |
|---|---|---|---|---|---|---|---|---|---|
| 36 | 3 | H | — | H | D | 1 | 0 | 0 | CF$_3$ |
| 37 | 3 | H | — | H | D | 1 | 0 | 0 | OCF$_3$ |
| 38 | 3 | H | — | H | M | 1 | 0 | 0 | F |
| 39 | 3 | H | — | H | D | 1 | 0 | 0 | F |
| 40 | 3 | H | — | H | B | 1 | 0 | 0 | OCF$_2$CFHCF$_3$ |
| 41 | 3 | H | — | H | M | 1 | 0 | 0 | OCF$_2$CFHCF$_3$ |
| 42 | 3 | H | — | H | D | 1 | 0 | 0 | OCF$_2$CFHCF$_3$ |
| 43 | 3 | H | — | H | B | 1 | 0 | 0 | CH$_2$CF$_3$ |
| 44 | 3 | H | — | H | M | 1 | 0 | 0 | OCH$_2$CF$_3$ |
| 45 | 3 | H | — | H | B | 1 | 0 | 0 | CF$_2$CF$_3$ |
| 46 | 3 | H | — | H | B | 2 | 0 | 0 | OCF$_3$ |
| 47 | 3 | H | — | H | M | 2 | 0 | 0 | OCF$_3$ |
| 48 | 5 | H | — | H | B | 1 | 0 | 0 | OCF$_3$ |
| 49 | 3 | H | — | B | B | 1 | 0 | 0 | CF$_3$ |
| 50 | 3 | H | — | B | B | 1 | 0 | 0 | OCF$_3$ |
| 51 | 3 | H | — | B | B | 1 | 0 | 0 | OCF$_2$CFHCF$_3$ |
| 52 | 3 | H | — | B | M | 1 | 0 | 0 | CF$_3$ |
| 53 | 3 | H | — | B | M | 1 | 0 | 0 | OCF$_3$ |
| 54 | 3 | H | — | B | M | 1 | 0 | 0 | OCF$_2$CFHCF$_3$ |
| 55 | 3 | H | — | B | M | 1 | 0 | 0 | F |
| 56 | 3 | H | — | B | D | 1 | 0 | 0 | CF$_3$ |
| 57 | 3 | H | — | B | D | 1 | 0 | 0 | OCF$_3$ |
| 58 | 3 | H | — | B | D | 1 | 0 | 0 | OCF$_2$CFHCF$_3$ |
| 59 | 3 | H | — | B | D | 1 | 0 | 0 | F |
| 60 | 3 | H | — | M | B | 1 | 0 | 0 | CF$_3$ |
| 61 | 3 | H | — | M | B | 1 | 0 | 0 | OCF$_3$ |
| 62 | 3 | H | — | M | B | 1 | 0 | 0 | OCF$_2$CFHCF$_3$ |
| 63 | 3 | H | — | M | B | 1 | 0 | 0 | F |
| 64 | 3 | H | — | M | M | 1 | 0 | 0 | CF$_3$ |
| 65 | 3 | H | — | M | M | 1 | 0 | 0 | OCF$_3$ |
| 66 | 3 | H | — | M | M | 1 | 0 | 0 | OCF$_2$CFHCF$_3$ |
| 67 | 3 | H | — | M | M | 1 | 0 | 0 | F |
| 68 | 3 | H | — | M | D | 1 | 0 | 0 | CF$_3$ |
| 69 | 3 | H | — | M | D | 1 | 0 | 0 | OCF$_3$ |
| 70 | 3 | H | — | M | D | 1 | 0 | 0 | OCF$_2$CFHCF$_3$ |
| 71 | 3 | H | — | M | D | 1 | 0 | 0 | F |
| 72 | 3 | H | — | D | B | 1 | 0 | 0 | CF$_3$ |
| 73 | 3 | H | — | D | B | 1 | 0 | 0 | OCF$_3$ |
| 74 | 3 | H | — | D | B | 1 | 0 | 0 | OCF$_2$CFHCF$_3$ |
| 75 | 3 | H | — | D | B | 1 | 0 | 0 | F |
| 76 | 3 | H | — | D | M | 1 | 0 | 0 | CF$_3$ |
| 77 | 3 | H | — | D | M | 1 | 0 | 0 | OCF$_3$ CI 45 NI (13.6) |
| 78 | 3 | H | — | D | M | 1 | 0 | 0 | OCF$_2$CFHCF$_3$ |
| 79 | 3 | H | — | D | M | 1 | 0 | 0 | F |
| 80 | 3 | H | — | D | D | 1 | 0 | 0 | CF$_3$ C 184 |
| 81 | 3 | H | — | D | D | 1 | 0 | 0 | OCF$_3$ |
| 82 | 3 | H | — | D | D | 1 | 0 | 0 | OCF$_2$CFHCF$_3$ |
| 83 | 3 | H | — | D | D | 1 | 0 | 0 | F |
| 84 | 3 | H | — | D | M | 2 | 0 | 0 | OCF$_3$ |
| 85 | 3 | H | — | M | D | 2 | 0 | 0 | F |
| 86 | 3 | H | — | M | M | 1 | 0 | 0 | OCF$_2$CF$_2$H |
| 87 | 3 | H | — | M | M | 1 | 0 | 0 | CH$_2$CF$_3$ |
| 88 | 3 | H | — | D | M | 1 | 0 | 0 | OCH$_2$CF$_3$ |
| 89 | 3 | H | — | M | B | 1 | 0 | 0 | CF$_2$CF$_3$ |
| 90 | 5 | H | — | D | B | 1 | 0 | 0 | CF$_3$ |
| 91 | 5 | H | — | D | M | 1 | 0 | 0 | OCF$_2$CFHCF$_3$ |
| 92 | 5 | H | — | D | M | 1 | 0 | 0 | F |
| 93 | 5 | H | — | D | M | 1 | 0 | 0 | OCF$_3$ |
| 94 | 3 | H | — | B | B | 0 | 0 | 1 | CF$_3$ |
| 95 | 3 | H | — | B | B | 0 | 0 | 1 | OCF$_3$ |
| 96 | 3 | H | — | B | B | 0 | 0 | 1 | OCF$_2$CFHCF$_3$ |
| 97 | 3 | H | — | B | M | 0 | 0 | 1 | CF$_3$ |
| 98 | 3 | H | — | B | M | 0 | 0 | 1 | OCF$_3$ |
| 99 | 3 | H | — | B | M | 0 | 0 | 1 | OCF$_2$CFHCF$_3$ |
| 100 | 3 | H | — | B | M | 0 | 0 | 1 | F |
| 101 | 3 | H | — | B | D | 0 | 0 | 1 | CF$_3$ |
| 102 | 3 | H | — | B | D | 0 | 0 | 1 | OCF$_3$ |
| 103 | 3 | H | — | B | D | 0 | 0 | 1 | OCF$_2$CFHCF$_3$ |
| 104 | 3 | H | — | B | D | 0 | 0 | 1 | F |
| 105 | 3 | H | — | M | B | 0 | 0 | 1 | CF$_3$ |
| 106 | 3 | H | — | M | B | 0 | 0 | 1 | OCF$_3$ |
| 107 | 3 | H | — | M | B | 0 | 0 | 1 | OCF$_2$CFHCF$_3$ |
| 108 | 3 | H | — | M | B | 0 | 0 | 1 | F |
| 109 | 3 | H | — | M | M | 0 | 0 | 1 | CF$_3$ |
| 110 | 3 | H | — | M | M | 0 | 0 | 1 | OCF$_3$ |
| 111 | 3 | H | — | M | M | 0 | 0 | 1 | OCF$_2$CFHCF$_3$ |

-continued

| Parameter No. | n | Ring E | G | L | Ring Z | k | l | m | Q—Y |
|---|---|---|---|---|---|---|---|---|---|
| 112 | 3 | H | — | M | M | 0 | 0 | 1 | F |
| 113 | 3 | H | — | M | D | 0 | 0 | 1 | CF$_3$ |
| 114 | 3 | H | — | M | D | 0 | 0 | 1 | OCF$_3$ |
| 115 | 3 | H | — | M | D | 0 | 0 | 1 | OCF$_2$CFHCF$_3$ |
| 116 | 3 | H | — | M | D | 0 | 0 | 1 | F |
| 117 | 3 | H | — | D | B | 0 | 0 | 1 | CF$_3$ |
| 118 | 3 | H | — | D | B | 0 | 0 | 1 | OCF$_3$ |
| 119 | 3 | H | — | D | B | 0 | 0 | 1 | OCF$_2$CFHCF$_3$ |
| 120 | 3 | H | — | D | B | 0 | 0 | 1 | F |
| 121 | 3 | H | — | D | M | 0 | 0 | 1 | CF$_3$ |
| 122 | 3 | H | — | D | M | 0 | 0 | 1 | OCF$_3$ |
| 123 | 3 | H | — | D | M | 0 | 0 | 1 | OCF$_2$CFHCF$_3$ |
| 124 | 3 | H | — | D | M | 0 | 0 | 1 | F |
| 125 | 3 | H | — | D | D | 0 | 0 | 1 | CF$_3$ |
| 126 | 3 | H | — | D | D | 0 | 0 | 1 | OCF$_3$ |
| 127 | 3 | H | — | D | D | 0 | 0 | 1 | OCF$_2$CFHCF$_3$ |
| 128 | 3 | H | — | D | D | 0 | 0 | 1 | F |
| 129 | 3 | H | — | M | M | 0 | 0 | 1 | CH$_2$CF$_3$ |
| 130 | 3 | H | — | D | M | 0 | 0 | 1 | OCH$_2$CF$_3$ |
| 131 | 3 | H | — | M | B | 0 | 0 | 1 | CF$_2$CF$_3$ |
| 132 | 3 | H | — | B | B | 0 | 0 | 2 | OCF$_3$ |
| 133 | 3 | H | — | D | M | 0 | 0 | 2 | OCF$_3$ |
| 134 | 5 | H | — | D | D | 0 | 0 | 1 | CF$_3$ |
| 135 | 5 | H | — | M | D | 0 | 0 | 2 | F |
| 136 | 3 | B | — | H | B | 0 | 0 | 0 | CF$_3$ |
| 137 | 3 | B | — | H | B | 0 | 0 | 0 | OCF$_3$ |
| 138 | 3 | B | — | H | B | 0 | 0 | 0 | OCF$_2$CFHCF$_3$ |
| 139 | 3 | M | — | H | B | 0 | 0 | 0 | CF$_3$ |
| 140 | 3 | M | — | H | B | 0 | 0 | 0 | OCF$_3$ |
| 141 | 3 | M | — | H | B | 0 | 0 | 0 | OCF$_2$CFHCF$_3$ |
| 142 | 3 | D | — | H | B | 0 | 0 | 0 | CF$_3$ |
| 143 | 3 | D | — | H | B | 0 | 0 | 0 | OCF$_3$ |
| 144 | 3 | D | — | H | B | 0 | 0 | 0 | OCF$_2$CFHCF$_3$ |
| 145 | 3 | B | — | H | D | 0 | 0 | 0 | CF$_3$ |
| 146 | 3 | B | — | H | M | 0 | 0 | 0 | OCF$_3$ |
| 147 | 3 | B | — | H | M | 0 | 0 | 0 | OCF$_2$CFHCF$_3$ |
| 148 | 3 | B | — | H | D | 0 | 0 | 0 | F |
| 149 | 5 | B | — | H | M | 0 | 0 | 0 | OCF$_3$ |
| 150 | 3 | B | — | H | B | 0 | 0 | 1 | CF$_3$ |
| 151 | 3 | B | — | H | B | 0 | 0 | 1 | OCF$_3$ |
| 152 | 3 | B | — | H | B | 0 | 0 | 1 | OCF$_2$CFHCF$_3$ |
| 153 | 3 | M | — | H | B | 0 | 0 | 1 | CF$_3$ |
| 154 | 3 | M | — | H | B | 0 | 0 | 1 | OCF$_3$ |
| 155 | 3 | M | — | H | B | 0 | 0 | 1 | OCF$_2$CFHCF$_3$ |
| 156 | 3 | D | — | H | B | 0 | 0 | 1 | CF$_3$ |
| 157 | 3 | D | — | H | B | 0 | 0 | 1 | OCF$_3$ |
| 158 | 3 | D | — | H | B | 0 | 0 | 1 | OCF$_2$CFHCF$_3$ |
| 159 | 5 | B | — | H | D | 0 | 0 | 1 | CF$_3$ |
| 160 | 3 | B | — | H | M | 0 | 0 | 1 | OCF$_3$ |
| 161 | 3 | B | — | H | M | 0 | 0 | 1 | OCF$_2$CFHCF$_3$ |
| 162 | 3 | B | — | H | D | 0 | 0 | 1 | F |
| 163 | 3 | B | — | H | M | 0 | 0 | 2 | OCF$_3$ |
| 164 | 5 | B | — | H | M | 0 | 0 | 1 | OCF$_3$ |
| 165 | 3 | B | — | H | B | 0 | 0 | 1 | CF$_3$ |
| 166 | 3 | B | — | H | B | 0 | 0 | 1 | OCF$_3$ |
| 167 | 3 | B | — | H | B | 0 | 0 | 1 | OCF$_2$CFHCF$_3$ |
| 168 | 3 | M | — | H | B | 0 | 0 | 1 | CF$_3$ |
| 169 | 3 | M | — | H | B | 0 | 0 | 1 | OCF$_3$ |
| 170 | 3 | M | — | H | B | 0 | 0 | 1 | OCF$_2$CFHCF$_3$ |
| 171 | 3 | D | — | H | B | 0 | 0 | 1 | CF$_3$ |
| 172 | 3 | D | — | H | B | 0 | 0 | 1 | OCF$_3$ |
| 173 | 3 | D | — | H | B | 0 | 0 | 1 | OCF$_2$CFHCF$_3$ |
| 174 | 3 | B | — | H | D | 0 | 0 | 1 | CF$_3$ |
| 175 | 3 | B | — | H | M | 0 | 0 | 1 | OCF$_3$ |
| 176 | 3 | B | — | H | M | 0 | 0 | 1 | OCF$_2$CFHCF$_3$ |
| 177 | 3 | B | — | H | D | 0 | 0 | 1 | F |
| 178 | 3 | B | — | H | M | 0 | 0 | 2 | OCF$_3$ |
| 179 | 5 | B | — | H | M | 0 | 0 | 1 | OCF$_3$ |
| 180 | 3 | B | — | H | B | 1 | 0 | 1 | CF$_3$ |
| 181 | 3 | B | — | H | B | 1 | 0 | 1 | OCF$_3$ |
| 182 | 3 | B | — | H | B | 1 | 0 | 1 | OCF$_2$CFHCF$_3$ |
| 183 | 3 | M | — | H | B | 1 | 0 | 1 | CF$_3$ |
| 184 | 3 | M | — | H | B | 1 | 0 | 1 | OCF$_3$ |
| 185 | 3 | M | — | H | B | 1 | 0 | 1 | OCF$_2$CFHCF$_3$ |
| 186 | 3 | D | — | H | B | 1 | 0 | 1 | CF$_3$ |
| 187 | 3 | D | — | H | B | 1 | 0 | 1 | OCF$_3$ |
| 188 | 3 | D | — | H | B | 1 | 0 | 1 | OCF$_2$CFHCF$_3$ |
| 189 | 3 | B | — | H | D | 1 | 0 | 1 | CF$_3$ |
| 190 | 3 | B | — | H | M | 1 | 0 | 1 | OCF$_3$ |
| 191 | 3 | B | — | H | M | 1 | 0 | 1 | OCF$_2$CFHCF$_3$ |
| 192 | 3 | B | — | H | D | 1 | 0 | 1 | F |
| 193 | 3 | B | — | H | M | 1 | 0 | 2 | OCF$_3$ |
| 194 | 5 | B | — | H | M | 1 | 0 | 1 | OCF$_3$ |
| 195 | 3 | H | — | H | B | 1 | 0 | 1 | CF$_3$ |
| 196 | 3 | H | — | H | M | 1 | 0 | 1 | OCF$_3$ |
| 197 | 3 | H | — | H | D | 1 | 0 | 1 | F |
| 198 | 5 | H | — | H | B | 1 | 0 | 1 | CF$_3$ |
| 199 | 3 | B | — | B | B | 0 | 0 | 0 | CF$_3$ |
| 200 | 3 | B | — | M | B | 0 | 0 | 0 | OCF$_3$ |
| 201 | 3 | B | — | B | B | 0 | 0 | 0 | OCF$_3$ |
| 202 | 3 | B | — | B | M | 0 | 0 | 0 | OCF$_3$ |
| 203 | 5 | B | — | B | B | 0 | 0 | 0 | OCF$_3$ |
| 204 | 3 | B | — | B | B | 1 | 0 | 0 | CF$_3$ |
| 205 | 3 | B | — | M | B | 1 | 0 | 0 | OCF$_3$ |
| 206 | 3 | B | — | B | B | 1 | 0 | 0 | OCF$_3$ |
| 207 | 3 | B | — | B | M | 1 | 0 | 0 | OCF$_3$ |
| 208 | 5 | B | — | B | B | 1 | 0 | 0 | OCF$_3$ |
| 209 | 3 | B | — | B | B | 0 | 0 | 1 | CF$_3$ |
| 210 | 3 | B | — | M | B | 0 | 0 | 1 | OCF$_3$ |
| 211 | 3 | B | — | B | B | 0 | 0 | 1 | OCF$_3$ |
| 212 | 3 | B | — | B | M | 0 | 0 | 1 | OCF$_3$ |
| 213 | 5 | B | — | B | B | 0 | 0 | 1 | OCF$_3$ |
| 214 | 3 | B | — | B | B | 1 | 0 | 1 | CF$_3$ |
| 215 | 3 | B | — | M | B | 1 | 0 | 1 | OCF$_3$ |
| 216 | 3 | B | — | B | B | 1 | 0 | 1 | OCF$_3$ |
| 217 | 3 | B | — | B | M | 1 | 0 | 1 | OCF$_3$ |
| 218 | 5 | B | — | B | B | 1 | 0 | 1 | OCF$_3$ |
| 219 | 3 | H | H | H | B | 0 | 0 | 0 | CF$_3$ |
| 220 | 3 | H | H | H | B | 0 | 0 | 0 | OCF$_3$ |
| 221 | 3 | H | H | H | B | 0 | 0 | 0 | OCF$_2$CFHCF$_3$ |
| 222 | 3 | H | H | H | M | 0 | 0 | 0 | CF$_3$ |
| 223 | 3 | H | H | H | M | 0 | 0 | 0 | OCF$_3$ |
| 224 | 3 | H | H | H | M | 0 | 0 | 0 | OCF$_2$CFHCF$_3$ |
| 225 | 3 | H | H | H | M | 0 | 0 | 0 | F |
| 226 | 3 | H | H | H | D | 0 | 0 | 0 | CF$_3$ |
| 227 | 3 | H | H | H | D | 0 | 0 | 0 | OCF$_3$ |
| 228 | 3 | H | H | H | D | 0 | 0 | 0 | OCF$_2$CFHCF$_3$ |
| 229 | 3 | H | H | H | D | 0 | 0 | 0 | F |
| 230 | 3 | H | H | H | B | 0 | 0 | 0 | CH$_2$CF$_3$ |
| 231 | 3 | H | H | H | B | 0 | 0 | 0 | OCH$_2$CF$_3$ |
| 232 | 3 | H | H | H | B | 0 | 0 | 0 | CF$_2$CF$_3$ |
| 233 | 5 | H | H | H | M | 0 | 0 | 0 | OCF$_3$ |
| 234 | 3 | H | H | H | M | 1 | 0 | 0 | OCF$_3$ |
| 235 | 3 | H | H | H | M | 0 | 1 | 0 | OCF$_3$ |
| 236 | 3 | H | H | H | M | 0 | 0 | 1 | OCF$_3$ |
| 237 | 3 | H | H | B | B | 0 | 0 | 0 | CF$_3$ |
| 238 | 3 | H | H | B | M | 0 | 0 | 0 | OCF$_3$ |
| 239 | 3 | H | H | M | M | 0 | 0 | 0 | OCF$_3$ |
| 240 | 3 | H | H | D | M | 0 | 0 | 0 | OCF$_3$ CN79 NI225 |
| 241 | 3 | H | H | D | B | 0 | 0 | 0 | OCF$_3$ |
| 242 | 3 | H | H | M | D | 0 | 0 | 0 | OCF$_3$ |
| 243 | 3 | H | H | B | M | 0 | 0 | 0 | OCF$_2$CFHCF$_3$ |
| 244 | 3 | H | H | M | M | 0 | 0 | 0 | OCF$_2$CFHCF$_3$ |
| 245 | 3 | H | H | D | M | 0 | 0 | 0 | OCF$_2$CFHCF$_3$ |
| 246 | 3 | H | H | M | D | 0 | 0 | 0 | F |
| 247 | 5 | H | H | D | B | 0 | 0 | 0 | OCF$_3$ |
| 248 | 3 | H | H | D | M | 1 | 0 | 0 | OCF$_3$ |
| 249 | 3 | H | H | D | M | 0 | 1 | 0 | OCF$_3$ |
| 250 | 3 | H | H | D | M | 0 | 0 | 1 | OCF$_3$ |
| 251 | 3 | H | B | B | B | 0 | 0 | 0 | CF$_3$ |
| 252 | 3 | H | B | B | B | 0 | 0 | 0 | OCF$_3$ |
| 253 | 3 | H | B | B | M | 0 | 0 | 0 | OCF$_3$ |
| 254 | 3 | H | B | B | B | 1 | 0 | 0 | OCF$_3$ |
| 255 | 3 | H | B | B | B | 0 | 1 | 0 | OCF$_3$ |
| 256 | 3 | H | B | B | B | 0 | 0 | 1 | OCF$_3$ |
| 257 | 3 | B | B | B | B | 0 | 0 | 0 | CF$_3$ |
| 258 | 3 | B | B | B | B | 0 | 0 | 0 | OCF$_3$ |
| 259 | 3 | B | B | B | M | 0 | 0 | 0 | OCF$_3$ |
| 260 | 3 | B | B | B | B | 1 | 0 | 0 | OCF$_3$ |
| 261 | 3 | B | B | B | B | 0 | 1 | 0 | OCF$_3$ |
| 262 | 3 | B | B | B | B | 0 | 0 | 1 | OCF$_3$ |
| 263 | 3 | H | B | H | B | 0 | 0 | 0 | CF$_3$ |

-continued

| Parameter No. | n | Ring E | G | L | Ring Z | k | l | m | Q—Y |
|---|---|---|---|---|---|---|---|---|---|
| 264 | 3 | H | B | H | B | 0 | 0 | 0 | OCF$_3$ |
| 265 | 3 | H | B | H | M | 0 | 0 | 0 | OCF$_3$ |
| 266 | 3 | H | B | H | B | 1 | 0 | 0 | OCF$_3$ |
| 267 | 3 | H | B | H | B | 0 | 1 | 0 | OCF$_3$ |
| 268 | 3 | H | B | H | B | 0 | 0 | 1 | OCF$_3$ |
| 269 | 3 | B | B | H | B | 0 | 0 | 0 | CF$_3$ |
| 270 | 3 | B | B | H | B | 0 | 0 | 0 | OCF$_3$ |
| 271 | 3 | B | B | H | M | 0 | 0 | 0 | OCF$_3$ |
| 272 | 3 | B | B | H | B | 1 | 0 | 0 | OCF$_3$ |
| 273 | 3 | B | B | H | B | 0 | 1 | 0 | OCF$_3$ |
| 274 | 3 | B | B | H | B | 0 | 0 | 1 | OCF$_3$ |
| 275 | 3 | B | H | B | B | 0 | 0 | 0 | CF$_3$ |
| 276 | 3 | B | H | B | B | 0 | 0 | 0 | OCF$_3$ |
| 277 | 3 | B | H | B | M | 0 | 0 | 0 | OCF$_3$ |
| 278 | 3 | B | H | B | B | 1 | 0 | 0 | OCF$_3$ |
| 279 | 3 | B | H | B | B | 0 | 1 | 0 | OCF$_3$ |
| 280 | 3 | B | H | B | B | 0 | 0 | 1 | OCF$_3$ |
| 281 | 3 | B | H | H | B | 0 | 0 | 0 | CF$_3$ |
| 282 | 3 | B | H | H | B | 0 | 0 | 0 | OCF$_3$ |
| 283 | 3 | B | H | H | M | 0 | 0 | 0 | OCF$_3$ |
| 284 | 3 | B | H | H | B | 1 | 0 | 0 | OCF$_3$ |
| 285 | 3 | B | H | H | B | 0 | 1 | 0 | OCF$_3$ |
| 286 | 3 | B | H | H | B | 0 | 0 | 1 | OCF$_3$ |

EXAMPLE 10

(Use example 1)

A liquid crystal composition (A1) consisting of

| | |
|---|---|
| 4-(4-propylcyclohexyl)benzonitrile | 24% |
| 4-(4-pentylcyclohexyl)benzonitrile | 36% |
| 4-(4-heptylcyclohexyl)benzonitrile | 25% and |
| 4-(4-pentylphenyl)benzonitrile | 15% | was prepared. This nematic liquid crystal composition exhibited a clearing point of 72.4° C., a threshold voltage in a cell thickness of 9 µm, of 1.78V, a Δε of 11.0, a Δn of 0.137 and a viscosity at 20° C., of 27.0 mPa.S. With this liquid crystal composition (85%) was blended 1-(2-(4-(3-fluoropropyl)cyclohexyl)ethyl)-3,5-difluoro-4-(3,5-difluoro-4-trifluoromethylphenyl)benzene of Example 1 of the present invention (15%), to prepare a liquid crystal composition (B1). This composition exhibited a threshold voltage in a cell thickness of 8.8 µm, of 1.39 V, a Δε of 12.0, a Δn of 0.131, and an elastic constant of $K_{33}/K_{11}$, of 2.13. Further, the extrapolated values calculated from the blending ratios were respectively a Δε of 17.7 and a Δn of 0.097. This composition was allowed to stand for 60 days in a breezer of −20° C., but no crystal deposition was observed.

EXAMPLE 1

(Use example 2)

A liquid crystal composition (A2) consisting of

| | |
|---|---|
| 4-(4-propylcyclohexyl)benzonitrile | 30% |
| 4-(4-pentylcyclohexyl)benzonitrile | 40% and |
| 4-(4-heptylcyclohexyl)benzonitrile | 30% | was prepared. This nematic liquid crystal composition exhibited a clearing point of 52.3° C., a threshold voltage in a cell thickness of 9 µm, of 1.60 V, a Δε of 10.7 a Δn of 0.119, and a viscosity at 20° C., of 21.7 Pa.S. With this liquid crystal composition (85%) was blended 1-(2-(4-(4-(2-fluoroethyl)cyclohexyl)cyclohexyl)ethyl-4-trifluoromethoxybenzene (a compound of Example 2 of the present invention) (15%), to prepare a liquid crystal composition (B2). This composition exhibited a clearing point of 56.1° C., a threshold voltage in a cell thickness, of 8.8 µm, of 1.55 V, a Δε of 10.2, a Δn of 0.112 and a viscosity at 20° C., of 22.3 mPa.S. Further, the extraporated values calculated from the blending ratios were respectively a clearing point of 77.6° C., a Δε of 7.4, a Δn of 0.072, and a viscosity at 20° C., of 25.7 mPa.S. Further, this composition was allowed to stand 60 days in a freezer at −20° C., but no crystal deposition was observed.

EXAMPLE 12

(Use example 3)

With the above liquid crystal composition (A2) (85%) was blended 1-(1-(4-(3-fluoropropyl)cyclohexyl)ethyl)-3,5-difluoro-4-(3-fluoro-4-trifluoromethoxyphenyl)benzene of a compound of Example 4 (15%), to prepare a liquid crystal composition (B3). This composition exhibited a clearing point of 64.5° C., a threshold voltage in a cell thickness of 8.8 µm, of 1.52 V, a Δε of 11.1, a Δn of 0.122, and a viscosity at 20° C., 27.8 mPa.S. Further, the extrapolated values calculated from the blending ratios were respectively a clearing point of 133.6° C., a Δε of 13.4, a Δn of 0.139, and a viscosity at 20° C., of 62.4 mPa.S. Further, this composition was allowed to stand for 60 days in a freezer at −20° C., but no crystal deposition was observed.

EXAMPLE 13

(Use example 4)

With the above liquid crystal composition (A1) (85%) was blended 1-(2-(4-(3-fluoropropyl)cyclohexyl)ethyl)-3,5-difluoro-4-(3-fluoro-4-trifluoromethoxyphenyl)benzene of a compound of Example 5 (15%), to prepare a liquid crystal composition (B4). This composition exhibited a clearing point of 63.3° C., a threshold voltage in a cell thickness of 8.8 µm, of 1.47 V, a Δε of 11.4, a Δn of 0.130, and a viscosity at 20° C., of 34.1 mPa.S. Further, the extrapolated values calculated from the blending ratios were respectively a clearing point of 15.7° C., a Δε of 13.7, a Δn of 0.090, and a viscosity at 20° C., of 67.5 mPa.S. Further, this composition was allowed to stand for 60 days in a freezer at −20° C., but no crystal deposition was observed.

EXAMPLE 14

(Use example 5)

With the above liquid crystal composition (A1) (85%) was blended 1-(2-(4-(4-(3-fluoropropyl)cyclohexyl)cyclohexyl)ethyl)-4-trifluoromethylbenzene of a compound of Example 6 of the present invention (15%), to prepare a liquid crystal composition (B5). This composition exhibited a clearing point of 74.9° C., a threshold voltage in a cell thickness of 8.9 µm, of 1.79 V, a Δε of 10.6, a Δn of 0.130 and a viscosity at 20° C., of 29.7 mPa.S. Further, the extrapolated values calculated from the blending ratios were respectively a clearing point of 93.0° C., a Δε of 8.3, a Δn of 0.090 and a viscosity at 20° C., of 46.7 mPa.S. Further, this composition was allowed to stand for 60 days in a freezer at −20° C., but no crystal deposition was observed.

EXAMPLE 15

(Use example 6)

With the above composition (A1) (85%) was blended 1-(2-(4-(4-(3-fluoropropyl)cyclohexyl)cyclohexyl)ethyl)-4- trifluoromethoxybenzene of a compound of Example 7 (15%), to prepare a liquid crystal composition (B6). This composition exhibited a clearing point of 77.1° C., a threshold voltage in a cell thickness of 8.7 μm, of 1.78 V, a Δε of 10.2, a Δn of 0.130 and a viscosity at 20° C., of 27.8 mPa.S. Further, the extrapolated values calculated from the blending ratios were respectively a clearing point of 107.7° C., a Δε of 5.7, a Δn of 0.090 and a viscosity at 20° C., of 32.9 mPa.S. Further, this composition was allowed to stand for 60 days in a freezer at −20° C., but no crystal deposition was observed.

EXAMPLE 16

(Use example 7)

With the above liquid crystal composition (A1) (85%) was blended 1-(3-fluoropropyl)cyclohexyl)-3-fluoro-4-trifluoromethoxybenzene of a compound of Example 8 of the present invention (B7) (15%), to prepare a liquid crystal composition (B7). This composition exhibited a Δε of 9.9. Further, the Δε calculated from the blending ratios was 3.7. Further, this composition was allowed to stand for 60 days in a freezer at −20° C., but no crystal deposition was observed.

EXAMPLE 17

(Comparative example 1)

With the above liquid crystal composition (A2) (50%) was blended a compound, 1-(4-(2-fluoroethyl)cyclohexyl)-4-(3,4,5-trifluorophenyl)benzene (50%), disclosed in Japanese patent application Hyo No. Hei 04-506817, formula (6), to prepare a liquid crystal composition (B4). On the other hand, with the liquid crystal composition (A2) (50%) was blended a compound of Example 2, 1-(2-(4-(4-(2-fluoroethyl)cyclohexyl)cyclohexyl)ethyl)-4-trifluoromethoxybenzene (50%), to prepare a liquid crystal composition (B5). These liquid crystal compositions B4 and B5 were respectively allowed to stand for 60 days in a freezer at −20° C. In the case of B5, no crystal deposition was observed, but in the case of B4, crystal deposition was observed.

EXAMPLE 18

(Comparative example 2)

A liquid crystal composition (A3) consisting of the following compounds were prepared:

| | |
|---|---|
| 1-(4-(4-ethylcyclohexyl)cyclohexyl)-3,4-difluorobenzene | 16.67% |
| 1-(4-(4-propylcyclohexyl)cyclohexyl)-3,4-difluorobenzene | 16.67% |
| 1-(4-(4-pentylcyclohexyl)cyclohexyl)-3,4-difluorobenzene | 16.66% |
| 1-(4-(2-(4-ethylcyclohexyl)ethyl)cyclohexyl)-3,4-difluorobenzene | 10.00% |
| 1-(4-(2-(4-propylcyclohexyl)ethyl)cyclohexyl)-3,4-difluorobenzene | 5.00% |
| 1-(4-(2-(4-pentylcyclohexyl)ethyl)cyclohexyl)-3,4-difluorobenzene | 10.00% |
| 1-(4-(4-ethylcyclohexyl)phenyl)-3,4-difluorobenzene | 6.25% |
| 1-(4-(4-propylcyclohexyl)phenyl)-3,4-difluorobenzene | 6.25% |
| 1-(4-(4-pentylcyclohexyl)phenyl)-3,4-difluorobenzene | 12.50%. |

With this liquid crystal composition (A3) (57%) was blended a compound, (1-(2-(4-(4-propylcyclohexyl)cyclohexyl)ethyl)-4-trifluoromethoxybenzene) (43%), to prepare a liquid crystal composition (B9). On the other hand, with the liquid crystal composition (A2) (57%) was blended (1-(2-(4-(4-(3-fluoropropyl)cyclohexyl)cyclohexyl)ethyl)-4-trifluoromethoxybenzene) (43%) of a compound of Example 7, to prepare a liquid crystal composition (B10). These liquid crystal compositions B9 and B10 were respectively allowed to stand for 18 hours in a freezer at −40° C. In the case of B10, no crystal deposition was observed, but in the case of B9, crystal deposition was observed.

The compounds of the present invention have a very large Δε exceeding 20 in certain cases, and further, overcome an inferior compatibility and a narrow liquid crystal range which have been so far a problem common to the compounds having a high Δε, and still further have a low viscosity and a sufficient, chemical stability.

The liquid crystal compositions containing these compounds as components are chemically very stable and exhibit a large Δε, and further, have superior characteristics of exhibiting nematic phase within a broad and practical temperature range, reflected from the superior compatibility and broad liquid crystal range of the compounds and the low viscosity thereof. Thus, the compositions obtained by using these compounds are very useful when liquid crystal display elements are constructed.

For example, as compared with the compound (1), compounds No. 17 and No. 19 both have the same extents of the specific resistance value and the compatibility, but have a large Δε and a far elevated clearing point, and on the other hand, a far reduced viscosity, and as compared with the compound (5), they have the same extents of the clearing point, viscosity Δε and Δn, but have a far superior compatibility; hence they are useful as a composition component of TFT display element. Further, compounds No. 18, No. 70 and No. 80 each exhibit a large Δε, a superior compatibility, a large Δn and a high specific resistance value; hence they are useful as the composition component of TFT display element. Compound No. 240 exhibits a large Δε, a large Δn and a property of far elevating the clearing point; hence it is very useful as a composition component.

Compound No. 74 has a large Δε and a very large Δn and a superior compatibility; hence it is useful as a composition component of TFT display element.

Bicyclic compound No. 13 has a somewhat low clearing point, but has a large Δε and a very low viscosity; hence it is useful as a composition component of TFT display element.

What we claim is:

1. A liquid crystalline compound expressed by the formula (I):

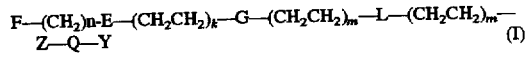

wherein n represents an integer of 1 to 10; k, l and m each independently represent an integer of 0 to 2; E represents 1,4-cyclohexylene group or 1,4-phenylene group wherein one or more hydrogen atoms on a six-membered ring may be replaced by fluorine atom(s); G and L each independently represent a covalent bond or 1,4-cyclohexylene group or 1,4-phenylene group wherein one or more hydrogen atoms may be replaced by fluorine atom(s), provided that when only one of G or L is a covalent bond, G is the covalent bond; Z represents 1,4-phenylene group wherein one or more hydrogen atoms on the 1,4-phenylene group may be replaced by fluorine atom(s); Q represents a covalent bond or —O—; Y represents a fluoroalkyl group of 1 to 3 carbon atoms or fluorine atom; and when E represents 1,4-cyclohexylene group and at least one of G and L represents a covalent bond, k+l+m≠0 and when Q represents —O—, Y does not represent fluorine atom.

2. A liquid crystalline compound according to claim 1, wherein k, l and m each independently represent 0 or 1, and E represents 1,4-phenylene group or fluorine-substituted 1,4-phenylene group.

3. A liquid crystalline compound according to claim 1, wherein k, l and m each independently represent 0 or 1 and E represents 1,4-cyclohexylene group.

4. A liquid crystalline compound according to claim 3, wherein k, l and m each are zero; G represents a covalent bond; and L represents 1,4-cyclohexylene group, 1,4-phenylene group or fluorine-substituted 1,4-phenylene group.

5. A liquid crystalline compound according to claim 4, wherein L represents 1,4-cyclohexylene group.

6. A liquid crystalline compound according to claim 4, wherein L represents 1,4-phenylene group or fluorine-substituted 1,4-phenylene group.

7. A liquid crystalline compound according to claim 3, wherein k and l each represent 0; m represents 1; G represents a covalent bond; and L represents 1,4-cyclohexylene group, 1,4-phenylene group or fluorine-substituted 1,4-phenylene group.

8. A liquid crystalline compound according to claim 7, wherein L represents 1,4-cyclohexylene group.

9. A liquid crystalline compound according to claim 7, wherein L represents 1,4-phenylene group or fluorine-substituted 1,4-phenylene group.

10. A liquid crystalline compound according to claim 3, wherein k represents 1; l and m each represent 0; and G and L each represent a covalent bond.

11. A liquid crystalline compound according to claim 1, wherein G and L each independently represent 1,4-cyclohexylene group, 1,4-phenylene group or fluorine-substituted phenylene group.

12. A liquid crystalline compound expressed by the formula (I):

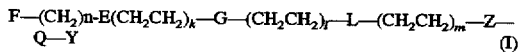

wherein n represents an integer of 1 to 10; k and m each represent the integer 1, and l represents 0; E represents 1,4-cyclohexylene group wherein one or more hydrogen atoms on the cyclohexylene ring may be replaced by fluorine atom(s); G represents a covalent bond; L represents 1,4-cyclohexylene group wherein one or more hydrogen atoms on the cyclohexylene ring may be replaced by fluorine atom(s), or L represents fluorine-substituted 1,4-phenylene group; Z represents 1,4-phenylene group wherein one or more hydrogen atoms on the 1,4-phenylene group may be replaced by fluorine atom(s); Q represents a covalent bond or —O—; Y represents a fluoroalkyl group of 1 to 3 carbon atoms or fluorine atom; k+l+m≠0; and when Q represents —O—, Y does not represent fluorine atom.

13. A liquid crystal composition containing at least one of liquid crystalline compounds according to one of claim 2 to 9, 10, 11, 1 or 12.

14. A liquid crystal composition containing at least one member of the liquid crystalline compounds set forth in one of claims 2 to 9, 10, 11, 1 or 12, as a first component, and at least one member of compounds selected from the group consisting of compounds expressed by the following formulas (II), (III) and (IV), as a second component:

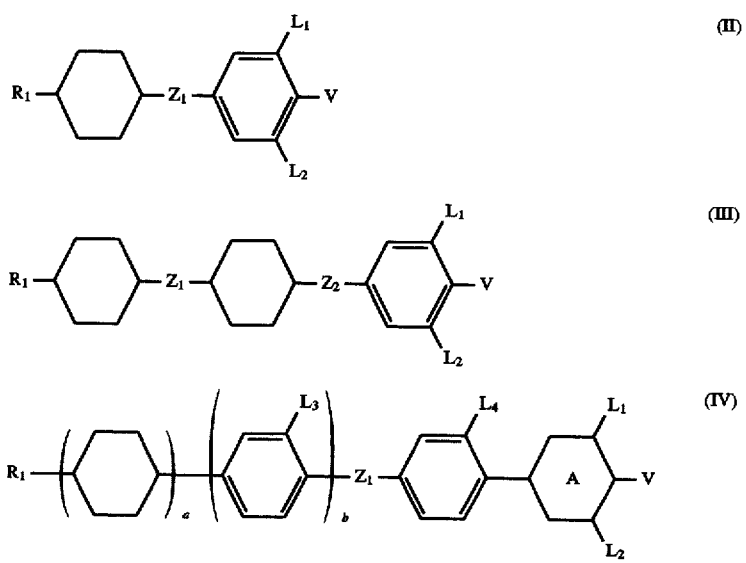

wherein $R_1$ represents an alkyl group of 1 to 10 carbon atoms; V represents F, Cl, $CF_3$, $OCF_3$, $OCF_2H$ or an alkyl group of 1 to 10 carbon atoms; $L_1$, $L_2$, $L_3$ and $L_4$ each independently represent H or F; $Z_1$ and $Z_2$ each independently represent —$(CH_2)_2$—, —CH=CH— or a covalent bond; ring A represents trans-1,4-cyclohexylene group or 1,4-phenylene group; a represents 1 or 2; and b represents 0 or 1.

15. A liquid crystal composition containing at least one member of the liquid crystalline compounds set forth in one of claims 2 to 9, 10, 11, 1, or 12, as a first component, and at least one member of compounds selected from the group consisting of compounds expressed by the following formulas (V), (VI), (VII), (VIII) and (IX), as a second component:

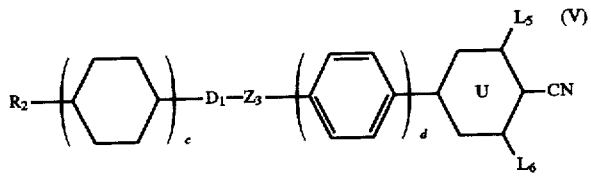

(V)

wherein $R_2$ represents F, an alkyl group of 1 to 10 carbon atoms or an alkenyl group of 2 to 10 carbon atoms, and in either of the groups, an optional methylene group (—$CH_2$—) in the groups may be replaced by oxygen atom (—O—), but two or more methylene groups therein are not continuously replaced by oxygen atom; $Z_3$ represents —$(CH_2)_2$—, —COO or a covalent bond; $L_5$ and $L_6$ each independently represent H or F; $D_1$ represents trans-1,4-cyclohexylene group, 1,4-phenylene group or 1,3-dioxane-2,5-diyl group; ring U represents trans-1,4-cyclohexylene group or 1,4-phenylene group; and c and d each independently represent 0 or 1,

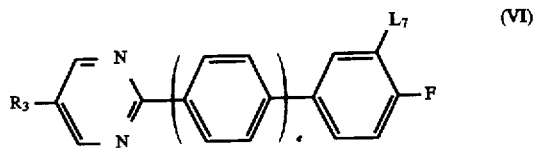

(VI)

wherein $R_3$ represents an alkyl group of 1 to 10 carbon atoms; $L_7$ represents H or F; and e represents 0 or 1,

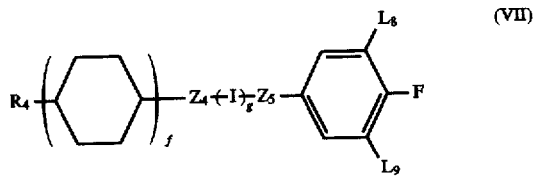

(VII)

wherein $R_4$ represents an alkyl group of 1 to 10 carbon atoms; I represents trans-1,4-cyclohexylene group or 1,4-phenylene group; $L_8$ and $L_9$ each independently represent H or F; $Z_4$ represents —COO— or a covalent bond; $Z_5$ represents —COO— or —C≡C—; and f and g each independently represent 0 or 1,

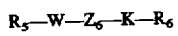 (VIII)

wherein $R_5$ and $R_6$ each independently represent an alkyl group, an alkoxy group or an alkoxymethyl group, each of 1 to 10 carbon atoms; W represents trans-1,4-cyclohexylene group, 1,4-phenylene group or 1,3-pyrimidine-2,5-diyl group; K represents trans-1,4-cyclohexylene group or 1,4-phenylene group; and $Z_6$ represents —C≡C—, —COO—, —$(CH_2)_2$— or a covalent bond,

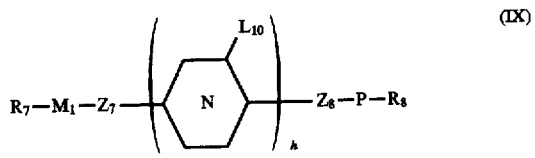

(IX)

wherein $R_7$ represents an alkyl group or an alkoxy group each of 1 to 10 carbon atoms; $R_8$ represents an alkyl group of 1 to 10 carbon atoms, and an optional methylene group (—$CH_2$—) in $R_8$ may be replaced by oxygen atom (—O—), but two or more methylene groups are not continuously replaced by oxygen atom (—O—); $M_1$ represents trans-1,4-cyclohexylene group or 1,3-pyrimidine-2,5-diyl group; rings N and P each independently represent trans-1,4-cyclohexylene group or 1,4-phenylene group; $Z_7$ represents —COO—, —$(CH_2)_2$—, —CH=CH— or a covalent bond; $Z_8$ represents —C≡C—, —COO— or a covalent bond; h represents 0 or 1; and $L_{10}$ represents H or F.

16. A liquid crystal display element comprising the liquid crystal composition set forth in claim 13.

17. A liquid crystal display element comprising the liquid crystal composition set forth in claim 14.

18. A liquid crystal display element comprising the liquid crystal composition set forth in claim 15.

19. A liquid crystal composition containing at least one member of the liquid crystalline compounds set forth in one of claims 2 to 9, 10, 11, 1, or 12, as a first component, and at least one member of compounds selected from the group consisting of compounds expressed by the formulas (II), (III) and (IV), as a part of the second component, and at least one member of compounds selected from the group consisting of compounds expressed by the formulas (V), (VI), (VII), (VIII) and (IX), as another part of the second component.

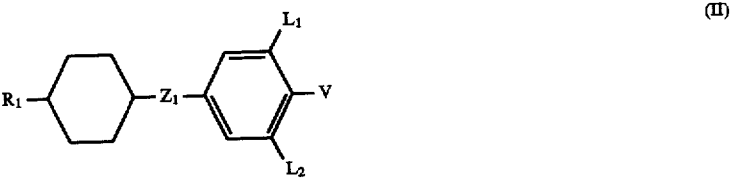

(II)

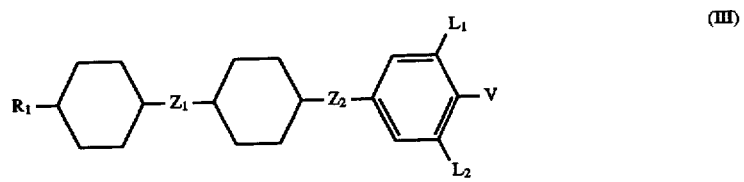

(III)

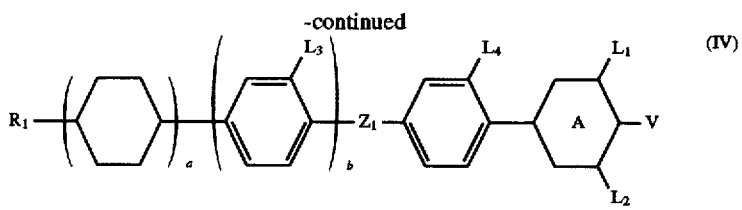

(IV)

wherein $R_1$ represents an alkyl group of 1 to 10 carbon atoms; V represents F, Cl, $CF_3$, $OCF_3$, $OCF_2H$ or an alkyl group of 1 to 10 carbon atoms; $L_1$, $L_2$, $L_3$ and $L_4$ each independently represent H or F; $Z_1$ and $Z_2$ each independently represent $-(CH_2)_2-$, $-CH=CH-$ or a covalent bond; ring A represents trans-1,4-cyclohexylene group or 1,4-phenylene group; a represents 1 or 2; and b represents 0 or 1,

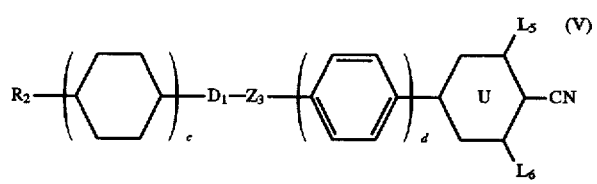

(V)

wherein $R_2$ represents F, an alkyl group of 1 to 10 carbon atoms or an alkenyl group of 2 to 10 carbon atoms, and in either of the groups, an optional methylene group ($-CH_2-$) in the groups may be replaced by oxygen atom ($-O-$), but two or more methylene groups therein are not continuously replaced by oxygen atom; $Z_3$ represents $-(CH_2)_2-$, $-COO-$ or a covalent bond; $L_5$ and $L_6$ each independently represent H or F; $D_1$ represents trans-1,4-cyclohexylene group, 1,4-phenylene group or 1,3-dioxane-2,5-diyl group; ring U represents trans-1,4-cyclohexylene group or 1,4-phenylene group; and c and d each independently represent 0 or 1,

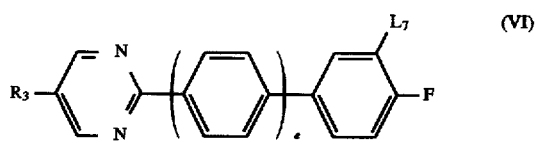

(VI)

wherein $R_3$ represents an alkyl group of 1 to 10 carbon atoms; $L_7$ represents H or F; and e represents 0 or 1,

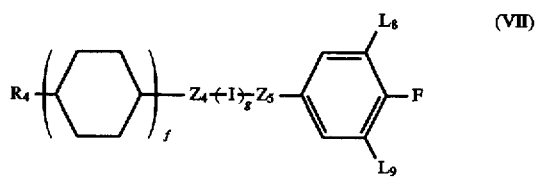

(VII)

wherein $R_4$ represents an alkyl group of 1 to 10 carbon atoms; I represents trans-1,4-cyclohexylene group or 1,4-phenylene group; $L_8$ and $L_9$ each independently represent H or F; $Z_4$ represents $-COO-$ or a covalent bond; $Z_5$ represents $-COO-$ or $-C\equiv C-$; and f and g each independently represent 0 or 1, $$R_5-W-Z_6-K-R_6 \quad (VIII)$$

wherein $R_5$ and $R_6$ each independently represent an alkyl group, an alkoxy group or an alkoxymethyl group, each of 1 to 10 carbon atoms; W represents trans-1,4-cyclohexylene group, 1,4-phenylene group or 1,3-pyrimidine-2,5-diyl group; K represents trans-1,4-cyclohexylene group or 1,4-phenylene group; and $Z_6$ represents $-C\equiv C-$, $-COO-$, $-(CH_2)_2-$ or a covalent bond,

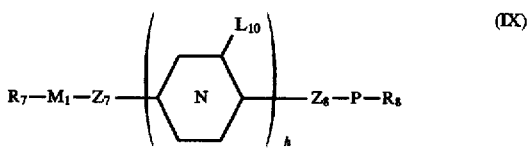

(IX)

wherein $R_7$ represents an alkyl group or an alkoxy group each of 1 to 10 carbon atoms; $R_8$ represents an alkyl group of 1 to 10 carbon atoms, and an optional methylene group ($-CH_2-$) in $R_8$ may be replaced by oxygen atom ($-O-$), but two or more methylene groups are not continuously replaced by oxygen atom ($-O-$); M represents trans-1,4-cyclohexylene group or 1,3-pyrimidine-2,5-diyl group; rings N and P each independently represent trans-1,4-cyclohexylene group or 1,4-phenylene group; $Z_7$ represents $-COO-$, $-(CH_2)_2-$, $-CH=CH-$ or a covalent bond; $Z_8$ represents $-C\equiv C-$, $-COO-$ or a covalent bond; h represents 0 or 1; and $L_{10}$ represents H or F.

20. A liquid crystal display element comprising the liquid crystal composition set forth in claim 19.

* * * * *